(12) United States Patent
Dubensky, Jr. et al.

(10) Patent No.: US 8,287,883 B2
(45) Date of Patent: *Oct. 16, 2012

(54) LISTERIA ATTENUATED FOR ENTRY INTO NON-PHAGOCYTIC CELLS, VACCINES COMPRISING THE LISTERIA, AND METHODS OF USE THEREOF

(75) Inventors: Thomas W. Dubensky, Jr., Piedmont, CA (US); Dirk G. Brockstedt, Richmond, CA (US); David N. Cook, Lafayette, CA (US)

(73) Assignee: Aduro Biotech, Inc., Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/748,586

(22) Filed: Mar. 29, 2010

(65) Prior Publication Data

US 2011/0201092 A1    Aug. 18, 2011

Related U.S. Application Data

(66) Continuation of application No. 10/773,792, filed on Feb. 6, 2004, now Pat. No. 7,691,393, Substitute for application No. 60/446,051, filed on Feb. 6, 2003.

(60) Provisional application No. 60/449,153, filed on Feb. 21, 2003, provisional application No. 60/490,089, filed on Jul. 24, 2003, provisional application No. 60/511,719, filed on Oct. 15, 2003, provisional application No. 60/511,919, filed on Oct. 15, 2003, provisional application No. 60/511,869, filed on Oct. 15, 2003, provisional application No. 60/541,515, filed on Feb. 2, 2004.

(51) Int. Cl.
*A61K 39/02* (2006.01)

(52) U.S. Cl. .............. 424/235.1; 424/184.1; 424/234.1; 435/243; 435/245; 435/252.1; 435/252.3

(58) Field of Classification Search .................. None
See application file for complete search history.

(56) References Cited

U.S. PATENT DOCUMENTS 7,691,393 B2 *  4/2010  Dubensky et al. ......... 424/235.1

OTHER PUBLICATIONS

Appelberg et al (Infect. Immun. Feb. 2000. 68(2): 912-914).*
Drevets (Infect.Immun. Jan. 1998. 66(1): 232-238).*

* cited by examiner

*Primary Examiner* — Jennifer Graser
(74) *Attorney, Agent, or Firm* — Michael A. Whittaker; Acuity Law Group, P.C.

(57) ABSTRACT

The present invention provides *Listeria* that are attenuated for entry into non-phagocytic cells as well as a variety of methods of inducing immune responses involving administering compositions comprising the attenuated *Listeria*. Some of the attenuated *Listeria* are mutant *Listeria* that comprise at least one mutation in a gene encoding an invasin, such as an internalin. Some of the attenuated *Listeria* are further attenuated for cell-to-cell spread. Pharmaceutical compositions and vaccines useful in the methods of the invention are further provided. Methods of making and improving vaccines are also provided.

10 Claims, 26 Drawing Sheets

HBSS

ΔactA

ΔactA AH1A5

Δact ΔinlB AH1A5

LISTERIA ATTENUATED FOR ENTRY INTO NON-PHAGOCYTIC CELLS, VACCINES COMPRISING THE LISTERIA, AND METHODS OF USE THEREOF

RELATED APPLICATIONS

This application is a continuation of U.S. patent application Ser. No. 10/773,792, filed Feb. 6, 2004 now U.S. Pat. No. 7,691,393, entitled "LISTERIA ATTENUATED FOR ENTRY INTO NON-PHAGOCYTIC CELLS, VACCINES COMPRISING. THE LISTERIA, AND METHODS OF USE THEREOF", which claims the priority benefit of U.S. Provisional Application No. 60/446,051, filed Feb. 6, 2003, U.S. Provisional Application No. 60/449,153, filed Feb. 21, 2003, U.S. Provisional Application No. 60/490,089, filed Jul. 24, 2003, U.S. Provisional Application No. 60/511,719, filed Oct. 15, 2003, U.S. Provisional Application No. 60/511,919, filed Oct. 15, 2003, U.S. Provisional Application No. 60/511, 869, filed Oct. 15, 2003, and U.S. Provisional Application No. 60/541,515, filed Feb. 2, 2004, the contents of each of which are hereby incorporated by reference into the present disclosure.

FIELD OF THE INVENTION

The field of this invention relates generally to attenuated bacteria for use in vaccines. In particular, this invention relates to attenuated *Listeria monocytogenes* useful in vaccine compositions and methods of using those vaccines in treatments.

BACKGROUND OF THE INVENTION

Microbes have been developed fin use as vaccines that deliver heterologous antigens. Heterologous antigen delivery is provided by microbes that have been modified to contain nucleic acid sequences encoding a protein or antigen originating from a different species. Heterologous antigen delivery is especially advantageous for treating or preventing diseases or conditions that result from especially virulent or lethal sources, such as cancer and pathogenic agents (for example, HIV or Hepatitis B). Injection of a native or virulent infectious agent is potentially deleterious to the recipient organism. Likewise, a cancer cell which arises sporadically in an affected individual can subsequently propagate and likewise be potentially deleterious to a recent organism. Heterologous antigen delivery is also especially advantageous where administration of attenuated or killed agent or cell has proven unsuccessful in eliciting an effective immune response or where sufficient attenuation of the infectious agent or cancer cell cannot be assured with acceptable certainty. Recently, certain bacterial strains have been developed as recombinant vaccines. For instance, an oral vaccine of attenuated *Salmonella* modified to express *Plasmodium berghei* circumsporozite antigen has been shown to protect mice against malaria (Aggarwal et al. 1990. J. Exp. Med. 172:1083).

One class of bacteria that can potentially be used as heterologous vaccines is facultative intracellular bacteria. The immune response to these bacteria can be a humoral response, a cell-mediated response, or both. However, killed intracellular bacteria or components of intracellular bacteria may not elicit a full cell-mediated immune response (Lauvau et el. 2001. *Science* 294:1735-9). These bacteria can spend a portion of their life cycle free in the circulatory or lymphatic systems of their host, where they are subject to the innate and antibody (i.e., humoral) responses of the host's immune system.

Facultative intracellular bacteria also may spend a portion of their life cycle sequestered within the host's cells, where they may be protected from the innate and humoral aspects of the host's immune system and may be susceptible to the cell-mediated responses of the host's immune system. A cell-mediated immune response is an immune response that stimulates effector T lymphocytes, which may in turn become memory (effector or central) T cells. A cell-mediated immune response results from the presentation of antigens on the surface of host cells. Phagocytic cell of the host's immune system can engulf live bacteria, killed bacteria or components of the bacteria into lysosomes, which mature into phagolysosomes and degrade protein antigens into peptides. Peptides of antigens contained within phagolysosomes of phagocytic cells may be presented on the surface of these phagocytic cells by MHC class II molecules for recognition by CD4+ T cells and the activation of a T helper response. Peptides of antigens expressed in the cytosol of any cell in the body of a mammal may be presented on the surface of that cell by MHC class I molecules for recognition by CD8+ T cells and the activation of a cytotoxic T cell (CTL) response. However, killed intracellular bacteria or components of intracellular bacteria may not invade non-phagocytic cells or may not escape from the phagolysosome of a phagocytic cell into the cytosol, resulting in activation and maturation of phagocytic cells, for example macrophages and dendritic cells. Therefore, the antigens of killed intracellular bacteria or components of intracellular bacteria may not be available for direct MHC I presentation and may not activate a CTL response. The ability of intracellular bacteria to produce proteins within the phagolysosomes and/or cytosol of the host may be necessary in order to elicit a hilly effective cell-mediated immune response.

Strains of *Listeria monocytogenes* have recently been developed as intracellular delivery vehicles of heterologous proteins providing delivery of antigens to the immune system to induce an immune response to clinical conditions that do not permit injection of the disease-causing agent, such as cancer (U.S. Pat. No. 6,051,237 Paterson; U.S. Pat. No. 6,565,852) and HIV (U.S. Pat. No. 5,830,702, Portnoy & Paterson). As a facultative intracellular bacterium, *L. monocytogenes* elicits both humoral and cell-mediated bacterial antigen-specific immune responses. Following entry of the *Listeria* into a cell of the host organism, the *Listeria* produces *Listeria*-specific proteins that enable it to escape from the phagolysosome of the engulfing host cell into the cytosol of that cell. In the cell, *L. monocytogenes* proliferates, expressing proteins necessary for survival, but also expressing heterologous genes operably linked to *Listeria* promoters. Presentation of peptides of these heterologous proteins on the surface of the engulfing cell by MHC proteins permit the development of a T cell response. Since *L. monocytogenes* is a Gram-positive, food-borne human and animal pathogen responsible for serious infections in immunocompromised individuals and pregnant women, strains of these bacteria must be attenuated in a manner that reduces toxicity to the host, while maintaining immunogenicity of the vaccine. This toxicity is the result of bacterial invasion of various organs and tissues of the host, such as those of the liver, spleen and central nervous system. It would be beneficial to reduce the risks associated with using *Listeria monocytogenes* as a vaccine without affecting its potency to induce adaptive cell-mediated immunity specific for heterologous encoded antigen related to selected infectious and malignant diseases.

BRIEF SUMMARY OF THE INVENTION

The present invention generally provides attenuated *Listeria*, and *Listeria monocytogenes*, in particular, as well as methods of using those *Listeria* in vaccines. The vaccines are useful in the induction of immune responses and in the treatment and/or prevention of a wide array of diseases including cancer.

In one aspect, the invention provides an isolated *Listeria bacterium* that is attenuated for entry into non-phagocytic cells (e.g., is defective with respect to an internalin, such as internalin B) and which comprises a nucleic acid molecule encoding a non-Listerial antigen. In some embodiments, the *bacterium* is further attenuated for cell-to-cell spread (e.g., is defective with respect to ActA). In some embodiments, the attenuated *Listeria bacterium* belongs to the species *Listeria monocytogenes*, in some embodiments, the attenuated *Listeria bacterium* is a mutant *Listeria* strain. In some embodiments, the *Listeria bacterium* has been attenuated by the binding of antibodies or antibody fragments to the *bacterium*. An immunogenic composition comprising the *Listeria bacterium* is also provided, as is a vaccine comprising both the *bacterium* and a pharmaceutically acceptable carrier and/or an adjuvant. In addition, methods of inducing an immune response in a host to a non-Listerial antigen comprising administering to the host an effective amount of a composition comprising the attenuated *Listeria bacterium* and methods of preventing or treating a disease in a host (such as cancer or an infectious disease), comprising administering to the host an effective amount of a composition comprising the attenuated *Listeria bacterium* are also provided. An isolated professional antigen-presenting cell comprising the attenuated *Listeria bacterium* is also provided.

In another aspect, the invention provides an isolated *Listeria bacterium* that is attenuated both for entry into non-phagocytic cells (e.g., is defective with respect to an internalin, such as internalin B) and for cell-to-cell spread (e.g., is defective with respect to ActA). In some embodiments, the attenuated *Listeria bacterium* is a mutant *Listeria* strain. In some embodiments, the nucleic acid of the *Listeria bacterium* has been modified with a nucleic acid targeting compound so that the *bacterium* is attenuated for cell-to-cell spread. In some embodiments, the attenuated *Listeria bacterium* comprises at least one mutation (such as a deletion mutation) in both the inlB and actA genes. In some embodiments the attenuated *Listeria* is the *Listeria monocytogenes* ΔactAΔinlB strain (alternatively referred to as the *Listeria monocytogenes* actA⁻inlB⁻ strain) deposited with the American Type Culture Collection (ATCC) and identified by accession number PTA-5562, or a mutant of the deposited strain which is defective both with respect to internalin B and ActA. In some embodiments the attenuated *Listeria bacterium* comprises a nucleic acid molecule encoding a non-Listerial antigen. In some embodiments, the attenuated *Listeria bacterium* belongs to the species *Listeria monocytogenes*. An immunogenic composition comprising the attenuated *Listeria* is also provided, as is a vaccine comprising both the attenuated *Listeria* and a pharmaceutically acceptable carrier and/or an adjuvant. In addition, methods of inducing an immune response in a host to a non-Listerial antigen comprising administering to the host an effective amount of a composition comprising the attenuated *Listeria bacterium* are provided. Methods of preventing or treating a disease in a host (such as cancer, Listeriosis, or a disease caused by a non-Listerial pathogen), comprising administering to the host an effective amount of a composition comprising the attenuated *Listeria bacterium* are also provided. A professional antigen-presenting cell comprising the attenuated *Listeria bacterium* is further provided.

In an additional aspect, the invention provides a vaccine comprising (a) a *Listeria bacterium*, wherein the *Listeria bacterium* is attenuated for entry into non-phagocytic cells, and (b) a pharmaceutically acceptable carrier and/or an adjuvant. In some embodiments, the attenuated *Listeria bacterium* is defective with respect to internalin B. In some embodiments, the attenuated *Listeria bacterium* in the vaccine belongs to the species *Listeria monocytogenes*. In some embodiments, the attenuated *Listeria bacterium* is a mutant *Listeria* strain. Methods of inducing an immune response in a host to a non-Listerial antigen comprising administering to the host an effective amount of the vaccine are provided. Methods of preventing or treating a disease in a host, comprising administering to the host an effective amount of the vaccine are also provided.

In a further aspect, the invention provides an isolated professional antigen-presenting cell comprising a *Listeria bacterium*, wherein the *Listeria bacterium* is attenuated for entry into non-phagocytic cells (e.g., is defective with respect to internalin, such as internalin B). In some embodiments, the *bacterium* is further attenuated for cell-to-cell spread (e.g., is defective with respect to ActA). In some embodiments, the attenuated *Listeria bacterium* in the professional antigen-presenting cell is a mutant *Listeria* strain. In some embodiments, the *Listeria bacterium* belongs to the species *Listeria monocytogenes*. The invention also provides a method of inducing an immune response in a host to an antigen comprising administering to the host an effective amount of the professional antigen-presenting cell, wherein the attenuated *Listeria bacterium* comprises a nucleic acid encoding an antigen. In still another aspect, the invention provides a method of preventing or treating a disease in a host, comprising administering to the host an effective amount of the professional antigen-presenting cell.

In another aspect, the invention provides a method of inducing MHC class I antigen presentation or MHC class II antigen presentation on an antigen-presenting cell (in vivo or in vitro), comprising contacting an attenuated *Listeria bacterium* with an antigen-presenting cell, wherein the attenuated *Listeria bacterium* is attenuated for entry into non-phagocytic cells and comprises a nucleic acid molecule encoding a non-Listerial antigen comprising an MHC class I epitope or an MHC class II epitope.

In still another aspect, the invention provides a method of inducing an immune response in a host to an antigen, comprising the following steps: (a) contacting an attenuated *Listeria bacterium* with an antigen-presenting cell (e.g., an antigen-presenting cell from the host), wherein the attenuated *Listeria bacterium* is attenuated for entry into non-phagocytic cells and comprises a nucleic acid molecule encoding the antigen; and (b) administering the antigen-presenting cell to the host.

In another aspect, the present invention provides a method of preventing or treating disease (such as cancer) in a host, comprising administering to the host a vaccine comprising a mutant *Listeria* strain, wherein the mutant *Listeria* strain is attenuated for entry into non-phagocytic cells relative to a non-mutant *Listeria* strain, but retains an ability to enter phagocytic cells.

In another aspect, the invention provides a method of inducing an immune response in a host to an antigen comprising administering to the host an effective amount of a composition comprising a mutant *Listeria* strain, wherein the mutant *Listeria* strain is attenuated for entry into non-phagocytic cells relative to a non-mutant *Listeria* strain, but retains an ability to enter phagocytic cells, and comprises a nucleic acid molecule encoding the antigen.

In yet another aspect, the invention provides a method of inducing MHC class I antigen presentation or MHC class II antigen presentation on an antigen-presenting cell comprising contacting a mutant *Listeria* strain with an antigen-presenting cell, wherein the mutant *Listeria* strain is attenuated for entry into non-phagocytic cells relative to a non-mutant *Listeria* strain, but retains an ability to enter phagocytic cells, and comprises a heterologous nucleic acid molecule encoding an antigen comprising an MHC class I epitope or an MHC class II epitope, respectively.

In another aspect, the invention provides a method of inducing an immune response in a host to an antigen comprising, the following steps: (a) contacting a mutant *Listeria* strain with an antigen-presenting cell from the host, under suitable conditions and for a time sufficient to load the antigen-presenting cells, wherein the mutant *Listeria* strain is attenuated for entry into non-phagocytic cells relative to a non-mutant *Listeria* strain, but retains an ability to enter phagocytic cells, and comprises a nucleic acid molecule encoding an antigen; and (b) administering the antigen-presenting cell to the host. In one embodiment, the antigen is a tumor-associated antigen or is derived from a tumor-associated antigen.

In still another aspect, the invention provides methods for decreasing the pathogenicity of a strain of *Listeria* used in a vaccine, comprising modifying the strain so as to decrease the ability of the strain to enter non-phagocytic cells, but substantially retain the ability of the strain to enter phagocytic cells. These methods may include deletion mutations in genes encoding proteins which direct bacterial tropism (invasins) for particular nonphagocytic cells, or alternatively, may include treatment of bacteria with polyclonal or monoclonal antibodies which mask said invasins, and as a result inhibit infection of nonphagocytic cells.

In a further aspect, the invention provides a method of selectively delivering a protein into phagocytic (as opposed to non-phagocytic) cells in a host, comprising administering to the host a composition comprising a mutant *Listeria* strain that is attenuated for entry into non-phagocytic cells relative to a non-mutant *Listeria* strain, but substantially retains an ability to enter phagocytic cells, wherein the genome of the mutant *Listeria* strain expressing the protein comprises at least one mutation in at least one gene encoding an invasin (alternatively termed an "invasion protein"), such as an internalin.

In other aspects, the invention provides methods of making vaccines. For instance, the invention provides a method of making a vaccine comprising contacting a mutant *Listeria* strain with an antigen-presenting cell in vitro or ex vivo, under suitable conditions and for a time sufficient to load the antigen-presenting cells wherein the mutant *Listeria* strain is attenuated for entry into non-phagocytic cells relative to a non-mutant *Listeria* strain, but retains an ability to enter phagocytic cells, and comprises a nucleic acid molecule encoding an antigen.

In some embodiments of each of the aforementioned aspects, the mutant strain of *Listeria* is a mutant strain of *Listeria monocytogenes* that is defective with respect to internalin B and/or comprises at least one mutation in the gene encoding internalin B (inlB), and/or in an element regulating its expression. In still further embodiments of each of the aforementioned aspects, the mutant strain is defective with respect to both internalin B and actA and/or comprises at least one mutation in both the inlB gene and the actA gene, and/or in an element regulating their expression.

In addition, the present invention provides a variety of compositions and strains useful in the aforementioned methods, as well as other uses. For instance, in a still further aspect, the invention provides a pharmaceutical composition comprising a mutant *Listeria* strain and a pharmaceutically acceptable carrier, wherein the mutant *Listeria* strain is attenuated for entry into non-phagocytic cells relative to a non-mutant *Listeria* strain, but retains an ability to enter phagocytic cells. In one embodiment, the genome of the mutant strain comprises at least one mutation in at least one gene encoding an invasin (i.e., an invasion protein), such as an internalin, and/or in an element regulating its expression.

In another aspect, the invention provides an immunogenic composition comprising a mutant *Listeria* strain, wherein the mutant *Listeria* strain is attenuated for entry into non-phagocytic cells relative to a non-mutant *Listeria* strain, but retains an ability to enter phagocytic cells, and comprises a heterologous nucleic acid molecule encoding an antigen.

In another aspect, the invention provides a vaccine comprising a mutant *Listeria* strain, wherein the mutant *Listeria* strain is attenuated for entry into non-phagocytic cells relative to a non-mutant *Listeria* strain, but retains an ability to enter phagocytic cells.

In still another aspect, the invention provides a professional antigen-presenting cell, such as a dendritic cell, comprising a mutant *Listeria* strain, wherein the mutant *Listeria* strain is attenuated for entry into non-phagocytic cells relative to a non-mutant *Listeria* strain, but retains an ability to enter phagocytic cells.

In some embodiments of each of the aforementioned aspects, the mutant strain of *Listeria* is a mutant strain of *Listeria monocytogenes*.

In some embodiments of each of the aforementioned aspects, the mutant strain of *Listeria* is defective with respect to internalin B. In some embodiments of each of the aforementioned aspects, the genome of the mutant strain of *Listeria* that is defective with respect to internalin B comprises at least one mutation in the gene encoding internalin B (inlB), and/or in an element regulating its expression. In other embodiments, inlB is deleted from the genome of the mutant *Listeria* strain.

In still further embodiments of each of the aforementioned aspects, the mutant strain is defective with respect to both internalin B and ActA. In some embodiments, the mutant strains comprise at least one mutation in both the inlB gene (and/or an element regulating expression of the inlB gene) and the actA gene (and/or in an element regulating expression of the actA gene).

In an additional aspect, the present invention provides a method of preventing or treating disease (such as cancer) in a host, comprising administering to the host a vaccine comprising a mutant *Listeria* strain, wherein the mutant *Listeria* strain is defective with respect to internalin B.

In another aspect, the invention provides a method of inducing an immune response in a host to an antigen comprising administering to the host an effective amount of a composition comprising a mutant *Listeria* strain, wherein the mutant *Listeria* strain is defective with respect to internalin B and comprises a nucleic acid molecule encoding the antigen.

In another aspect, the invention provides a method of inducing MHC class I antigen presentation or MHC class II antigen presentation on an antigen-presenting cell (in vitro or in vivo), comprising contacting a mutant *Listeria* strain with an antigen-presenting cell, wherein the mutant *Listeria* strain is defective with respect to internalin B and comprises a heterologous nucleic, acid molecule encoding an antigen comprising an MHC class I epitope or an MHC class II epitope, respectively.

In still another aspect, the invention provides a method of inducing an immune response in a host to an antigen comprising, the following steps: (a) contacting a mutant Listeria strain with an antigen-presenting cell from the host, under suitable conditions and for a time sufficient to load the antigen-presenting cells, wherein the mutant Listeria strain is defective with respect to internalin B, and comprises a nucleic acid molecule encoding an antigen; and (b) administering the antigen-presenting cell to the host. In one embodiment, the antigen is a tumor-associated antigen or is derived from a tumor-associated antigen.

In still another aspect, the invention provides a method of decreasing the pathogenicity of a strain of Listeria used in a vaccine, comprising modifying the strain of Listeria so that it is defective with respect to internalin B.

In other aspects, the invention provides methods of making vaccines. For instance, the invention provides a method of making a vaccine comprising contacting a mutant Listeria strain with an antigen-presenting cell under suitable conditions and for a time sufficient to load the antigen-presenting cells, wherein the mutant Listeria strain is defective with respect to internalin B.

In addition, the present invention provides a variety of compositions and strains useful in the aforementioned methods, as well as other uses. For instance, in a still further aspect, the invention provides a pharmaceutical composition comprising a mutant Listeria strain and a pharmaceutically acceptable carrier, wherein the mutant Listeria strain is defective with respect to internalin B. In one embodiment, the genome of the mutant strain comprises at least one mutation in inlB, or in an element regulating its expression.

In another aspect, the invention provides an immunogenic composition comprising a mutant Listeria strain, wherein the mutant Listeria strain is defective with respect to internalin B, and comprises a heterologous nucleic acid molecule encoding an antigen.

In another aspect, the invention provides a vaccine comprising a mutant Listeria strain, wherein the mutant Listeria strain is defective with respect to internalin B.

In still another aspect, the invention provides a professional antigen-presenting cell, such as a dendritic cell, comprising a mutant Listeria strain, wherein the mutant Listeria strain is defective with respect to internalin B.

In some embodiments of each of the aforementioned aspects, the mutant strain of Listeria is a mutant strain of Listeria monocytogenes.

In some embodiments of each of the aforementioned aspects, the genome of the mutant strain of Listeria that is defective with respect to internal in B comprises at least one mutation in the gene encoding internalin B (inlB), and/or in an element regulating its expression. In other embodiments, inlB is deleted from the genome of the mutant Listeria strain.

In still further embodiments of each of the aforementioned aspects, the mutant strain is defective with respect to both internalin B and ActA. In some embodiments, the mutant strains comprise at least one mutation in both the inlB gene (and/or an element regulating expression of the inlB gene) and the actA gene (and/or in an element regulating expression of the actA gene).

In an additional aspect, the invention provides a strain of Listeria monocytogenes that is defective with respect to both an internalin, such as internalin B, and ActA. In one aspect, the invention provides a strain of Listeria monocytogenes that is defective with respect to both internalin B and ActA. In some embodiments, both the inlB gene the actA gene have been mutated. In one embodiment, both the inlB gene and the actA gene have been deleted. In one embodiment, the strain is the Listeria monocytogenes ΔactAΔinlB double mutant (alternatively termed a Listeria monocylogenes actA⁻inlB⁻ double mutant) deposited with the American Type Culture Collection (ATCC) on Oct. 3, 2003, and designated with accession number PTA-5562. In another embodiment, the strain is a mutant of the strain designated as PTA-5562, where the mutant is attenuated for entry into non-phagocytic cells relative to wild-type Listeria monocytogenes.

Cultures, immunogenic compositions, and pharmaceutical compositions including vaccines that comprise any of the aforementioned strains are also provided. The use of these particular strains in any and all of the aforementioned methods is also provided.

DRAWINGS

FIGS. 1A-1C show the target cell populations following injection into mice vaccinated with the indicated Listeria strains or vehicle control. Reduced levels of antigen-specific target cells relative to non-specific target cells indicate in vivo cytotoxicity of T cells in response to the vaccination. FIG. 1A shows in vivo cytotoxicity in mice vaccinated IV or IM with the ΔactA mutant or the ΔactAΔinlB double mutant. FIG. 1B shows in vivo cytotoxicity in mice vaccinated IV with the ΔactA mutant or the ΔactAΔinlB double mutant. FIG. 1C shows in vivo cytotoxicity in mice vaccinated IV with the ΔactAΔinlB mutant.

Figure 11A:
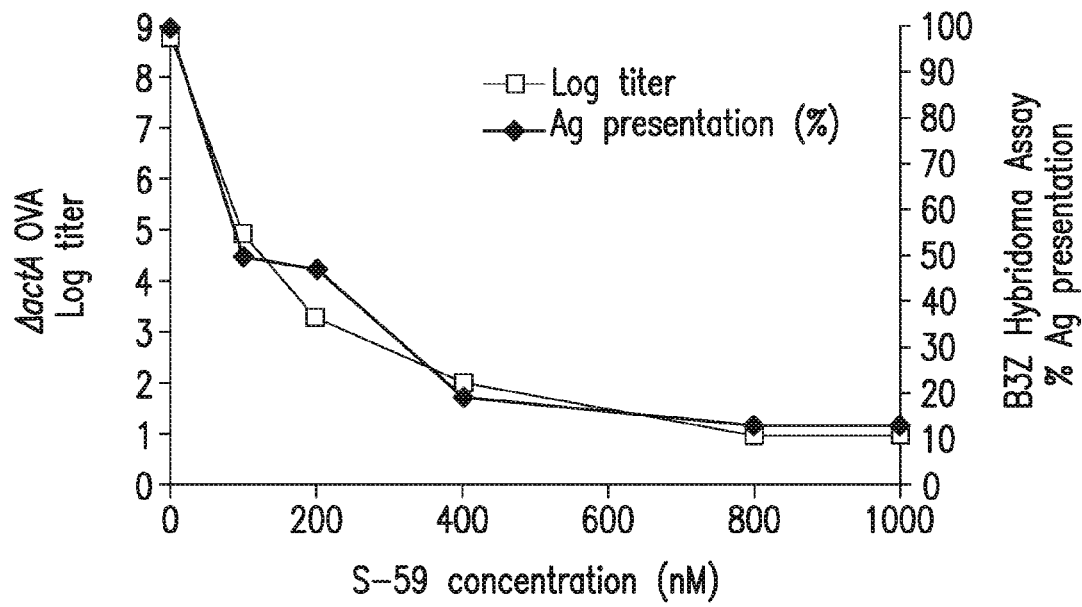

FIG. 11A shows the attenuation of DP-L4029 (ΔactA) Listeria strain containing OVA antigen as a function of psoralen S-59 concentration along with the measurement of OVA antigen presentation to a dendritic cell line. The bacterial log titer and % of antigen presentation relative to untreated (linear scale, 1 Listeria per DC 2.4 cell) are plotted vs. nM S-59 (dosed with 0.5 J/cm$^2$UVA, washed Listeria once, dosed again with 5.5 J/cm$^2$ UVA).

Figure 11B:
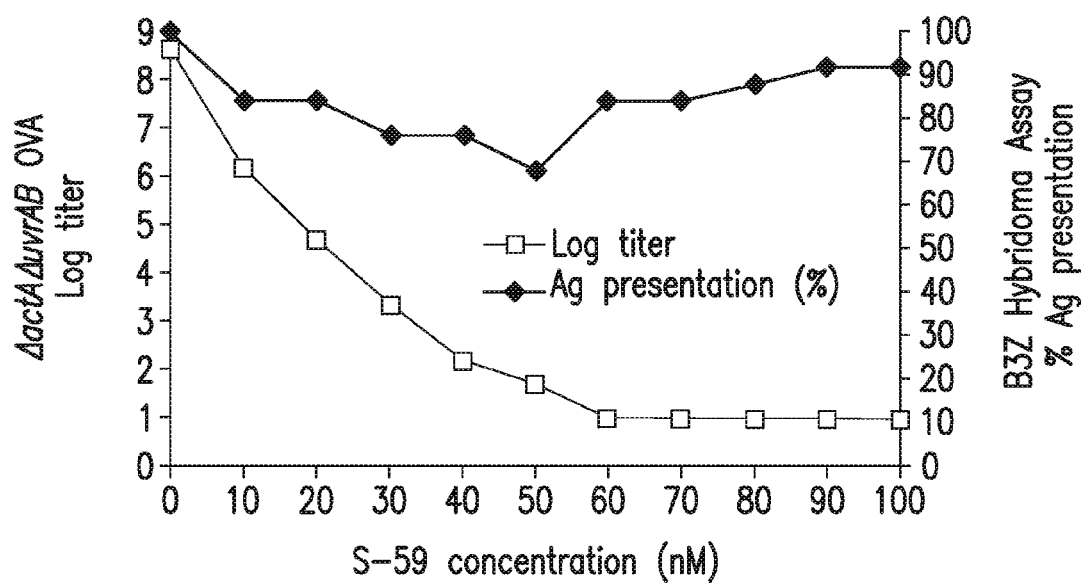

FIG. 11B shows the attenuation of DP-L4029 ΔuvrAB Listeria strain containing OVA antigen as a function of psoralen S-59 concentration along with the measurement of OVA antigen presentation to a dendritic cell line. The bacterial log titer and % of antigen presentation relative to untreated (linear scale, 1 Listeria per DC 2.4 cell) are plotted vs. nM S-59 (dosed with 0.5 J/cm$^2$ UVA, washed Listeria once, dosed again with 5.5 J/cm$^2$ UVA).

Figure 11C:
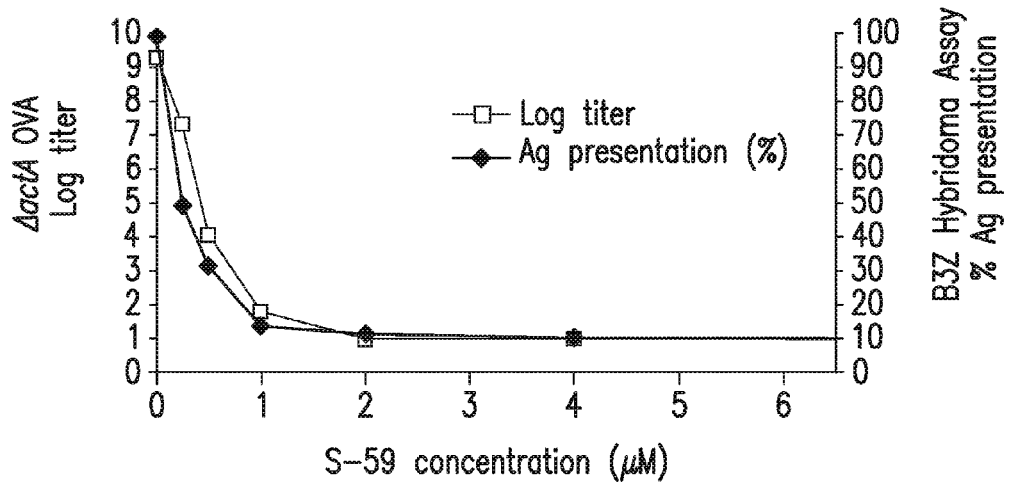

FIG. 11C shows the attenuation of DP-L4029 (ΔuvrAB) Listeria strain containing OVA antigen as a function of psoralen S-59 concentration along with the measurement of OVA antigen presentation to a dendritic cell line.

Figure 11D:
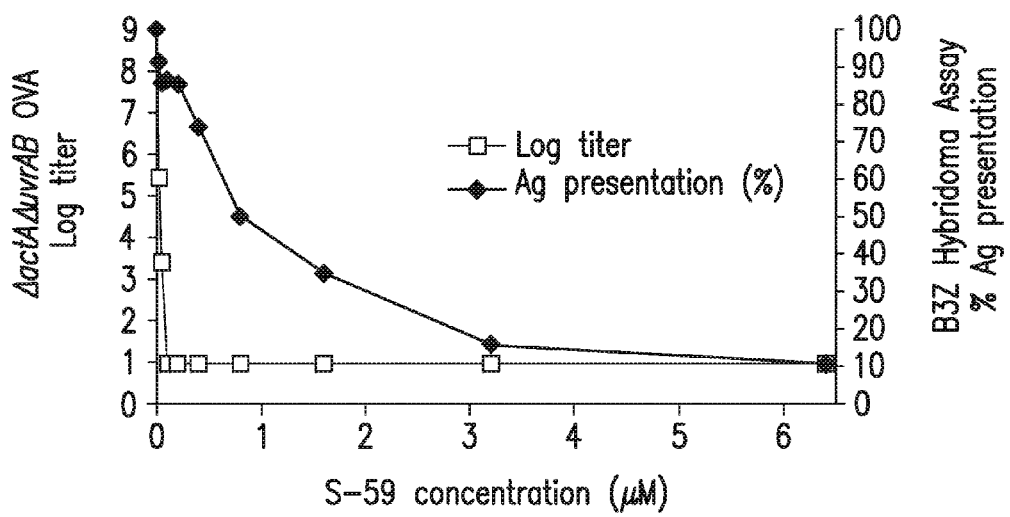

FIG. 11D shows the attenuation of DP L4029 ΔuvrAB (ΔactAΔuvrAB) Listeria strain containing OVA antigen as a function of psoralen S-59 concentration along with the measurement of OVA antigen presentation to a dendritic cell line.

Figure 12A:
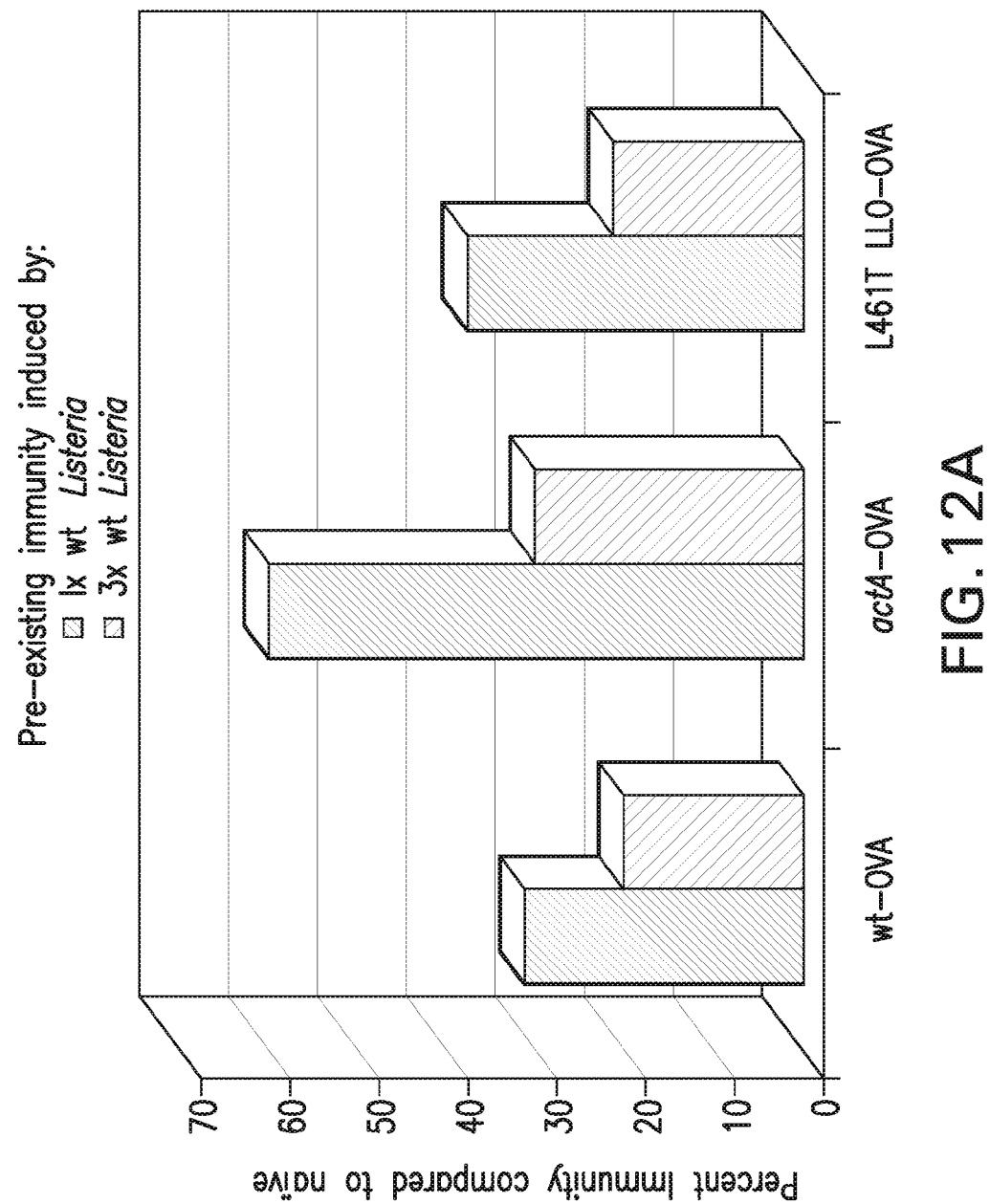

FIG. 12A shows the induction of OVA specific T cell response in the presence of anti-Listeria immunity.

Figure 12B:
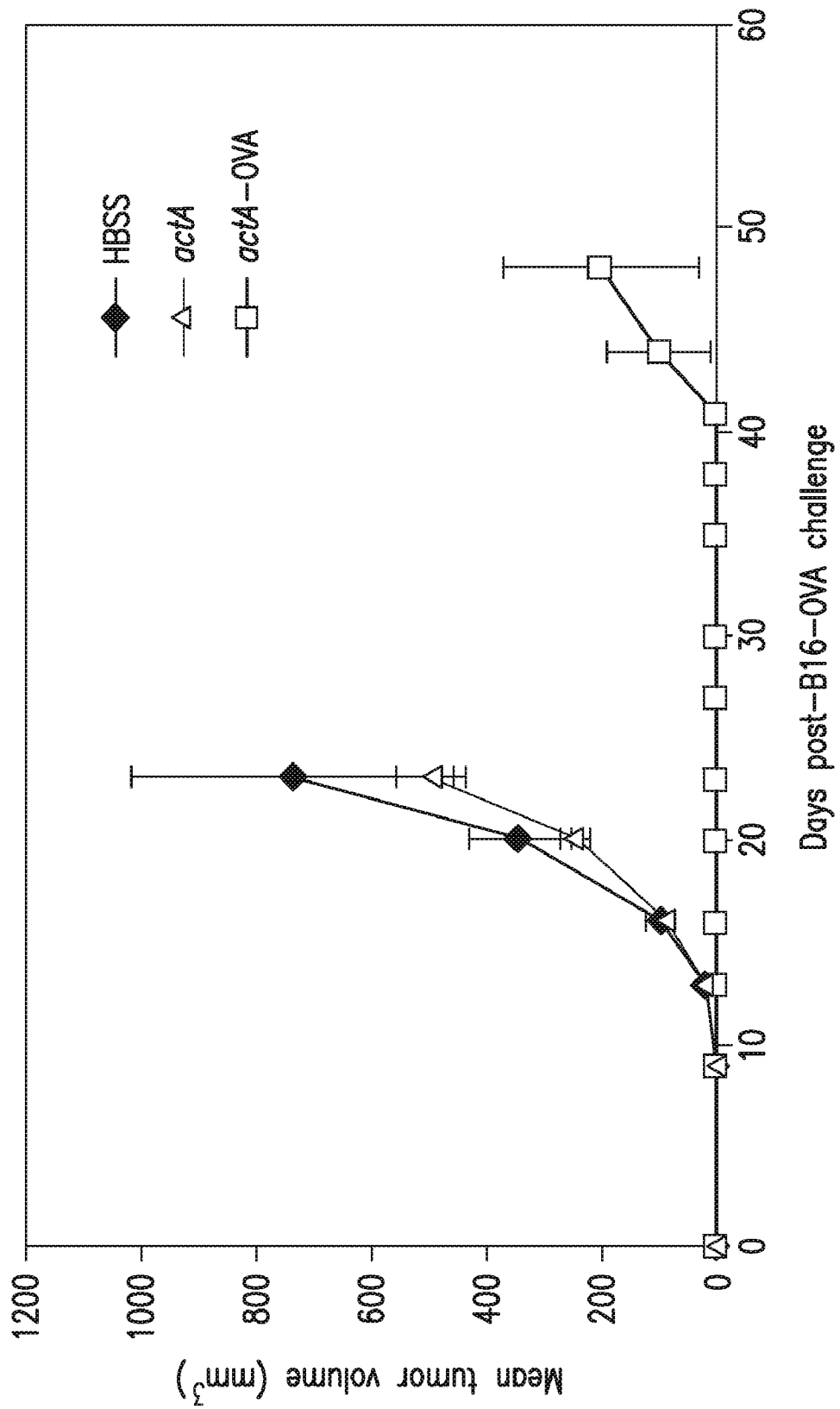

FIG. 12B shows that effective anti-tumor immune response is stimulated in the presence of Listeria-specific immunity.

Figure 12C:
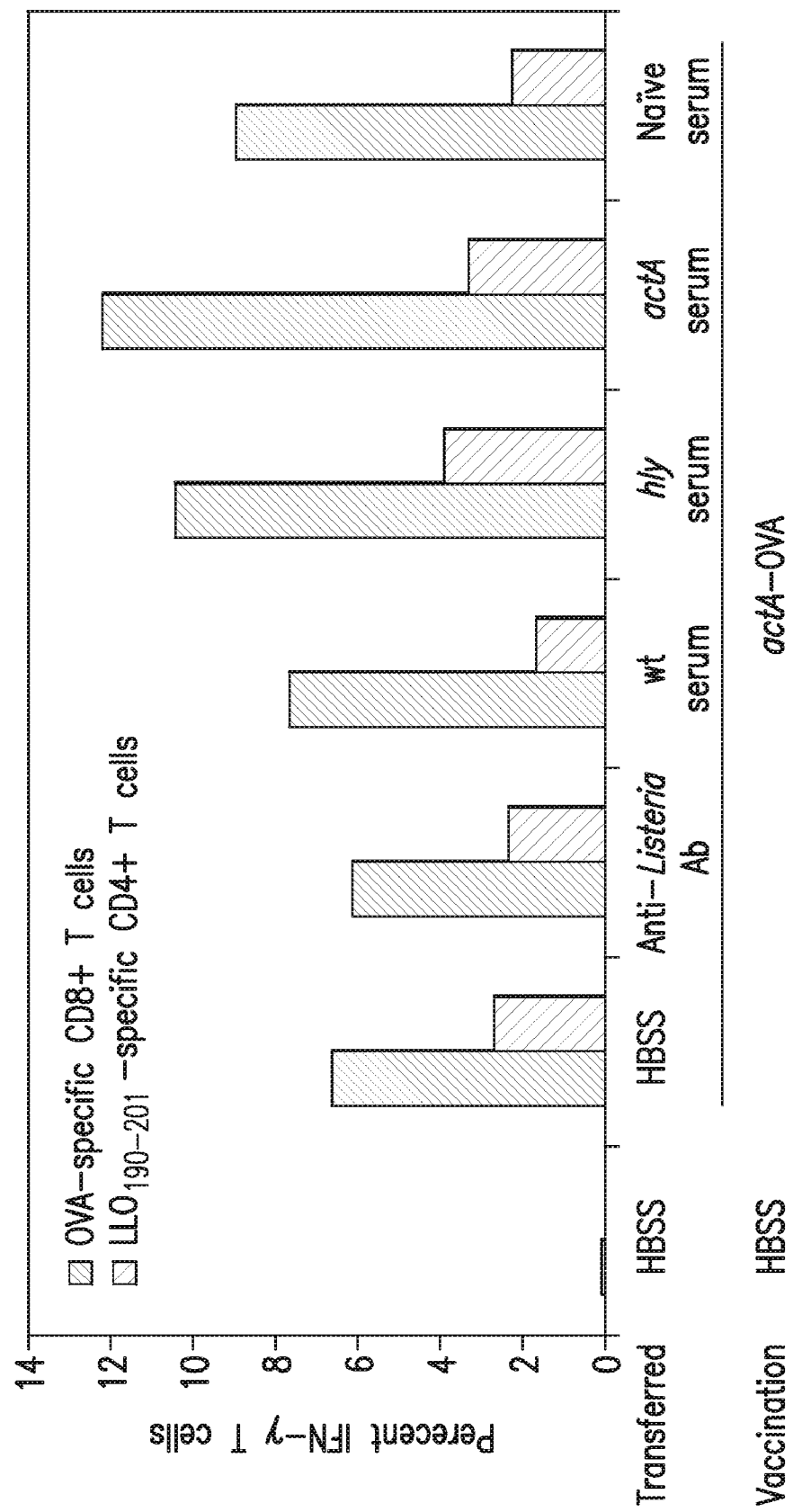

FIG. 12C shows that transfer of Listeria immune serum does not prevent priming of OVA-specific CD8+ cells.

DETAILED DESCRIPTION OF THE INVENTION

I. Introduction

The present invention provides Listeria that are attenuated for entry into non-phagocytic cells (for instance, mutant strains of Listeria that are defective with respect to internalins, such as internalin B.) In some embodiments, the attenuated Listeria are further attenuated for cell-to-spread. In some embodiments, the toxicity of the recombinant Listeria has been greatly diminished by the modifications made to the strain, and yet, the immunogenicity of the strain has been sufficiently retained. Thus, for the first time, the immunogenicity of the attenuated Listeria has been successfully segregated from the toxicity of the Listeria. The present invention provides pharmaceutical compositions, immunogenic compositions, and vaccines comprising the attenuated Listeria, and the use of these attenuated Listeria and Listeria-containing compositions to induce immune responses, including therapeutically effective immune responses in a host. The vaccines and methods can be used either for the prevention of infectious disease caused by Listeria or to deliver a heterologous antigen, such as a tumor-associated antigen or an antigen derived from a non-Listerial pathogen.

Figure 1A:
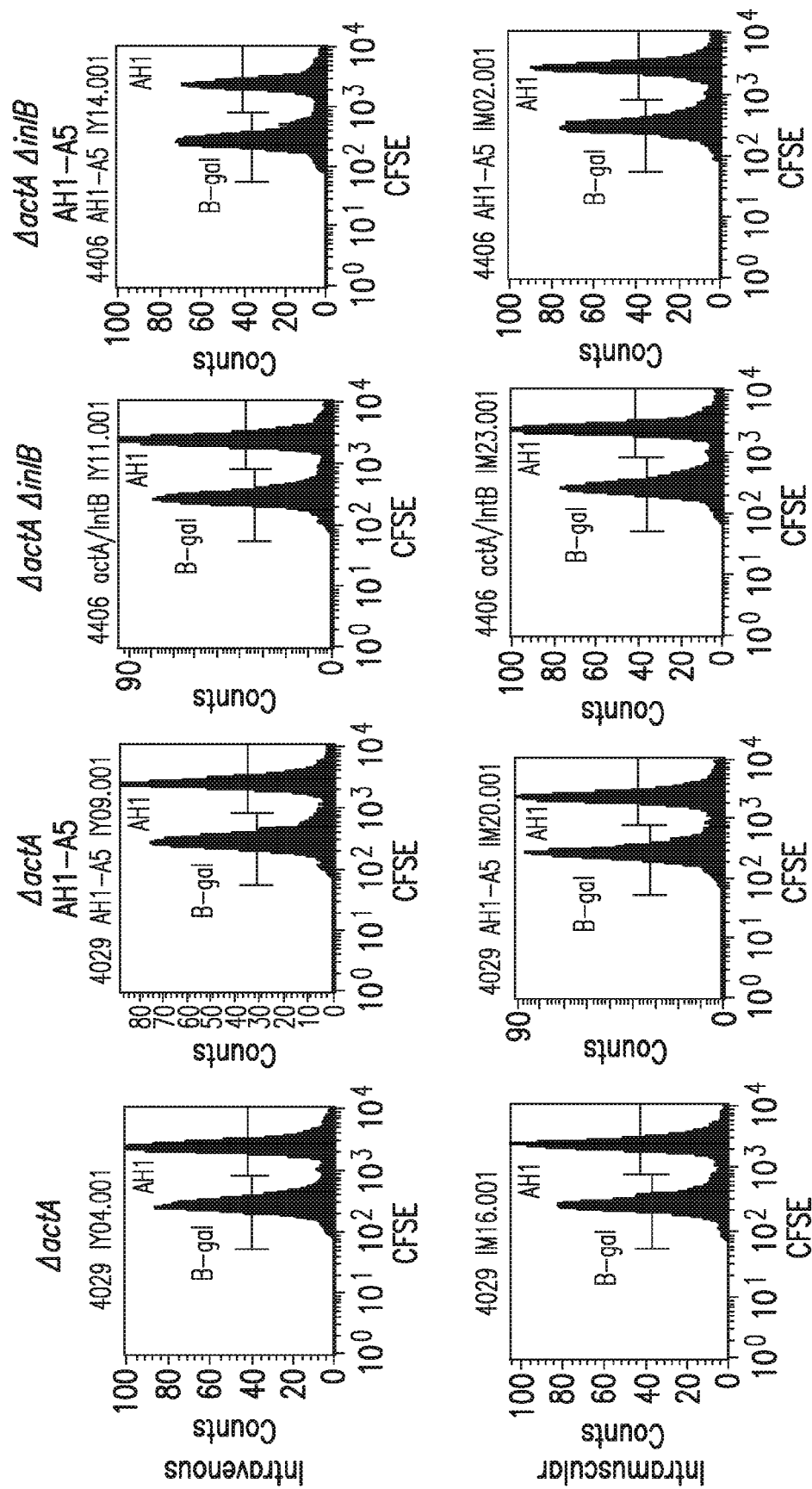
Figure 1B:
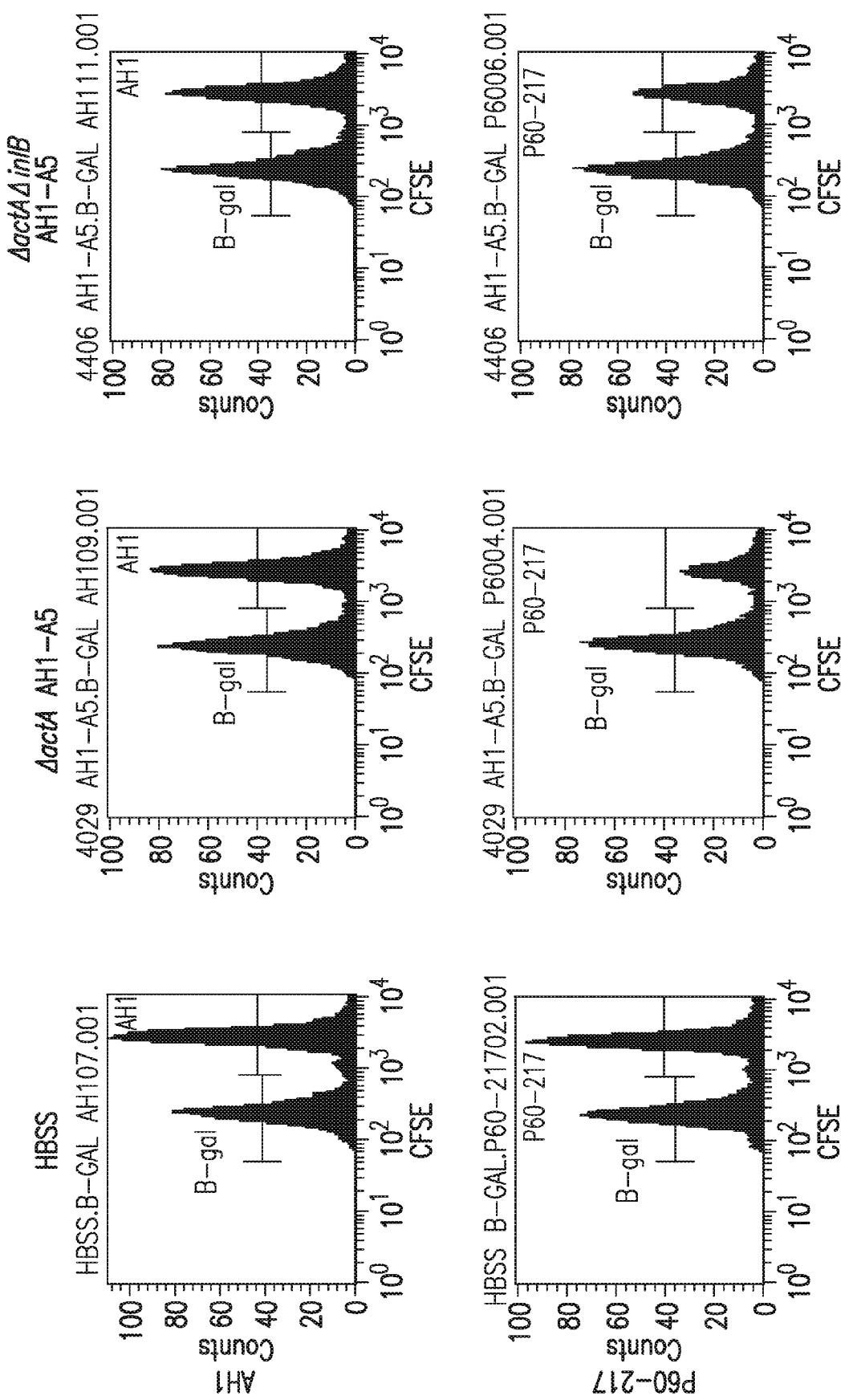
Figure 1C:
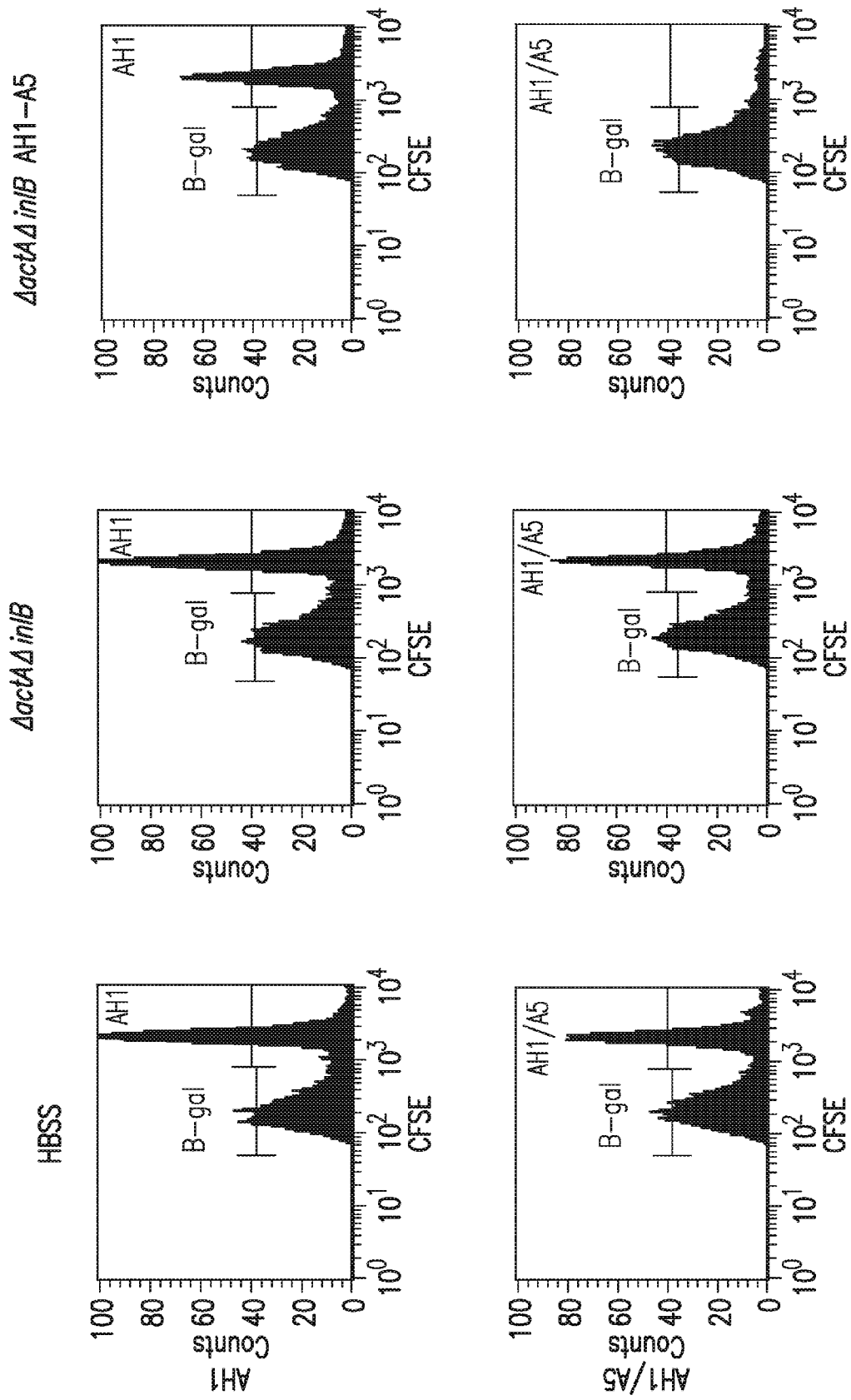
Figure 2A:
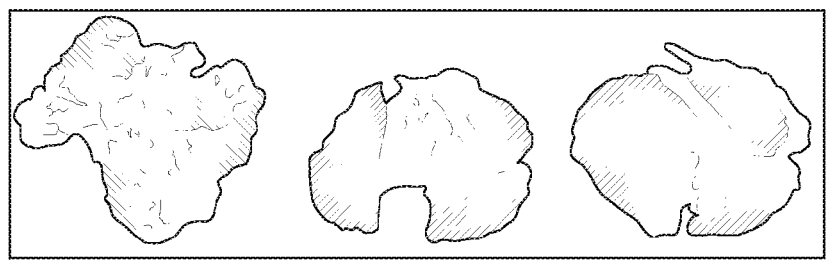
FIGS. 2A-2C show the lungs of mice with established CT26 lung tumors given a therapeutic vaccination with mutant Listeria strains or a control (FIG. 2A) Lung metastases are visible as spots on the lung. The survival of mice from two additional studies is plotted in FIGS. 2B-C.
Figure 2A:
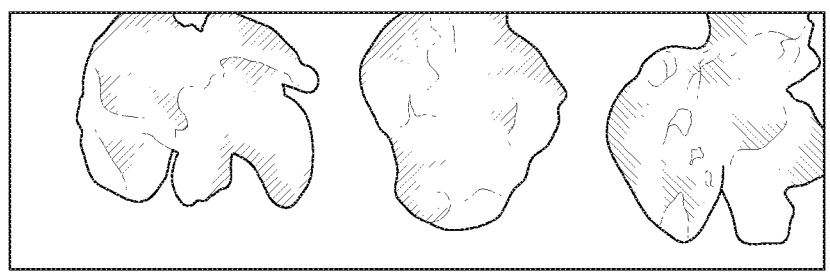
Figure 2A:
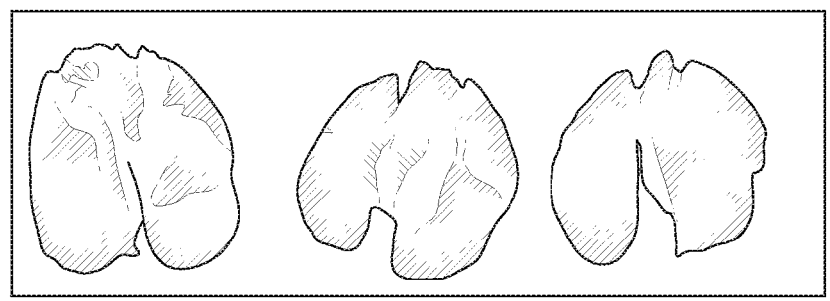
Figure 2A:
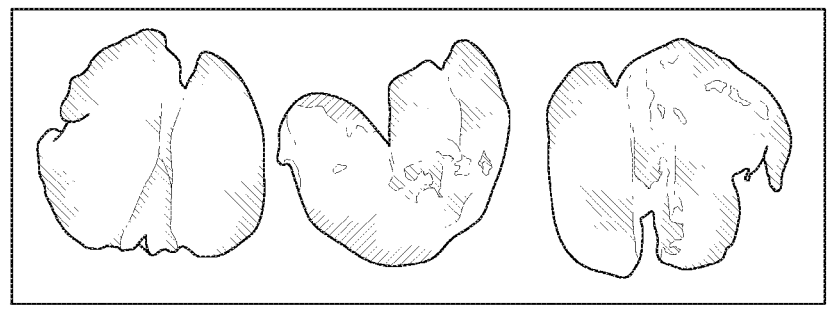

In particular, the present invention provides attenuated strains of Listeria monocytogenes in which the inlB gene has been deleted (i.e., a strain attenuated for entry into non-phagocytic cells, for example, hepatocytes via the c-met receptor) or both the actA gene and the inlB genes have been deleted (i.e., a strain attenuated for both entry into non-phagocytic cells and cell-to-cell spread). The ΔactAΔinlB strain has been determined to be approximately 1,000-fold less virulent than wild-type Listeria monocytogenes (see Example 2 and Table 1, below). The attenuation of the ΔactAΔinlB Listeria strain and the ΔinlB Listeria strain for entry into non-phagocytic human cells has been confirmed (Example 9, below, and FIG. 9). Vaccination with ΔinlB and ΔactAΔinlB Listeria strains expressing heterologous antigens has been shown to result in the production of antigen-specific T-cells (see Examples 5-7, below, and FIGS. 3A, 3B, and 4-6). In addition, vaccination with the ΔactAΔinlB Listeria strain expressing a heterologous antigen has also now been shown to induce an effective robust cytotoxic response to antigen-specific target cells in vivo (see Example 3, below, and FIG. 1). Furthermore, therapeutic vaccination with the ΔactAΔinlB Listeria strain expressing a heterologous antigen has been shown to be effective in reducing the number of lung metastases and in increasing survival rates in a colorectal cancer mouse model (see Example 4, below, and FIGS. 2A-C). Additionally, clearance of an ΔactAΔinlB Listeria strain from the liver and spleen has been shown to be much more rapid than that of wild-type Listeria, the ΔactA Listeria strain, or the ΔinlB Listeria strain (see Example 8, below, and FIGS. 7-8). That is, the combination of the actA and inlB deletion mutations together are synergistic, resulting in rapid liver clearance from animals given high IV does of bacteria.

Accordingly, the invention provides a Listeria bacterium that is attenuated for entry into non-phagocytic cells (e.g., is defective with respect to an internalin, such as internalin B) and Which comprises a nucleic acid molecule encoding a non-Listerial antigen. In some embodiments, the bacterium is further attenuated for cell-to-cell spread (e.g., is defective with respect to ActA). In some embodiments, the attenuated Listeria bacterium belongs to the species Listeria monocytogenes. In some embodiments, the attenuated Listeria bacterium is a mutant Listeria strain. An immunogenic composition comprising the Listeria bacterium is also provided, as is a vaccine comprising both the bacterium and a pharmaceutically acceptable carrier and/or an adjuvant. In addition, methods of inducing an immune response in a host to a non-Listerial antigen comprising administering to the host an effective amount of a composition comprising the attenuated Listeria bacterium and methods of preventing or treating a disease in a host (such as cancer or an infectious disease), comprising administering to the host an effective amount of a composition comprising the attenuated Listeria bacterium are also provided. A professional antigen-presenting cell comprising the attenuated Listeria bacterium is also provided.

The invention also provides a Listeria bacterium that is attenuated both for entry into non-phagocytic cells (e.g., is defective with respect to an internalin, such as internalin B) and for cell-to-cell spread (e.g., is defective with respect to ActA). In some embodiments, the attenuated Listeria bacterium is a mutant Listeria strain. In some embodiments, the attenuated Listeria bacterium comprises at least one mutation (such as a deletion mutation) in both the inlB and actA genes. In some embodiments the attenuated Listeria is the Listeria monocytogenes ΔactAΔinlB strain deposited with the American Type Culture Collection (ATCC) and identified by accession number PTA-5562, or a mutant of the deposited strain which is defective both with respect to internalin B and ActA. In some embodiments the attenuated Listeria bacterium comprises a nucleic acid molecule encoding a non-Listerial antigen. In some embodiments, the attenuated Listeria bacterium belongs to the species Listeria monocytogenes. An immunogenic composition comprising the attenuated Listeria is also provided, as is a vaccine comprising both the attenuated Listeria and a pharmaceutically acceptable carrier and/or an adjuvant. In addition, methods of inducing an immune response in a host to a non-Listerial antigen comprising administering to the host an effective amount of a composition comprising the attenuated Listeria bacterium are provided. Methods of preventing or treating a disease in a host (such as cancer, Listeriosis, or a disease caused by a non-Listerial pathogen), comprising administering to the host an effective amount of a composition comprising the attenuated *Listeria bacterium* are also provided. A professional antigen-presenting cell comprising the attenuated *Listeria bacterium* is further provided.

The invention further provides a vaccine comprising (a) an attenuated *Listeria bacterium*, wherein the attenuated *Listeria bacterium* is attenuated for entry into non-phagocytic cells, and (b) a pharmaceutically acceptable carrier and/or an adjuvant. In some embodiments, the attenuated *Listeria bacterium* is defective with respect to internalin B. In some embodiments, the attenuated *Listeria bacterium* in the vaccine belongs to the species *Listeria monocytogenes*. In some embodiments, the attenuated *Listeria bacterium* is a mutant *Listeria* strain. Methods of inducing an immune response in a host to a non-Listerial antigen comprising administering to the host an effective amount of the vaccine are provided. Methods of preventing or treating a disease in a host, comprising administering to the host an effective amount of the vaccine are also provided.

In addition, the invention provides a professional antigen-presenting cell comprising an attenuated *Listeria bacterium*, wherein the attenuated *Listeria bacterium* is attenuated for entry into non-phagocytic cells (e.g., is defective with respect to internalin, such as internalin B). In some embodiments, the *bacterium* is further attenuated for cell-to-cell spread (e.g., is defective with respect to ActA). In some embodiments, the attenuated *Listeria bacterium* in the professional antigen-presenting cell is a mutant *Listeria* strain. In some embodiments, the *Listeria bacterium* belongs to the species *Listeria monocytogenes*. The invention also provides a method of inducing an immune response in a host to an antigen comprising administering to the host an effective amount of the professional antigen-presenting cell, wherein the attenuated *Listeria bacterium* comprises a nucleic acid encoding an antigen. In still another aspect, the invention provides a method of preventing or treating a disease in a host, comprising administering to the host an effective amount of the professional antigen-presenting cell.

The invention also provides a method of inducing MHC class I antigen presentation or MHC class II antigen presentation on an antigen-presenting cell (either in vitro or in vivo), comprising contacting an attenuated *Listeria bacterium* with an antigen-presenting cell, wherein the attenuated *Listeria bacterium* is attenuated for entry into non-phagocytic cells and comprises a nucleic acid molecule encoding a non-Listerial antigen comprising an MHC class I epitope or an MHC class II epitope.

Additionally, the invention provides a method of inducing an immune response in a host to an antigen, comprising the following steps: (a) contacting an attenuated *Listeria bacterium* with an antigen-presenting cell from the host, wherein the attenuated *Listeria bacterium* is attenuated for entry into non-phagocytic cells and comprises a nucleic acid molecule encoding the antigen; and (b) administering the antigen-presenting cell to the host.

The invention also provides a method of inducing an immune response in a host to an antigen comprising administering to the host an effective amount of a composition comprising a mutant *Listeria* strain, wherein the mutant *Listeria* strain is attenuated for entry into non-phagocytic cells relative to a non-mutant *Listeria* strain, but retains an ability to enter phagocytic cells, and comprises a nucleic acid molecule encoding the antigen. Within the host, the antigen is expressed by the mutant *Listeria* in a manner that induces an immune response.

The present invention provides a method of preventing or treating disease (such as cancer) in a host, comprising administering to the host a vaccine comprising a mutant *Listeria* strain, wherein the mutant *Listeria* strain is attenuated for entry into non-phagocytic cells relative to a non-mutant *Listeria* strain, but retains an ability to enter phagocytic cells.

The invention also provides a method of inducing MHC class I antigen presentation or MHC class II antigen presentation on an antigen-presenting cell comprising contacting a mutant *Listeria* strain with an antigen-presenting cell, wherein the mutant *Listeria* strain is attenuated for entry into non-phagocytic cells relative to a non-mutant *Listeria* strain, but retains an ability to enter phagocytic cells, and comprises a heterologous nucleic acid molecule encoding an antigen comprising an MHC class I epitope or an MHC class II epitope, respectively.

In addition, the invention provides a method of inducing an immune response in a host to an antigen comprising, the following steps: (a) contacting a mutant *Listeria* strain with an antigen-presenting cell from the host, under suitable conditions and for a time sufficient to load the antigen-presenting cells, wherein the mutant *Listeria* strain is attenuated for entry into non-phagocytic cells relative to a non-mutant *Listeria* strain, but retains an ability to enter phagocytic cells, and comprises a nucleic acid molecule encoding an antigen; and (h) administering the antigen-presenting cell to the host. In one embodiment, the antigen is a tumor-associated antigen or is derived from a tumor-associated antigen.

The invention also provides a method of inducing an immune response to an antigen in a host comprising administering to the host an effective amount of a composition comprising a mutant *Listeria* strain, wherein the mutant *Listeria* strain is defective with respect to internalin B, and comprises a nucleic acid molecule encoding the antigen. Within the host, the antigen is expressed by the mutant *Listeria* in a manner that induces an immune response.

The present invention also provides a method of preventing or treating disease (such as cancer) in a host, comprising administering to the host a vaccine comprising a mutant *Listeria* strain, wherein the mutant *Listeria* strain is defective with respect to internalin B.

The invention further provides a method of inducing MHC class I antigen presentation or MHC class II antigen presentation on an antigen-presenting cell comprising contacting a mutant *Listeria* strain with an antigen-presenting cell, wherein the mutant *Listeria* strain is defective with respect to internalin B and comprises a heterologous nucleic acid molecule encoding an antigen comprising an MHC class I epitope or an MHC class II epitope, respectively.

In addition, the invention provides a method of inducing an immune response in a host to an antigen comprising, the following steps: (a) contacting a mutant *Listeria* strain with an antigen-presenting cell from the host, under suitable conditions and for a time sufficient to load the antigen-presenting cells, wherein the mutant *Listeria* strain is defective with respect to internalin B, and comprises a nucleic acid molecule encoding an antigen; and (b) administering the antigen-presenting cell to the host.

The present invention also provides pharmaceutical compositions, immunogenic compositions, and vaccines comprising a mutant *Listeria* strain that is attenuated for entry into non-phagocytic cells relative to a non-mutant strain, but retains an ability to enter phagocytic cells. In some embodiments, the mutant strains of *Listeria* are defective with respect to one or more invasins, such as internalin B. For instance, in some embodiments, the mutant strain of *Listeria* is a mutant strain of *Listeria monocytogenes* that comprises a mutation in one or more genes encoding an internalin protein (such as internalin B), and/or in an element regulating expression of an internalin protein gene (such as the inlB gene). In some embodiments, the strains defective with respect to an internalin protein, such as internalin B, are also defective with respect to a second Listerial protein, such as ActA.

The invention further provides novel strains of *Listeria monocytogenes* that are defective with respect to both internalin B and ActA. For instance, is some embodiments both the inlB gene and the actA gene have been deleted. In one embodiment, the strain is the *Listeria monocytogenes* ΔactAΔinlB double mutant deposited with the American Type Culture Collection (ATCC) on Oct. 3, 2003, and designated with accession number PTA-5562.

II. Attenuated *Listeria*

The attenuated *Listeria* of the present invention have been developed to permit the expression and delivery of one or more antigens to the phagolysosomes and/or cytosol of professional antigen-presenting cells (APCs), such as macrophages, neutrophils and dendritic cells, while reducing entry of the bacteria into non-APCs, such as the cells of organs and non-immune systems. Accordingly, the *Listeria bacterium* used in the compositions, vaccines, and methods of the invention is attenuated for entry into non-phagocytic cells, relative to *Listeria* without the relevant attenuating modifications, such as wild type *Listeria*.

As used herein, the terms "attenuated *Listeria bacterium*" and "modified *Listeria bacterium*" (or "attenuated *Listeria*" and "modified *Listeria*") are used interchangeably herein to refer to a *Listeria bacterium* (or *Listeria*) that is attenuated for entry into non-phagocytic cells relative to wild type *Listeria*. It is understood that the attenuated *Listeria* (i.e., modified *Listeria*) described herein are either non-naturally occurring *Listeria* or *Listeria* that are naturally occurring, but which have now been isolated and/or are now found in a form in which they do not exist in nature. As used herein, the tenths "non-attenuated *Listeria bacterium*" and "unmodified *Listeria bacterium*" (or "non-attenuated *Listeria*" and "unmodified *Listeria*") relative terms used interchangeably herein to refer to *Listeria bacterium* (or *Listeria*) that does not comprise a particular modification that attenuates another *Listeria bacterium* or *Listeria* for entry into non-phagocytic cells relative to wild type *Listeria*. Accordingly, one example of an unmodified *Listeria* is wild type *Listeria*.

In some embodiments, the attenuated *Listeria bacterium* is a member of a mutant *Listeria* strain, wherein mutations in the genome of the mutant *Listeria* strain render the *Listeria* attenuated for entry into non-phagocytic cells. In some embodiments, the *Listeria bacterium* has been modified through means other than, or in addition to mutation, so that the *Listeria bacterium* is attenuated for entry into non-phagocytic cells (e.g., through antibody binding to the *Listeria*).

In some embodiments, the attenuated *Listeria bacterium* is not only attenuated for entry into non-phagocytic cells, relative to unmodified *Listeria*, such as wild type *Listeria*, but the attenuated *Listeria bacterium* is also attenuated for cell-to-cell spread, relative to the unmodified *Listeria*. In some embodiments, the attenuated *Listeria bacterium* belongs to a mutant *Listeria* strain that comprises one or more genomic mutations that renders the *Listeria* attenuated for cell-to-cell spread. In some embodiments, the attenuated *Listeria bacterium* has been modified through means other than, or in addition to mutation, so that the *Listeria bacterium* is attenuated for cell-to-cell spread (e.g., through S-59/UVA treatment).

The attenuated bacteria belong to the genus *Listeria*. In some embodiments, the attenuated *Listeria* belong to a species selected from the group consisting of *Listeria monocytogenes, Listeria ivanovii, Listeria seeligeri,* or *Listeria innocua*. Furthermore, the invention contemplates the mutation of strains of a variety of *Listeria* species (e.g., a strain that normally expresses internalin B, or its equivalent), especially where those bacteria are normally pathogenic and/or utilize invasins to invade non-phagocytic eukaryotic cells. In one embodiment, the strain of *Listeria* that is mutated is a pathogenic strain of *Listeria*. In another embodiment, the strain of *Listeria* that is mutated produces at least one invasin. In another embodiment, the strain is *Listeria monocytogenes, Listeria ivanovii, Listeria seeligeri,* or *Listeria innocua*. In another embodiment, the mutant strain of *Listeria* is a mutant strain of *Listeria monocytogenes*.

The present invention further provides cultures of the attenuated *Listeria* described herein, such as cultures of the mutant strains.

A. Attenuation for Entry into Non-Phagocytic Cells

Generally, the attenuated *Listeria bacterium* of the present invention is a *Listeria bacterium* comprising one or more modifications so that it is attenuated for entry into non-phagocytic cells ("modified *Listeria bacterium*" or "attenuated *Listeria bacterium*") relative to the same *Listeria bacterium* without the modification(s) that render the *bacterium* attenuated for entry into non-phagocytic cells ("unmodified *Listeria bacterium*" or "non-attenuated *Listeria bacterium*"). A *Listeria bacterium* that is attenuated for entry into non-phagocytic cells is less able to infect at least one type of non-phagocytic cell from the extracellular environment of the non-phagocytic cell than wild type *Listeria* of the same species. In some embodiments, the ability of the attenuated *Listeria bacterium* to enter non-phagocytic cells is reduced by at least about 10%, at least about 25%, at least about 50%, at least about 75%, or at least about 90%, relative to wild type *Listeria*. In some embodiments, the ability of the attenuated *Listeria bacterium* to enter non-phagocytic cells is reduced by at least about 50% relative to wild type *Listeria* of the same species. In other embodiments, the ability of the attenuated *Listeria bacterium* to enter non-phagocytic cells is reduced by at least about 75%.

In some embodiments, the attenuated *Listeria bacterium* belongs to a mutant *Listeria* strain that comprises one or more mutations in its genome that cause the strain to be attenuated for entry into non-phagocytic cells ("mutant" *Listeria* strain) relative to the same *Listeria* strain without the one or more mutations ("non-mutant" *Listeria* strain). The ability of the attenuated *Listeria* strain to enter non-phagocytic cells may be reduced by at least about 10%, at least about 25%, at least about 50%, at least about 75%, or at least about 90%, relative to the unmodified (non-mutant) *Listeria* strain.

It is understood that the attenuated *Listeria*, such as a mutant *Listeria* strain, need not necessarily be attenuated for entry into more than one type of non-phagocytic cell. For instance, the attenuated strain may be attenuated for entry into hepatocytes, but not attenuated for entry into epithelial cells. As another example, the attenuated strain may be attenuated for entry into epithelial cells, but not hepatocytes. It is also understood that attenuation for entry into a non-phagocytic cell of particular modified *Listeria* is a result of mutating a designated gene, for example a deletion mutation; encoding an invasin protein which interacts with a particular cellular receptor, and as a result facilitates infection of a non-phagocytic cell. For example, *Listeria* ΔinlB mutant strains are attenuated for entry into non-phagocytic cells expressing the hepatocyte growth factor receptor (c-met), including hepatocyte cell lines (e.g., HepG2), and primary human hepatocytes.

In some embodiments, even though the *Listeria* (e.g., the mutant *Listeria*) are attenuated for entry into non-phagocytic cells, the *Listeria* are still capable of uptake by phagocytic cells, such as at least dendritic cells and/or macrophages. In one embodiment the ability of the attenuated *Listeria* to enter phagocytic cells is not diminished by the modification made to the strain, such as the mutation of an invasin (i.e. approximately 95% or more of the measured ability of the strain to be taken up by phagocytic cells is maintained post-modification). In other embodiments, the ability of the attenuated *Listeria* to enter phagocytic cells is diminished by no more than about 10%, no more than about 25%, no more than about 50%, or no more than about 75%.

In vitro assays for determining whether or not a *Listeria* bacterium (e.g., a mutant *Listeria* strain) is attenuated for entry into non-phagocytic cells are known to those of ordinary skill in the art. For instance, both Dramsi et al., *Molecular Microbiology* 16:251-261 (1995) and Gaillard et al., *Cell* 65:1127-1141(1991) describe assays for screening the ability of mutant *L. monocytogenes* strains to enter certain cell lines. For instance, to determine whether a *Listeria* bacterium with a particular modification is attenuated for entry into a particular type of non-phagocytic cells, the ability of the attenuated *Listeria* bacterium to enter a particular type of non-phagocytic cell is determined and compared to the ability of the identical *Listeria* bacterium without the modification to enter non-phagocytic cells. Likewise, to determine whether a *Listeria* strain with a particular mutation is attenuated for entry into a particular type of non-phagocytic cells, the ability of the mutant *Listeria* strain to enter a particular type of non-phagocytic cell is determined and compared to the ability of the *Listeria* strain without the mutation to enter non-phagocytic cells.

In some embodiments of the invention, the amount of attenuation in the ability of the *Listeria* bacterium to enter non-phagocytic cells ranges from a two-fold reduction to much greater levels of attenuation. In some embodiments, the attenuation in the ability of the *Listeria* to enter non-phagocytic cells is at least about 0.3 log, about 1 log, about 2 log, about 3 log, about 4 log, about 5 log, or at least about 6 log. In some embodiments, the attenuation is in the range of about 0.3 to >8 log, about 2 to >8 log, about 4 to >8 log, about 6 to >8 log, about 0.3-8 log, also about 0.3-7 log, also about 0.3-6 log, also about 0.3-5 log, also about 0.3-4 log, also about 0.3-3 log, also about 0.3-2 log, also about 0.3-1 log. In some embodiments, the attenuation is in the range of about 1 to >8 log, 1-7 log, 1.6 log, also about 2-6 log, also about 2-5 log, also about 3-5 log.

In some embodiments, the attenuation of the *Listeria* of the present invention can be measured in terms of biological effects of the *Listeria* on a host. The pathogenicity of a *Listeria* strain can be assessed by measurement of the $LD_{50}$ in mice or other vertebrates (Example 2, Table 1). The $LD_{50}$ is the amount, or dosage, of *Listeria* injected into vertebrates necessary to cause death in 50% of the vertebrates. The $LD_{50}$ values can be compared for *Listeria* having a particular modification (e.g., mutation) versus *Listeria* without the particular modification as a measure of the level of attenuation. For example, if the *Listeria* strain without a particular mutation has an $LD_{50}$ of $10^3$ bacteria and the *Listeria* strain having the particular mutation has an $LD_{50}$ of $10^3$ bacteria, the strain has been attenuated so that is $LD_{50}$ is increased 100-fold or by 2 log.

Alternatively, the degree of attenuation of the ability of a *Listeria* bacterium to infect non-phagocytic cells can be assessed much more directly in vitro. The ability of a modified *Listeria* bacterium to infect non-phagocytic cells, such as hepatocytes, can be compared to the ability of non-modified *Listeria* or wild type *Listeria* to infect phagocytic cells. In such an assay, the modified and non-modified *Listeria* are typically added to the non-phagocytic cells in vitro for a limited period of time (for instance, an hour), the cells are then washed with a gentamicin-containing solution to kill any extracellular bacteria, the cells are lysed and then plated to assess titer. Examples of such an assay are provided in Example 9 and Example 10, below.

The degree of attenuation may also be measured qualitatively by other biological effects, such as the extent of tissue pathology or serum liver enzyme levels. Alanine aminotransferase (ALT), aspartate aminotransferase (AST), albumin and bilirubin levels in the serum are determined at a clinical laboratory for mice injected with *Listeria* of the present invention. Comparisons of these effects in mice or other vertebrates can be made for *Listeria* with and without particular modifications/mutations as a way to assess the attenuation of the *Listeria*. Attenuation of the *Listeria* relating to the present invention may also be measured by tissue pathology. The amount of *Listeria* that can be recovered from various tissues of an infected vertebrate, such as the liver, spleen and nervous system, can also be used as a measure of the level of attenuation by comparing these values in vertebrates injected with mutant versus non-mutant *Listeria*. For instance, the amount of *Listeria* that can be recovered from infected tissues such as liver or spleen as a function of time can be used as a measure of attenuation by comparing these values in mice injected with mutant vs. non-mutant *Listeria*.

Accordingly, the attenuation of the *Listeria* of the present invention can be measured in terms of bacterial load in particular selected organs in mice known to be targets by wild-type *Listeria*. For example, the attenuation of the *Listeria* of the present invention can be measured by enumerating the colonies (Colony Forming Units; CFU) arising from plating dilutions of liver or spleen homogenates (homogenized in $H_2O+0.2\%$ NP40) on BHI agar media. The liver or spleen cfu can be measured, for example, over a time course following administration of the modified *Listeria* of the present invention via any number of routes, including intravenous, intraperitoneal, intramuscular, and subcutaneous, (See, e.g., Example 8, below.) Additionally, the *Listeria* of the present invention can be measured and compared to a drug-resistant, wild type *Listeria* (or any other selected *Listeria* strain) in the liver and spleen (or any other selected organ) over a over a time course following administration by the competitive index assay, as described.

The degree of attenuation in uptake of the bacteria involved in the vaccines of the present invention by non-phagocytic cells need not be an absolute attenuation in order to provide a safe and effective vaccine. In some embodiments, the degree of attenuation is one that provides for a reduction in toxicity sufficient to prevent or reduce the symptoms of toxicity to levels that are not life threatening.

1. *Listeria* Comprising Mutations that Attenuate the *Listeria* for Entry into Non-Phagocytic Cells In some embodiments, the attenuated *Listeria* comprise one or more mutations that render the *Listeria* defective with respect to one or more invasin (alternatively termed an invasion protein) normally produced by the *Listeria*, such as an internalin. In some embodiments of the invention, the attenuation in the ability of the attenuated *Listeria* to enter non-phagocytic cells is achieved through the use of mutations that affect one or more invasins expressed by the bacteria. In some embodiments, the attenuated *Listeria* bacterium is a member of a mutant *Listeria* strain that is attenuated for entry into non-phagocytic cells.

In one embodiment, the attenuated *Listeria* are defective in the production of one or more invasins. An attenuated *Listeria* bacterium is defective with respect to the production of an invasin if the *bacterium* either produces decreased amounts of a functional version of the invasin or expresses a version of the invasin that is partially or totally nonfunctional, or both. Likewise, a strain of *Listeria* is defective with respect to the production of an invasin if the bacteria of the strain either produce decreased amounts of a functional version of the invasin or express a version of the invasin that is partially or totally nonfunctional, or both.

In some embodiments, the genome of the attenuated *Listeria* comprises one or more mutations in a gene encoding an invasin, such as an internalin. The mutation is optionally a point mutation, an insertion mutation, a termination mutation, a frame shift mutation, or a deletion of part or whole of the gene encoding the invasin. In some embodiments, the gene encoding the invasin (for example, inlB) is deleted.

In some embodiments, the mutation of the gene encoding the invasin is in the coding sequence. In these embodiments, the mutation of the gene encoding the invasin renders the protein less functional as an invasin than the non-mutated sequence. In some embodiments, the mutation of the gene encoding the invasin renders the protein entirely non-functional.

In alternative embodiments, expression of at least one gene encoding an invasin in the mutant strain is inhibited relative to a non-mutant strain. For instance, the genome of the mutant *Listeria* may comprise at least one mutation in a gene encoding an invasin, where the mutation hinders expression. For instance, the mutation may be in one or more of the control sequences (such as the promoter or ribosome binding region) of the genes, so that expression of the invasin gene is decreased or eliminated. Alternatively, the mutant *Listeria* may comprise at least one mutation in a gene other than one encoding an invasin, but which nonetheless results in a diminution of the expression levels of one or more invasins.

Invasins are proteins expressed by *Listeria* that interact with receptors expressed by selected host cells, and as a result, help facilitate penetration of *Listeria* into the host cells. Some invasins are found in the cell wall of *Listeria*. Other invasins are secreted by *Listeria*. Invasins of *Listeria* include, but are not limited to, members of the internalin-related protein family ("internalins"). Internalin proteins typically direct the uptake of *Listeria* by non-phagocytic cells, such as the cells of the liver, spleen or brain.

A number of internalins have been identified in *L. monocytogenes* (Boland, et al., *Clinical Microbiology Reviews,* 2001, 14: 584-640). These internalins include, but are not limited to, InlA, InlB, InlC, InlC2, InlD, InlE, InlF, InlG, and InlH (Dramsi, et al., *Infection and Immunity,* 65: 1615-1625 (1997); Raffelsbauer et al., *Mol. Gen. Genet.* 260:144-158 (1988)). The gene sequences encoding these proteins have been previously reported. For instance, the sequences for both inlA and inlB have been reported in Gaillard et al., *Cell,* 65:1127-1141 (1991) and as GenBank accession number M67471. Genes encoding additional members of the internalin-related protein family are identified in Web Table 2 of the Supplementary Web material of Glaser et al., *Science,* 294: 849-852 (2001), (www.sciencemag.org/cgi/content/full/294/5543/849/DC1), including lmo0327, lmo0331, lmo0514, lmo0610, lmo0732, lmo1136, lmo1289, lmo2396, lmo0171, lmo0333, Imo0801, lmo1290, lmo2026, and lmo2821. (The sequences of each member of the internalin-related protein family can be found in the *L. monocytogenes* strain EGD genome, GenBank Accession no. AL1591824, and/or in the *L. monocytogenes* strain EGD-e genome, GenBank Accession no. NC_003210. Locations of the various internalin-related genes are indicated in Glaser et al.).

In some embodiments the attenuated *Listeria bacterium* are defective with respect to an internalin such as one or more of the internalin proteins listed above or encoded by an internalin gene listed above. In some embodiments, the attenuated *Listeria bacterium* is defective with respect to internalin B, or its equivalent (depending on the species of *Listeria* used). In other embodiments, the attenuated *Listeria bacterium* is defective with respect to internalin A, or its equivalent (depending on the species of *Listeria* used). In other embodiments, the attenuated *Listeria bacterium* is defective with respect to one or more internalins other than internalin A, or its equivalent (depending on the species of *Listeria* used).

For instance, the mutant *Listeria* strain is optionally an *L. monocytogenes* strain which has been modified to be defective in the production of functional internalin B. In still another embodiment, the *L. monocytogenes* has been modified to be defective in the production of an internalin other than internalin A (InlA) (It is understood that the proteins that are the functional equivalents of the above-listed internalins, including internalin B, may be present in species of *Listeria* other than *Listeria monocytogenes*. Accordingly, in some embodiments, the mutant *Listeria* strain has been modified to be defective with respect to the production of a protein that is functionally equivalent to internalin B.)

The mutant *Listeria* strains of the present invention may express less of the wild-type internalin sequence than non-mutant *Listeria* strains. Alternatively, the mutant *Listeria* may express a mutated form of internalin which is non-functional or less functional than that expressed by non-mutant *Listeria*. In still another embodiment, the mutant *Listeria* does not express a particular internalin, such as internalin B, at all because most or all of the gene or sequence encoding the internalin has been deleted.

In one embodiment the genome of the Mutant *Listeria* comprises an attenuating mutation in one or more internalin genes (including, but not necessarily limited to, those listed above). In one embodiment, the genome of the mutant *Listeria* that is attenuated for entry into non-phagocytic cells comprises at least one mutation in a gene selected from the group consisting of the inlA gene, inlB gene, inlC gene, inlC2 gene, the inlD gene, the inlE gene, the inlF gene, the inlG gene, and the inlH gene. In another embodiment, the genome of the mutant *Listeria* comprises at least one mutation in a gene selected from the group consisting of the inlB gene, inlC gene, inlC2 gene, the inlD gene, the inlE gene, the inlF gene, the inlG gene, and the inlH gene. In one embodiment, the mutant *Listeria* is a mutant *Listeria monocytogenes* that is defective with respect to internalin B. In still another embodiment, the mutant *Listeria* is a mutant *Listeria monocytogenes* and its genome comprises at least one mutation in the inlB gene. In another embodiment the mutant *Listeria* comprises at least one mutation in an internalin gene other than the inlA gene. In another embodiment, the mutant *Listeria* comprises at least one mutation in the inlA gene.

Throughout this disclosures (including figures), alternative terminology is used to refer to the genetic mutations, whether they be mutations that attenuate the *Listeria* for entry into non-phagocytic cells or other mutations (such as cell-to-cell spread mutations). The terms "xyz", "Δxyz", and "xyz deletion mutant" are used interchangeably herein to refer to deletion mutants in which at least most or all of the xyz gene's coding sequence. (In many cases, the whole xyz gene has been deleted from these mutants.) For instance, the terms "inlB" and "ΔinlB" and "inlB deletion mutant" are generally used interchangeably herein.

InlA (internalin A) (Gaillard et al., *Cell,* 65:1127-1141 (1991); Genbank accession no. NC_003210) directs the uptake of *Listeria* by epithelial cells such as those of the intestines. Attenuation of *Listeria* by rendering the strain defective with respect to internalin A may improve the safety of the use of the vaccines in pharmaceutical and vaccine compositions. Invasion of the intestinal epithelial cells by *Listeria* can result in a gastrointestinal infection of *Listeria* characterized by fever, headache, diarrhea or nausea.

InlB (internalin B) (Gaillard et al., *Cell,* 65:1127-1141 (1991); Genbank accession number AL591975 (*Listeria monocytogenes* strain EGD, complete genome, segment 3/12, inlB gene region: nts. 97008-98963); and Genbank accession number NC_003210 (*Listeria monocytogenes* strain EGD, complete genome, inlB gene region: nts. 457008-458963), each of which is incorporated by reference herein in its entirety) directs the uptake of *Listeria* by hepatocytes or by endothelial cells such as the vascular endothelial cells of the brain microvasculature that comprise the blood brain barrier. (For further descriptions of internalin B, see Ireton, et al., *J. of Biological Chemistry,* 274: 17025-17032 (1999); Dramsi, et al., *Molecular Microbiology* 16:251-261 (1995); Mansell et al. *J. of Biological Chemistry,* 276: 43597-43603 (2001); and Bierne et al., *J. of Cell Science* 115:3357-3367 (2002), all of which are incorporated by reference herein in their entirety.) Attenuation of *Listeria* by rendering the strain defective with respect to internalin B may improve the safety of the use of the strains in vaccine and pharmaceutical compositions. Infection of hepatocytes by *Listeria* can result in liver inflammation due to hepatocyte lysis. Infection of brain microvascular endothelial cells can result in meningoencephalitis, which is characterized by headache, stiff neck, loss of balance, confusion, obtundation, convulsion, or death. Meningitis is the leading cause of death by *Listeria* among adults.

In some embodiments, the mutant *Listeria* strain of the present invention is a strain of *Listeria* that comprises one or more mutations in its genome that cause the strain to be defective with respect to internalin B relative to the *Listeria* strain without the one or more mutations. A strain of *Listeria* is defective with respect to the production of internalin B if the bacteria of the strain either produce decreased amounts of a functional version of internalin B or express a version of internalin B that is partially or totally nonfunctional, or both. (It is understood that the term "internalin B" as used herein refers not only to the internalin B of *Listeria monocytogenes*, but also to equivalents thereof in *Listeria* of other species.)

In some embodiments, the genome of the *Listeria* comprises one or more mutations in a gene encoding internalin B (inlB). The mutation is optionally a point mutation, an insertion mutation, a termination mutation, a frame shift mutation, or a deletion of part or whole of the gene encoding the internalin B. In some embodiments, all or at least the majority of the sequence encoding internalin B is deleted from the genome of the *Listeria*. In so embodiments, most or all of the inlB gene is deleted. In some embodiments, no functional internalin B is produced by the attenuated *Listeria*.

In some embodiments, the mutation of inlB is in the coding sequence. In these embodiments, the mutation of the inlB renders the internalin B less functional than the protein produced from the non-mutated inlB sequence. In some embodiments, the mutation of the inlB renders internalin B entirely non-functional (about 100% less functional than the non-mutant *Listeria*). In some embodiments the internalin B expressed by the mutant *Listeria* is at least about 90% less functional, at least about 75% less functional, at least about 50% less functional, or at least about 25% less functional than the internalin B of the non-mutant *Listeria*.

In alternative embodiments, expression of inlB in the mutant strain is inhibited relative to a non-mutant strain. For instance, the genome of the mutant *Listeria* may comprise at least one mutation in inlB, where the mutation hinders expression. For instance, the mutation may be in one or more of the control sequences (such as the promoter or ribosome binding region) of inlB, so that expression of inlB is decreased or eliminated. Alternatively, the mutant *Listeria* may comprise at least one mutation in a gene other than inlB, but which nonetheless results in a diminution of the expression levels of internalin B. In some embodiments, expression of internalin B may be reduced by about 100%, by at least about 90%, by at least about 75%, by at least about 50%, or by at least about 25%.

It should be understood that invasions are bacterial proteins that facilitate infection of non-phagocytic cells, as such can be selected from internalin genes or any other bacterial gene whose encoded product facilitates binding and uptake by non-phagocytic cells.

Bacterial mutations can be achieved through traditional mutagenic methods, such as mutagenic chemicals or radiation followed by selection of mutants. Bacterial mutations can also be achieved by one of skill in the art through recombinant DNA technology. For instance, a method of allelic exchange is described in Camilli et al., *Molecular Micro.* 8:143-147 (1993) that is suitable for use in generating mutants such as deletions mutants. (Camilli et al., is incorporated by reference herein in its entirety.) (See also Example 1, below, for a description of an exemplary application of allelic exchange.) Alternatively, the gene replacement protocol described in Biswas et al., *J. Bacteriol.* 175:3628-3635 (1993), can be used. Other similar methods are known to those of ordinary skill in the art.

Confirmation that a particular mutation, such as a particular inlB mutation, is present in a strain of *Listeria* and/or that the strain is defective with respect to its production of a particular internalin, such as internalin B, can be obtained through a variety of methods known to those of ordinary skill in the art. For instance, the relevant portion of the strain's genome can be cloned and sequenced. Alternatively, specific mutations can be identified via PCR using paired primers that code for regions adjacent to a deletion or other mutation. Southern blots can also be used to detect changes in the bacterial genome. Also, one can analyze whether a particular protein is expressed by the strain using techniques standard to the art such as Western blotting. Confirmation that the strain contains a mutation in the desired gene may also be obtained through comparison of the phenotype of the strain with a previously reported phenotype. For instance, confirmation that the strain is defective with respect to internalin B may also be obtained through comparison of the phenotype of the strain with the previously reported phenotypes for internalin B mutants.

A mutant strain can optionally be evaluated for usefulness in the present invention by evaluating whether or not the strain is attenuated for entry into at least one type of non-phagocytic cell (see Section II.A, above). To determine suitability for use in the methods and compositions of the present invention, the mutant strain can also be evaluated for its ability to be taken up by phagocytic cells.

The appropriateness of a particular *Listeria* mutant, such as *Listeria* comprising a deletion in a particular internalin gene (e.g., inlB), for use in a vaccine can be assessed by measuring the strain's $LD_{50}$, protection afforded by the strain against wild type *Listeria* challenge, ability of the strain to induce specific T cell response to an antigen, ability of the strain to induce an in vivo cytotoxic response against cells expressing an antigen, and/or therapeutic effectiveness of the strain in vivo against a targeted pathology (e.g. in a mouse model), as well as other types of assays known to those of ordinary skill in the art. Specific examples of some of these assays are shown in the Examples 2-7, below. The measurement of $LD_{50}$ of mutant *Listeria* is exemplified in Example 2, below. The immunogenicity of various mutant strains of *Listeria* are tested by ICS assays in Examples 5-7, below. Example 3, below, presents an example of one possible assay for assessing in vivo cytotoxicity of mutant *Listeria* strains. Example 4, below, provides an example of an assay testing the therapeutic efficacy of a mutant *Listeria* strain.

As described above, the invention further provides a method of decreasing the ability of a strain of *Listeria* to enter non-phagocytic cell, while substantially retaining the ability to enter phagocytic cells, comprising introducing at least one mutation into at least one gene of the strain that encodes an invasin so as to decrease the levels of active invasin produced by the strain. In one embodiment, the invasin is an internalin other than InlA.

2. *Listeria* Comprising Other Modifications that Affect Entry into Non-Phagocytic Cells In some embodiments, *Listeria* is reacted with polyclonal or monoclonal antibodies (or fragments thereof) that are specific for particular invasin proteins (e.g. internalin B), or, alternatively are specific for multiple antigens or repeated molecular patterns expressed on the surface of the *bacterium* Antibodies (Ab) specific for a selected invasin protein or multiple proteins and/or macromolecules cause the *Listeria* to be attenuated for entry into non-phagocytic cells ("Ab-opsonized" *Listeria* strain) relative to the same *Listeria* strain without Ab treatment ("non-opsonized" *Listeria* strain). (See, for instance, Example 10, below.) The ability of the antibody-bound *Listeria* strain to enter non-phagocytic cells may be reduced by at least about 10%, at least about 25%, at least about 50%, at least about 75%, or at least about 90%, relative to the non-antibody-bound *Listeria* strain.

In some alternative embodiments of the invention, the ability of *Listeria* to enter non-phagocytic cells is attenuated by blockage of one or more key moieties on the surface of the *Listeria*. For instance, a protein involved in the entry of *Listeria* into phagocytic cells may be blocked by an entity which binds the cell-surface protein and blocks its inability to bind to its receptors on a non-phagocytic cell. In some embodiments, an internalin on the surface of the *Listeria* is blocked. In some embodiments, the cell surface protein is internalin B. In some embodiments, the key moiety on the surface of the *Listeria* is blocked with an antibody or an antibody fragment, such as a Fab fragment. In some embodiments, the surface of the *Listeria* is coated with anti-*Listeria* antibodies or antibody fragments.

In some embodiments, the ability of *Listeria* to enter non-phagocytic cells is effected by opsonization of the *Listeria*. In some embodiments, the attenuated *Listeria* has been opsonized by high titer anti-*Listeria* serum. In some embodiments, the attenuated *Listeria* has been opsonized with polyclonal antibodies. In other embodiments, the attenuated *Listeria* has been opsonized with monoclonal antibodies. In some embodiments, the antibodies used to modify the *Listeria* through opsonization are polyclonal anti-*Listeria* antibodies. In some embodiments, the antibodies used to opsonize the *Listeria* are anti-internalin antibodies, such as internalin B specific monoclonal or polyclonal antibodies, or fragments thereof.

*Listeria*-specific antibodies can be produced by techniques well-known to those of ordinary skill in the art, such as by i.v, infection of mice with *Listeria* to produce high-titer *Listeria*-specific mouse serum. Opsonized *Listeria* can then be generated by incubation of the *Listeria* to be attenuated with the anti-*Listeria* mouse serum. The inventors have shown that such resulting opsonized *Listeria* is attenuated for entry into non-phagocytic cells, but not phagocytic cells (see, e.g., Example 10, below).

Accordingly, in some embodiments, the attenuated *Listeria bacterium* is opsonized. In some embodiments, the opsonized *Listeria* is also attenuated for cell-to-cell spread. For instance, the attenuated *Listeria bacterium* may be an opsonized *Listeria bacterium* that is defective with respect to ActA (e.g., an actA deletion mutant).

B. Attenuation of *Listeria* for Cell-to-Cell Spread

In some embodiments, the attenuated *Listeria* used in the compositions, vaccines, and methods described herein are not only attenuated for entry into non-phagocytic cells, but are also attenuated for cell-to-cell spread. A *Listeria bacterium* is attenuated for cell-to-cell spread if the *Listeria bacterium* is less able to spread intercellularly from one infected cell (a cell comprising the *Listeria* within its cytoplasm) to a neighboring cell. In other words, the ability of the attenuated *Listeria bacterium* to grow and spread is diminished relative to wild type *Listeria* of the same species. In some embodiments, the attenuation of the *Listeria* for cell-to-cell spread is directly affected. For instance, in some embodiments, the *Listeria* is attenuated for cell-to-cell spread because the ability of the *Listeria* to form protrusions from the infected cell that enter a neighboring cell is impaired relative to wild type. In other embodiments, the attenuation of the *Listeria* for cell to cell spread is due to a less direct impairment that nonetheless attenuates the *Listeria* for cell-to-cell spread. For instance, in some alternative embodiments, the ability of *Listeria* to exit the vacuole of a phagocytic cell is impaired.

In some embodiments, the ability of the attenuated *Listeria* to spread cell-to-cell is reduced by at least about 10%, at least about 25%, at least about 50%, at least about 75%, or at least about 90%, relative to wild-type *Listeria*. In some embodiments, the ability of the attenuated *Listeria* to spread cell-to-cell is reduced by at least about 50%, at least about 75%, or at least about 90%, relative to wild-type *Listeria*. In some embodiments, the ability of the attenuated *Listeria* to spread cell-to-cell is reduced by at least about 50% relative to wild type *Listeria*.

In some embodiments, the attenuated *Listeria* comprise mutations in their genomes which attenuate the *Listeria* for spread. For instance, in some embodiments, the attenuated *Listeria bacterium* belongs to a mutant strain of *Listeria*. In some embodiments of the present invention, the genome of the mutant strain of *Listeria* comprises one or more mutations in a gene other than an invasin gene. For instance, in some embodiments, the genome of the mutant strain of *Listeria* comprises one or more mutations in a gene other than inlB. For instance, the mutant strain may also be deficient in one or more virulence factors that affect cell-to-cell spread. In other embodiments, the *Listeria* are attenuated for cell-to-cell spread through alternative means.

Even in those embodiments where the attenuated *Listeria* are attenuated for cell-to-cell spread, the attenuated *Listeria* are preferably still capable of entry into phagocytic cells, such as dendritic cells and/or macrophages. In one embodiment the ability of the attenuated *Listeria* strain to enter phagocytic cells is not diminished by the modification made to the *Listeria* (i.e. approximately 95% or more of the measured ability of the strain to enter phagocytic cells is maintained post-modification). In other embodiments, the ability of the attenuated *Listeria* to enter phagocytic cells is diminished by no more than about 10%, no more than about 25%, no more than about 50%, or no more than about 75%, relative to wild type.

In vitro assays for determining whether or not a *Listeria* bacterium is attenuated for cell-to-cell spread are known to those of ordinary skill in the art. For example, the diameter of plaques formed over a time course after infection of selected cultured cell monolayers can be measured. Plaque assays within L2 cell monolayers can be performed as described previously (Sun, A., A. Camilli, and D. A. Portnoy. 1990, Isolation of *Listeria monocytogenes* small-plaque mutants defective for intracellular growth and cell-to-cell spread. *Infect. Immun.* 58:3770-3778), with modifications to the methods of measurement, as described by (Skoble, J., D. A. Portnoy, and M. D. Welch. 2000, Three regions within ActA promote Arp2/3 complex-mediated actin nucleation and *Listeria monocytogenes* motility. *J. Cell Biol.* 150:527-538). In brief, L2 cells are grown to confluency in six-well tissue culture dishes and then infected with bacteria for 1 h. Following infection, the cells are overlayed with media warmed to 40° C. that is comprised of DME containing 0.8% agarose, Fetal Bovine Serum (e.g., 2%), and a desired concentration of Gentamicin. The concentration of Gentamicin in the media dramatically affects plaque size, and is a measure of the ability of a selected *Listeria* strain to effect cell-to-cell spread (Glomski, I J., M. M. Gedde, A. W. Tsang, J. A. Swanson, and D. A. Portnoy. 2002. *J. Cell Biol.* 156:1029-1038). For example, at 3 days following infection of the monolayer the plaque size of *Listeria* strains having a phenotype of defective cell-to-cell spread is reduced by at least 50% as compared to wild-type *Listeria*, when overlayed with media containing Gentamicin at a concentration of 50 µg/ml. On the other hand, the plaque size between *Listeria* strains having a phenotype of defective cell-to-cell spread and wild-type *Listeria* is similar, when infected monolayers are overlayed with media+agarose containing only 5 µg/ml gentamicin. Thus, the relative ability of a selected strain to effect cell-to-cell spread in an infected cell monolayer relative to wild-type *Listeria* can be determined by varying the concentration of gentamicin in the media containing agarose. Optionally, visualization and measurement of plaque diameter can be facilitated by the addition of media containing Neutral Red (GIBCO BRL; 1:250 dilution in DME+agarose media) to the overlay at 48 h. post infection. Additionally, the plaque assay can be performed in monolayers derived from other primary cells or continuous cells. For example HepG2 cells, a hepatocyte-derived cell line, or primary human hepatocytes can be used to evaluate the ability of selected mutants to effect cell-to-cell spread, as compared to wild-type *Listeria*. In some embodiments, *Listeria* comprising mutations or other modifications that attenuate the *Listeria* for cell-to-cell spread produce "pinpoint" plaques at high concentrations of gentamicin (about 50 µg/ml).

The attenuation of the attenuated *Listeria* of the present invention can also be measured less directly, in terms of biological effects of the *Listeria* on a host. The pathogenicity of attenuated *Listeria* can be assessed by measurement of the $LD_{50}$ in mice or other vertebrates (see Example 2, Table 1). The $LD_{50}$ is the amount, or dosage, of *Listeria* injected into vertebrates necessary to cause death in 50% of the vertebrates. The $LD_{50}$ values can be compared for *Listeria* having a particular mutation or modification versus *Listeria* without the particular mutation or modification as a measure of the level of attenuation. For example, if the *Listeria* strain without a particular mutation or modification has an $LD_{50}$ of $10^3$ bacteria and the *Listeria* strain having the particular mutation or modification has an $LD_{50}$ of $10^5$ bacteria, the strain has been attenuated so that its $LD_{50}$ is increased 100-fold or by 2 log.

The degree of attenuation may also be measured qualitatively by other biological effects, such as the extent of tissue pathology or serum liver enzyme levels. Alanine aminotransferase (ALT), aspartate aminotransferase (AST), albumin and bilirubin levels in the serum are determined at a clinical laboratory for mice injected with *Listeria* of the present invention. Comparisons of these effects in mice or other vertebrates can be made for *Listeria* with and without particular mutations as a way to assess the attenuation of the *Listeria*. Attenuation of the *Listeria* relating to the present invention may also be measured by tissue pathology. The amount of *Listeria* that can be recovered from various tissues of an infected vertebrate, such as the liver, spleen and nervous system, can also be used as a measure of the level of attenuation by comparing these values in vertebrates injected with attenuated versus non-attenuated *Listeria*. For instance, the amount of *Listeria* that can be recovered from infected tissues such as liver or spleen as a function of time can be used as a measure of attenuation by comparing these values in mice injected with attenuated vs. non-attenuated *Listeria*.

The degree of attenuation for cell-to-cell spread of the bacteria involved in the vaccines of the present invention need not be an absolute attenuation in order to provide a safe and effective vaccine. In some embodiments, the degree of attenuation is one that provides for a reduction in toxicity sufficient to prevent or reduce the symptoms of toxicity to levels that are not life threatening.

1. *Listeria* Comprising Mutations that Affect Cell-to-Cell Spread

In some embodiments, the attenuated *Listeria* bacterium comprises one or more mutations that further attenuates the bacterium for cell-to-cell spread. For instance, in some embodiments, the attenuated *Listeria* is a mutant *Listeria* strain that is defective with respect to one or more Listerial protein involved in cell-to-cell spread, such as those selected from the group consisting of ActA, lipoate protein ligase, PI-PLC, PC-PLC, zinc-dependent metalloprotease and LLO (or equivalents of these proteins, depending on the species of *Listeria* used). In some embodiments, the attenuated *Listeria* is a mutant *Listeria* strain that comprises one or more mutation in a gene selected from the group consisting of actA, lplA, plcA, plcB, mpl, and hly (or equivalents of these genes, depending on the species of *Listeria* used), wherein the mutation in the gene attenuates the bacterium for cell-to-cell spread.

In some embodiments, the *Listeria* bacterium is attenuated for entry into non-phagocytic cells (e.g., deficient in one or more internalins such as internalin B) and is also defective with respect to one or more actin polymerizing protein. One such actin polymerizing protein is the actin polymerase encoded by the actA gene (Kocks, et al., *Cell,* 68:521-531 (1992); Genbank accession no. AL591974, nts 9456-11389). The actin polymerase protein is involved in the recruitment and polymerization of host F-actin at one pole of the *Listeria* bacterium. Subsequent polymerization and dissolution of actin results in *Listeria* propulsion throughout the cytosol and into neighboring cells. This mobility enables the bacteria to spread directly from cell-to-cell without further exposure to the extracellular environment, thus escaping host defenses such as antibody development. In some embodiments, the attenuated *Listeria* optionally comprises both a mutation in an internalin gene, such as inlB, and in actA. The *Listeria* strain of this embodiment of the present invention is attenuated for entry into non-phagocytic cells as well as attenuated for cell-to-cell spreading. The terms "actA−", "ΔactA", and "actA deletion mutant" are all used interchangeably herein.

In some embodiments, the attenuated *Listeria bacterium* is a mutant strain of *Listeria monocytogenes* that is defective with respect to both internalin B and the actin polymerase encoded by actA. In another embodiment, the genome of the mutant strain of *Listeria* is a genome of a mutant strain of *Listeria monocytogenes* that comprises a mutation in both inlB and actA (for example, deletion of most or all of the coding sequences for internalin B and ActA). In one embodiment, the strain is the *Listeria monocytogenes* ΔactAΔinlB double mutant deposited with the American Type Culture Collection (ATCC) on Oct. 3, 2003, and designated with accession number PTA-5562. In another embodiment, the strain is a mutant of the strain designated as PTA-5562, where the mutant is defective with respect to both internalin B and ActA relative to wild-type *Listeria monocytogenes*. Again, as previously indicated the terms "actA⁻" and "ΔactAΔinlB" are used interchangeably herein to refer to the double deletion mutant.

In some embodiments, the genome of the attenuated *Listeria* is defective for lipoate protein ligase encoded by the lplA gene (O'Riordan, et al., *Science*, 302:462-4 (2003); Genbank accession no. NC_003210). In some embodiments, the attenuated *Listeria* is defective both with respect to internalin B and a lipoate protein ligase. In some embodiments, the attenuated *Listeria* is a mutant that comprises a mutation in the lplA gene. In some embodiments, the attenuated *Listeria* comprises a mutation in both inlB and lplA. Some exemplary lplA mutants are described in the published U.S. application 2004/0013690, incorporated by reference herein in its entirety.

In some embodiments, the *Listeria bacterium* that is attenuated for entry into non-phagocytic cells is also defective with respect to one or more phospholipases. In some embodiments, the attenuated *Listeria* is a mutant *Listeria* strain defective with respect to one or more internalins (such as internalin B) and also defective with respect to and/or mutated in one or more phospholipases. Phospholipases are a class of enzymes that catalyze the hydrolysis of phosphoglycerides. Phospholipase C is a phosphodiesterase that releases diacyl glycerol, a second messenger in other bacterial pathways. In *Listeria* these contribute to the formation of pores in the phagolysosomal membrane. In some embodiments, the phospholipase genes that are mutated in the *Listeria* involved in the present invention are selected from the group consisting of plcA, plcB and smcL. In some embodiments, the attenuated *Listeria* is defective with respect to PC-PLC and/or PI-PLC. In some embodiments, the attenuated *Listeria* comprises one or more mutations in the plcA and/or plcB genes (Genbank accession no. NC_003210; Angelakopolous H. et al., 2002, Infect. Immun. 70:3592-3601). In some embodiments, the attenuated *Listeria* comprises a mutation in the smcL gene. In some embodiments, the attenuated Listera comprises attenuating mutations in inlB and in plcA and/or plcB. The *Listeria* strain of these embodiments of the present invention is attenuated for entry into non-phagocytic cells as well as escape from the phagolysosome into the cytosol of the host cell, and, as a result, for cell-to-cell spread.

In some embodiments, the genome of the attenuated *Listeria* is defective for the zinc-dependent metalloprotease encoded by the mpl gene (Marquis, et al., *J. Cell. Biol.* 137: 1381-92 (1997); Genbank accession no. NC_003210). In some embodiments, the attenuated *Listeria* is defective both with respect to internalin B and a zinc-dependent metalloprotease. In some embodiments, the attenuated *Listeria* is a mutant that comprises a mutation in the mpl gene. In some embodiments, the attenuated *Listeria* comprises an attenuating mutation in both inlB and mpl.

In some embodiments, the *Listeria bacterium* that is attenuated for entry into non-phagocytic cells is also defective with respect to LLO. In some embodiments, the mutant strains of *Listeria* that are defective with respect to one or more invasins (e.g., internalin B) are also defective with respect to and/or mutated for one or more *Listeria* proteins effective in mediating the escape and spread of *Listeria* from the initial site of invasion. Such escape proteins can comprise native listeriolysin O (LLO; Genbank accession no. M24199, incorporated herein by reference in its entirety) as well as mutant forms of LLO. In some embodiments, the genome of the attenuated *Listeria bacterium* comprises a mutation in the hly gene that encodes LLO. LLO is a cytolysin protein responsible for forming pores in the membrane of the phagolysosomes that encapsulate invading *Listeria*. These pores enable *Listeria* to escape the killing environment of the phagolysosome into the cytosol of the host cell, where the *Listeria* can grow and spread to neighboring cells. One possible mutant LLO protein of the *Listeria* comprises amino acid substitutions. Such amino acid substitutions can involve one or more amino acids of the LLO protein and can affect the cytotoxicity of the LLO by altering the pH optimum or the stability of the resulting protein. Another mutant LLO protein of the *Listeria* involved in the present invention comprises the deletion of one or more amino acids of the LLO. Such amino acid deletions can also affect the cytotoxicity by altering the stability of resulting LLO protein. The *Listeria* strains involved in the present invention that are deficient in one or more internalins and are also deficient or mutated for the LLO protein are attenuated for entry into non-phagocytic cells as well as attenuated for escape from the phagolysosome and the resulting growth and spread directly from cell to cell. Some exemplary hly mutants are described in the published U.S. application 2004/0013690, incorporated by reference herein in its entirety.

Accordingly, in some embodiments, the genome of the *Listeria bacterium* attenuated for entry into non-phagocytic cells is further attenuated for cell-to-cell spread and comprises at least one mutation in one or more genes selected from the group consisting of actA, hly, lplA, plcA, mpl and plcB. In an alternative embodiment, the genome of the mutant strain further comprises at least one mutation in actA. For example, the genome of the modified *Listeria bacterium* may comprise at least one mutation in both inlB and a gene selected from the group consisting of actA, hly, lplA, plcA, mpl and plcB. Alternatively, the genome of the attenuated *Listeria* comprises at least one mutation in both inlB and actA.

The additional mutations in the *Listeria* strains can be introduced and screened for in the same manner as that described in Section II.A, above, or in the Examples, below. Multiple mutations will typically be introduced sequentially. For instance, starting with wild-type *Listeria*, the actA gene can be deleted using allelic exchange. Lastly, the inlB gene can then be deleted from the actA mutant or the actA/uvrAB mutant through allelic exchange to generate the actA/inlB mutant.

In alternative embodiments, existing mutant *Listeria* strains known to those in the art are further modified to introduce mutations that will attenuate their ability to enter non-phagocytic cells and/or to render the strains defective with respect to internalin B. For instance, a number of mutant *Listeria* strains, have been described previously. The mutant strain LLO L461T (DP-L4017) was described in Glomski, et al, *J. Cell. Biol.* 156: 1029 (2002), incorporated by reference herein. The ΔactA mutant (DP-L4029) is the DP-L3078 strain described in Skoble et al., *J. of Cell Biology*, 150: 527-537

(2000), incorporated by reference herein in its entirety, which has been cured of its prophage. (Prophage curing is described in (Lauer et al., *J. Bacteriol.* 184:4177 (2002): U.S. Patent Publication No. 2003/0203472).) The LLO⁻ mutant (DP-L4027) (Lauer et al., *J. of Bacteriology*, 184:4177-4186 (2002)), and LLO Δ26 (DP-L4042) (Decatur et al, *Science* 290:992 (2000)) were also described previously. Any of these strains could comprise a starting point to produce a mutant *Listeria* strain of the present invention. Alternatively, any one of a wide variety of mutant *Listeria* strains may first be generated from wild-type *Listeria* using the allelic exchange methods described above or other methods known to those of ordinary skill in the art and then the mutation attenuating the bacteria for entry into non-phagocytic cells (such as inlB) may be introduced into the strain at a later point.

The appropriateness of a particular *Listeria* strain attenuated for entry into non-phagocytic cells (e.g., a strain defective with respect to internalin B) that is also attenuated for cell-to-cell spread for use in a vaccine can be assessed using the same types of assays as described for assessing proper mutations affecting invasins in Section II.A., above.

It is understood that the genomes of the attenuated *Listeria* of the present invention may also comprise additional mutations that neither attenuate the *Listeria* for entry into non-phagocytic cells nor for cell-to-cell spread.

2. *Listeria* Comprising other Modifications that Affect Cell-to-Cell Spread

In some embodiments, the *Listeria bacterium* that is attenuated for both entry into non-phagocytic cells and for cell-to-cell spread has been modified by alternative means (or by a means in addition to) those mutations outlined above. For instance, in some embodiments, the Listerial nucleic acid of the *Listeria bacterium* has been modified so that proliferation of the *bacterium* is attenuated, thereby attenuating the *bacterium* for cell-to-cell spread.

In some embodiments, the attenuation of the proliferation of the *Listeria* is controllable in a dose-dependent manner. In some embodiments, the expression of Listerial genes in the *Listeria bacterium* is substantially unaffected by attenuation of the proliferation of the microbe. In Some embodiments, the *Listeria* expresses an antigen at a sufficient level to induce an immune response to the antigen in an individual upon administration of the vaccine to the individual.

In some embodiments, the nucleic acid of the *bacterium* has been modified by reaction with a nucleic acid targeting compound so that proliferation of the *bacterium* is attenuated. In some embodiments, the nucleic acid of the *Listeria* has been modified by reaction with a nucleic-acid targeting compound that reacts directly with the nucleic acid. In some embodiments, the nucleic-acid targeting compound is a nucleic acid alkylator. For instance, in some embodiments, the nucleic acid alkylator is β-alanine, N-(acridin-9-yl), 2-[bis(2-chloroethyl)amino]ethyl ester. In some embodiments, the nucleic acid targeting compound is activated by irradiation. In some embodiments, the nucleic acid targeted compound is a psoralen compound activated by UVA irradiation and the nucleic acid of the attenuated *Listeria bacterium* has been modified by contact with the psoralen compound activated by UVA irradiation. For instance, in some embodiments, the nucleic acid targeting compound is 4'-(4-amino-2-oxa)butyl-4,5',8-trimethylpsoralen (also referred to herein as "S-59"). Exemplary protocol for S-59/UVA inactivation of *Listeria* are provided in Example 11, below. Further descriptions of the use of targeting compounds such as crosslinking compounds are provided in the related applications U.S. Ser. Nos. 60/446,051, 60/449,153, and 60/511,869, incorporated by reference herein in their entirety. Likewise, the related U.S. patent application entitled "Modified Free-Living Microbes, Vaccine Compositions, and Methods of Use Thereof," filed on Feb. 6, 2004, is also incorporated by reference herein in its entirety.

In some embodiments, the attenuated *Listeria bacterium* has not only been attenuated for entry into non-phagocytic cells and its nucleic acid modified so that it is attenuated for proliferation (as described above), but it is also defective with respect to a protein that functions to repair modifications to the Listerial nucleic acid. In some embodiments, the attenuated *Listeria* is defective with respect to a DNA repair enzyme. In some embodiments, the mutant *Listeria* strain is deficient with respect to both internalin B and a protein that functions to repair modifications to its nucleic acid. For instance, a mutant strain of *Listeria* that comprises a mutation in inlB could also comprise a mutation in any of a variety of genes that are involved in the DNA repair mechanisms of microbes (Aravind et al., Nucleic Acids Research 27(5): 1223-1242 (1999)). In one embodiment the repair deficient mutant lacks the ability to make PhrB (a photolyase), which repairs pyrimidine dimers. For example, the additional mutation may be in the phrB gene, or a functionally equivalent gene, depending on the species of the *Listeria*. Such a mutant could be used in conjunction with ultraviolet irradiation (e.g., UVB, UVC) of the microbe to produce pyrimidine dimers in the microbial nucleic acid. In another embodiment the internalin B mutant is also unable to repair interstand crosslinks. Such mutants include, but are not limited to, mutations in one or all uvr genes, i.e. uvrA, uvrB, uvrC, and uvrD genes as well as recA genes, or functionally equivalent genes, depending on the genus and species of the microbe. These mutations result in attenuation in the activity of the corresponding enzymes UvrA (an ATPase), UvrB (a helicase), UvrC (a nuclease), UvrD (a helicase II) and RecA (a recombinase). These mutants would typically be used in conjunction with a crosslinking compound, such as a psoralen. In one embodiment, there are attenuating mutations in both uvrA and uvrB (uvrAB).

Accordingly, in one embodiment, the genome of the mutant strain attenuated for entry into non-phagocytic cells, further comprises at least one mutation in a least one gene selected from the group consisting of phrB, uvrA, uvrB, uvrC, uvrD, and recA. For example, the genome of the mutant *Listeria* may comprise at least one mutation in both inlB and a gene selected from the group consisting of phrB, uvrA, uvrB, uvrC, uvrD, and recA. Alternatively, the attenuated *Listeria* is a mutant *Listeria monocytogenes* that comprises at least one mutation in inlB, actA, and uvrAB.

The additional mutations in the *Listeria* strains can be introduced and screened for in the same manner as that described in Section II.A, above, or in the Examples, below. Multiple mutations will typically be introduced sequentially. For instance, starting with wild-type *Listeria*, the actA gene can be deleted using allelic exchange. Next, the uvrA and uvrB genes can optionally be deleted from the ΔactA mutant using allelic exchange. (A *Listeria monocylogenes* ΔactAΔuvrAB mutant was deposited with ATCC on Oct. 3, 2003, and designated PTA-5563.) Lastly, the inlB gene can then be deleted from the ΔactA mutant or the ΔactAΔuvrAB mutant (also known as $actA^-/uvrAB^-$) through allelic exchange to generate the ΔactAΔinlBΔuvrAB (also known as $actA^-/inlB^-/uvrAB^-$) mutant.

In alternative embodiments, existing mutant *Listeria* strains known to those in the art are further modified to introduce mutations that will attenuate their ability to enter non-phagocytic cells and/or to render the strains defective with respect to internalin B. For instance, construction of the ΔactAΔuvrAB strain is described in the copending U.S. provisional application 60/446,051, filed Feb. 6, 2003, as L4029/uvrAB⁻ (see, e.g. Example 7 of that application). This strain could comprise a starting point to produce a mutant *Listeria* strain of the present invention. Alternatively, any one of a wide variety mutant *Listeria* strains may first be generated from wild-type *Listeria* using the allelic exchange methods described above or other methods known to those of ordinary skill in the art and then the mutation attenuating the bacteria for entry into non-phagocytic cells (such as inlB) may be introduced into the strain at a later point.

The appropriateness of a particular attenuated *Listeria* strain (e.g., a strain defective with respect to internalin B) that is also attenuated for cell-to-cell spread for use in a vaccine can be assessed using the same types of assays as described for assessing proper mutations affecting invasins in Section II.A., above.

U.S. Provisional application Nos. 60/446,051, 60/449,153, and 60/511,869 (each of which is incorporated by reference) provide additional information regarding the preparation and assessment of attenuated *Listeria* comprising genetic mutations that attenuate the ability of the *Listeria* to repair its nucleic acid that has been modified. Likewise, the related U.S. patent application entitled "Modified Free Living Microbes, Vaccine Compositions, and Methods of Use Thereof," filed on Feb. 6, 2004, is also incorporated by reference herein in its entirety.

C. Antigens and Heterologous Protein Expression

In some embodiments of the present invention, the attenuated *Listeria* (e.g., the mutant *Listeria* strains) comprise a nucleic acid molecule encoding an antigen. In some embodiments, the antigen is a Listerial antigen. Alternatively, the antigen is a non-Listerial antigen. In some, although not all, embodiments of the invention, the nucleic acid encoding the antigen is heterologous with respect to the mutant *Listeria*. The nucleic acid molecule encoding the antigen may be integrated into the genome of the mutant *Listeria*. Alternatively, the nucleic acid molecule encoding the antigen may be on a plasmid or the like within the *Listeria*.

The antigen that is expressed by the heterologous nucleic acid in the mutant *Listeria* strain may be either autologous or heterologous to a host animal to which the mutant *Listeria* strain is administered as part of a vaccine or other composition.

Methods of preparing *Listeria* containing heterologous nucleic acids that express antigens are known to those of ordinary skill in the art. The *Listeria* may be altered by recombinant DNA methods known to those skilled in the art (see, e.g., Sambrook and Russell, Molecular Cloning: A Laboratory Manual, Third Edition, Cold Spring Harbor Laboratory Press, (2000)). The coding sequence for the antigen, or a fragment and/or variant thereof, is operably linked to appropriate regulatory sequences to effect expression of the antigen sequence within the *Listeria*. Suitable promoter sequences are known to those of ordinary skill in the art. For instance, the hly promoter is suitable for use in the expression constructs. In some embodiments, the expression constructs containing the antigen coding sequences further comprise operably linked signal peptide sequences. In some embodiments, the antigen sequence is fused, directly or indirectly, to sequences encoding at least portions of Listerial proteins such as LLO. Specific examples of integrational vectors suitable for expression of antigens in *Listeria* include pPL2 and pPL1, described in Lauer et al., *J. Bacteriol.* 184:41777-4186 (2002) and U.S. Patent Pub. No. 2003/0203472 A1, incorporated by reference herein in their entirety.

The heterologous nucleic acid sequence can encode at least one specific protein antigen or other protein, such as a protein that provides a palliative treatment for a disease. The *Listeria* can be altered to contain one or more sequences that encode one or more antigens or other desired proteins. The heterologous nucleic acid sequence encoding a specific antigen is not limited to an exact nucleic acid sequence but is of a sequence that is sufficient to provide the expression of an antigen that will elicit the desired immune response when administered to an individual. Similarly for heterologous sequences encoding other proteins, the sequences encoding a given protein may vary so long as the desired protein is expressed in order to provide the desired effect (e.g. a palliative effect) when administered to an individual. The heterologous sequence can be expressed as an antigen related to a particular disease. The *Listeria* expressing such antigens can be used as a vaccine, wherein the vaccine may be used as a preventative treatment or a therapeutic treatment. Diseases that can be treated by such vaccines include, but are not limited to, infectious diseases, autoimmune diseases, allergies, cancers and other hyperproliferative diseases.

The *Listeria* involved in the invention may be altered to contain a heterologous nucleic acid sequence encoding an antigen that is a tumor-associated antigen or is derived from a tumor-associated antigen. A large number of tumor-associated antigens that are recognized by T cells have been identified (Renkvist et al., *Cancer Immunol Innumother* 50:3-15 (2001)). These tumor-associated antigens may be differentiation antigens (e.g., PSMA, Tyrosinase, gp100), tissue-specific antigens (e.g. PAP, PSA), developmental antigens, tumor-associated viral antigens (e.g. HPV 16 E7), cancer-testis antigens (e.g. MAGE, BAGE, NY-ESO-1), embryonic antigens (e.g. CEA, alpha-fetoprotein), oncoprotein antigens (e.g. Ras, p53), over-expressed protein antigens (e.g. ErbB2 (Her2/Neu), MUC1), or mutated protein antigens. The tumor-associated antigens that may be encoded by the heterologous nucleic acid sequence include, but are not limited to, 707-AP, Annexin II, AFP, ART-4, BAGE, β-catenin/m, BCL-2, bcr-abl, bcr-abl p190, bcr-abl p210, BRCA-1, BRCA-2, CAMEL, CAP-1, CASP-8, CDC27/m, CDK-4/m, CEA (Huang et al., *Exper Rev. Vaccines* (2002) 1:49-63), CT9, CT10, Cyp-B, Dek-cain, DAM-6 (MAGE-B2), DAM-10 (MAGE-B1), EphA2 (Zantek et al., *Cell Growth Differ.* (1999) 10:629-38; Carles-Kinch et al., *Cancer Res.* (2002) 62:2840-7), ELF2M, ETV6-AML1, G250, GAGE-1, GAGE-2, GAGE-3, GAGE-4, GAGE-5, GAGE-6, GAGE-7B, GAGE-8, GnT-V, gp100, HAGE, HER2/neu, HLA-A*0201-R170I, HPV-E7, HSP70-2M, HST-2, hTERT, hTRT, iCE, inhibitors of apoptosis (e.g. survivin), KIAA0205, K-ras, LAGE, LAGE-1, LDLR/FUT, MAGE-1, MAGE-2, MAGE-3, MAGE-6, MAGE-A1, MAGE-A2, MAGE-A3, MAGE-A4, MAGE-A6, MAGE-A10, MAGE-A12, MAGE-B5, MAGE-B6, MAGE-C2, MAGE-C3, MAGE-D, MART-1, MART-1/Melan-A, MC1R, MDM-2, mesothelin, Myosin/m, MUC1, MUC2, MUM-1, MUM-2, MUM-3, neo-polyA polymerase, NA88-A, NY-ESO-1, NY-ESO-1a (CAG-3), PAGE-4, PAP, Proteinase 3 (Molldrem et al., *Blood* (1996) 88:2450-7; Molldrem et al., *Blood* (1997) 90:2529-34), P15, p190, Pml/RARα, PRAME, PSA, PSM, PSMA, RAGE, RAS, RCAS1, RU1, RU2, SAGE, SART-1, SART-2, SART-3, SP17, SPAS-1, TEL/AML1, TPI/m, Tyrosinase, TARP, TRP-1 (gp75), TRP-2, TRP-2/INT2, WT-1, and alternatively translated NY-ESO-ORF2 and CAMEL proteins, derived from the NY-ESO-1 and LAGE-1 genes. The attenuated *Listeria* of the present invention may encompass any tumor-associated antigen that can elicit a tumor-specific immune response, including antigens yet to be identified. The *Listeria* may be altered to contain more than one heterologous sequence encoding more than one tumor-associated antigen. In one embodiment, the antigen is mesothelin (Argani et al., *Clin Cancer Res.* 7(12):3862-8 (2001)), Sp17 (Lim et al., *Blood* 97(5):1508-10 (2001)), gp100 (Kawakami et al., *Proc. Natl. Acad. Sci. USA* 91:6458 (1994)), PAGE-4 (Brinkmann et al., *Cancer Res.* 59(7):1445-8 (1999)), TARP (Wolfgang et al., *Proc. Natl. Acad. Sci. USA* 97(17):9437-42 (2000)), or SPAS-1 (U.S. Patent Application Publication No. 2002/0150588).

In some embodiments, the heterologous nucleic acid encodes an antigen that is not identical to a tumor-associated antigen, but rather is derived from a tumor-associated antigen. For instance, the antigen expressed by the mutant *Listeria* may comprise a fragment of a tumor-associated antigen, a variant of a tumor-associated antigen, or a fragment of a variant of a tumor-associated antigen. In some cases, an antigen, such as a tumor antigen, is capable of inducing a more significant immune response in a vaccine when the sequence differs from that endogenous to the host. In some embodiments, the variant of a tumor-associated antigen, or a fragment of a variant of a tumor-associated antigen, differs from that of the tumor-associated antigen, or its corresponding fragment, by one or more amino acids. The antigen derived from a tumor-associated antigen will comprise at least one epitope sequence capable of inducing the desired immune response upon administration of the mutant *Listeria* to a host.

Accordingly, in some embodiments, the attenuated *Listeria bacterium* comprises a nucleic acid molecule encoding an antigen such as mesothelin, SPAS-1, proteinase-3, EphA2, SP-17, gp100, PAGE-4, TARP, Her-2/neu, WT-1, NY-ESO-1, PSMA, K-ras, or CEA, or an antigen derived from one of those proteins. In some embodiments, the attenuated *Listeria bacterium* comprises a nucleic acid molecule encoding an antigen such as mesothelin, SPAS-1, proteinase-3, SP-17, gp100, PAGE-4, TARP, Her-2/neu, WT-1, NY-ESO-1, PSMA, K-ras, or CEA, or an antigen derived from one of those proteins. In some embodiments, the attenuated *Listeria bacterium* comprises a nucleic acid molecule encoding an antigen such as mesothelin, SPAS-1, proteinase-3, EphA2, SP-17, gp100, PAGE-4, TARP, WT-1, NY-ESO-1, or CEA, or an antigen derived from one of those proteins. In other embodiments, the attenuated *Listeria bacterium* comprises a nucleic acid molecule encoding an antigen such as mesothelin, SPAS-1, proteinase-3, SP-17, gp100. PAGE-4, TARP, WT-1, NY-ESO-1, or CEA, or an antigen derived from one of those proteins. In some embodiments, the attenuated *Listeria bacterium* comprises a nucleic acid molecule encoding human mesothelin, or an antigen derived from human mesothelin. In other embodiments, the attenuated *Listeria bacterium* comprises a nucleic acid molecule encoding human EphA2, or derived from human EphA2. In further embodiments, the attenuated *Listeria bacterium* comprises a nucleic acid molecule encoding human NY-ESO-1, or an antigen derived from human NY-ESO-1.

In some other embodiments, the heterologous antigen expressed by the attenuated *Listeria* is proteinase-3 or is derived from proteinase-3. For instance, in one embodiment, the antigen comprises the HLA-A2.1-restricted peptide PR1 (aa 169-177; VLQELNVTV (SEQ ID NO:1)). Information on proteinase-3 and/or the PR1 epitope is publicly available in the following references: U.S. Pat. No. 5,180,819, Molldrem, et al., *Blood*, 90:2529-2534 (1997); Molldrem, et al., *Cancer Research*, 59:2675-2681 (1999); Molldrem, et al., *Nature Medicine*, 6:1018-1023 (2000); and Molldrem et al., *Oncogene*, 21: 8668-8673 (2002).

Alternatively, the attenuated *Listeria* of the invention may be altered to contain a heterologous nucleic acid sequence encoding an autoimmune disease-specific antigen. In a T cell mediated autoimmune disease, a T cell response to self antigens results in the autoimmune disease. The type of antigen for use in treating an autoimmune disease with the vaccines of the present invention might target the specific T cells responsible for the autoimmune response. For example, the antigen may be part of a T cell receptor, the idiotype, specific to those T cells causing an autoimmune response, wherein the antigen incorporated into a vaccine of the invention would elicit an immune response specific to those T cells causing the autoimmune response. Eliminating those T cells would be the therapeutic mechanism to alleviating the autoimmune disease. Another possibility would be to incorporate an antigen that will result in an immune response targeting the antibodies that are generated to self antigens in an autoimmune disease or targeting the specific B cell clones that secrete the antibodies. For example, an idiotype antigen may be incorporated into the *Listeria* that will result in an anti-idiotype immune response to such B cells and/or the antibodies reacting with self antigens in an autoimmune disease.

In other embodiments of the invention, the antigen is derived from a human or animal pathogen. The pathogen is optionally a virus, *bacterium*, fungus, or a protozoan. In one embodiment, the antigen is a protein produced by the pathogen, or a fragment and/or variant of a protein produced by the pathogen.

For instance, the antigen may be derived from Human Immunodeficiency virus (such as gp120, gp 160, gp41, gag antigens such as p24gag and p55gag, as well as proteins derived from the pol, env, tat, vif, rev, nef, vpr, vpu and LTR regions of HIV), Feline Immunodeficiency virus, or human or animal herpes viruses. In one embodiment, the antigen is derived from herpes simplex virus (HSV) types 1 and 2 (such as gD, gB, gH, Immediate Early protein such as ICP27), from cytomegalovirus (such as gB and gH), from Epstein-Barr virus or from Varicella Zoster Virus (such as gpI, II or III). (See, e.g., Chee et al. (1990) Cytomegaloviruses (J. K. McDougall, ed., Springer Verlag, pp. 125-469; McGeoch et al. (1988) J. Gen. Virol. 69: 1531-1574; U.S. Pat. No. 5,171, 568; Baer et al. (1984) Nature 310: 207-211; and Davison et al. (1986) J. Gen. Virol. 67: 1759-1816.)

In another embodiment, the antigen is derived from a hepatitis virus such as hepatitis B virus (for example, Hepatitis B Surface antigen), hepatitis A virus, hepatitis C virus, delta hepatitis virus, hepatitis E virus, or hepatitis G virus. See, e.g., WO 89/04669; WO 90/11089; and WO 90/14436. The hepatitis antigen can be a surface, core, or other associated antigen. The HCV genome encodes several viral proteins, including E1 and E2. See, e.g., Houghton et al., *Hepatology* 14: 381-388(1991).

An antigen that is a viral antigen is optionally derived from a virus from any one of the families Picornaviridae (e.g., polioviruses, rhinoviruses, etc.); Caliciviridae; Togaviridae (e.g., rubella virus, dengue virus, etc.); Flaviviridae; Coronaviridae; Reoviridae (e.g., rotavirus, etc.); Bimaviridae; Rhabodoviridae (e.g., rabies virus, etc.); Orthomyxoviridae (e.g., influenza virus types A, B and C, etc.); Filoviridae; Paramyxoviridae (e.g., mumps virus, measles virus, respiratory syncytial virus, parainfluenza virus, etc.); Bunyaviridae; Arenaviridae; Retroviradae (e.g., HTLV-1; HTLV-11; HIV-1; HIVI11b; HIVSF2; HTVLAV; HIVLAI; HIVMN; HIV-1CM235; HIV-2; simian immunodeficiency virus (SIV)); Papillomavirus, the tick-borne encephalitis viruses; and the like. See, e.g. *Virology*, 3rd Edition (W. K. Joklik ed. 1988); *Fundamental Virology*, 3rd Edition (B. N. Fields, D. M.

Knipe, and P. M. Howley, Eds. 1996), for a description of these and other viruses. In one embodiment, the antigen is Flu-HA (Morgan et al., J. Immunol. 160:643 (1998)).

In some alternative embodiments, the antigen is derived from bacterial pathogens such as *Mycobacterium, Bacillus, Yersinia, Salmonella, Neisseria, Borrelia* (for example, OspA or OspB or derivatives thereof), *Chlamydia*, or *Bordetella* (for example, P.69, PT and FHA), or derived from parasites such as plasmodium or Toxoplasma. In one embodiment, the antigen is derived from the *Mycobacterium tuberculosis* (e.g. ESAT-6, 85A, 85B, 72F), *Bacillus anthracis* (e.g. PA), or *Yersinia pestis* (e.g. F1, V). In addition, antigens suitable for use in the present invention can be obtained or derived from known causative agents responsible for diseases including, but not limited to, Diptheria, Pertussis, Tetanus, Tuberculosis, Bacterial or Fungal Pneumonia, Otitis Media, Gonorrhea, Cholera, Typhoid, Meningitis, Mononucleosis, Plague, Shigellosis or Salmonellosis, Legionaire's Disease, Lyme Disease, Leprosy, Malaria, Hookworm, Onchocerciasis, Schistosomiasis, Tryparnasomialsis, Lesmaniasis, Giardia, Amoebiasis, Filariasis, Borelia, and Trichinosis. Still further antigens can be obtained or derived from unconventional pathogens such as the causative agents of kuru, Cretitzfeldt-Jakob disease (CJD), scrapie, transmissible mink encephalopathy, and chronic wasting diseases, or from proteinaceous infectious particles such as prions that are associated with mad cow disease.

In still other embodiments, the antigen is obtained or derived from a biological agent involved in the onset or progression of neurodegenerative diseases (such as Alzheimer's disease), metabolic diseases (such as Type I diabetes), and drug addictions (such as nicotine addiction). Alternatively, the compositions comprising the antigen-expressing mutant *Listeria* strain is used for pain management and the antigen is a pain receptor or other agent involved in the transmission of pain signals.

In some embodiments, the antigen sequence may be codon-optimized to match the codon preference of the Listerial host expressing the antigen. In addition, the sequence encoding a signal peptide fused to the antigenic peptide may also be codon-optimized to match the codon preference of the Listerial host. For further information on codon optimization of antigens and signal sequences in *Listeria*, see U.S. Provisional application No. 60/532,598, filed on Dec. 24, 2003, incorporated by reference herein.

D. Immunogerlieity of the Attenuated *Listeria*

In some embodiments, the attenuated *Listeria* (e.g., mutant *Listeria* strains) are capable of inducing an immune response in a host animal, in one embodiment, the immune response is a cell-mediated immune response. In one embodiment, the effective immune response induced by the attenuated *Listeria* bacterium comprises a T cell response, such as a CD4+ T cell response or a CD8+ T cell response, or both.

These immune cell responses can be measured by both in vitro and in vivo methods to determine if the immune response of the *Listeria* involved in the present invention is effective. Efficacy can be determined by comparing these measurements for attenuated *Listeria* to those for non-attenuated *Listeria* for any particular antigen or heterologous protein. One possibility is to measure the presentation of the protein or antigen of interest by an antigen-presenting cell that has been mixed with a population of the *Listeria*. The *Listeria* may be mixed with a suitable antigen presenting cell or cell line, for example a dendritic cell, and the antigen presentation by the dendritic cell to a T cell that recognizes the protein or antigen can be measured. If the *Listeria* are expressing the protein or antigen at a sufficient level, it will be processed into peptide fragments by the dendritic cells and presented in the context of MHC class I or class II to T cells. For the purpose of detecting the presented protein or antigen, a T cell clone or T cell line responsive to the particular protein or antigen may be used. The T cell may also be a T cell hybridoma, where the T cell is immortalized by fusion with a cancer cell line. Such T cell hybridomas, T cell clones, or T cell lines can comprise either CD8+ or CD4+ T cells. The dendritic cell can present to either CD8+ or CD4+ T cells, depending on the pathway by which the antigens are processed. CD8+ T cells recognize antigens in the context of MHC class I while CD4+ recognize antigens in the context of MHC class II. The T cell will be stimulated by the presented antigen through specific recognition by its T cell receptor, resulting in the production of certain proteins, such as IL-2, tumor necrosis factor-$\alpha$ (TNF-$\alpha$), or interferon-$\gamma$ (IFN-$\gamma$), that can be quantitatively measured (for example, using an ELISA assay, ELISPOT assay, or Intracellular Cytokine Staining (ICS)). For specific examples of assays measuring immunogenicity, see Examples 5-7 below.

Alternatively, a hybridoma can be designed to include a reporter gene, such as $\beta$-galactosidase, that is activated upon stimulation of the T cell hybridoma by the presented antigens. The increase in the production of $\beta$-galactosidase can be readily measured by its activity on a substrate, such as chlorophenol red-B-galactoside, which results in a color change. The color change can be directly measured as an indicator of specific antigen presentation.

Additional in vitro and in vivo methods for assessing the antigen expression of *Listeria* vaccines of the present invention are known to those of ordinary skill in the art It is also possible to directly measure the expression of a particular heterologous antigen by *Listeria*. For example, a radioactively labeled amino acid can be added to a cell population and the amount of radioactivity incorporated into a particular protein can be determined. The proteins synthesized by the cell population can be isolated, for example by gel electrophoresis or capillary electrophoresis, and the amount of radioactivity can be quantitatively measured to assess the expression level of the particular protein. Alternatively, the proteins can be expressed without radioactivity and visualized by various methods, such as an ELISA assay or by gel electrophoresis and Western blot with detection using an enzyme linked antibody or fluorescently labeled antibody.

Additionally, in some embodiments the attenuated *Listeria* (e.g., mutant *Listeria* strains) expressing heterologous or autologous antigens induce in vivo cytotoxicity against cells expressing and/or bearing the antigens (see, e.g., Example 3, below). In some embodiments, the attenuated *Listeria* that express the heterologous or autologous antigens are therapeutically effective (see, e.g., Example 4, below).

While it is possible that the modification of the *Listeria* may reduce the level of protein expression as compared to non-attenuated *Listeria*, it is understood that in some embodiments the attenuated *Listeria* is still be effective in an immunogenic composition or vaccine. It is the combination of attenuation of non-phagocytic invasion with adequate protein expression that is important in some embodiments of the invention. The efficacy of a vaccine is generally related to the dose of antigen that can be delivered by the microbe. The attenuation of non-phagocytic invasion of the *Listeria* may be several logs while the *Listeria* gene expression is still adequately maintained. If the same dose of an attenuated *Listeria* is compared to that of a *Listeria* without the attenuating modification, the resulting antigen expression (as assessed by the methods discussed above) in the attenuated *Listeria* population is at least 1%, 5%, 10%, 25%, 50%, 75% or at least 90% of the antigen expression in the *Listeria* population without the attenuating modification. Since there may be several log attenuation in non-phagocytic invasion, the dose of the attenuated *Listeria* may be safely increased by up to several log, resulting in a greater amount of the antigen presented by the attenuated *Listeria* relative to *Listeria* without the attenuating modification upon vaccination.

III. Vaccines and Other Compositions Comprising the Attenuated *Listeria*

In addition to the attenuated *Listeria* described herein, the present invention provides a variety of compositions comprising the attenuated *Listeria*, including immunogenic compositions, pharmaceutical compositions, cells, and vaccines. (Exemplary attenuated *Listeria* useful in the compositions of the present invention are described in Section II.A-C, above, and in the Examples, below.)

For instance, the invention provides a pharmaceutical composition comprising (a) an attenuated *Listeria bacterium* which is attenuated for entry into non-phagocytic cells and comprises a nucleic acid molecule encoding a non-Listerial antigen, and (b) a pharmaceutically acceptable excipient. The invention further provides a pharmaceutical composition comprising (a) an attenuated *Listeria bacterium* which is attenuated for entry into non-phagocytic cells and for cell-to-cell spread, and (b) a pharmaceutically acceptable carrier.

The invention also provides a pharmaceutical composition comprising a mutant *Listeria* strain and a pharmaceutically acceptable carrier, wherein the mutant *Listeria* strain is attenuated for entry into non-phagocytic cells relative to a non-mutant *Listeria* strain, but retains an ability to enter phagocytic cells. In one embodiment, the mutant *Listeria* strain is defective with respect to internalin B. In another embodiment, the genome of the mutant strain comprises at least one mutation in at least one gene encoding an invasin, such as an internalin like internalin B. In another embodiment the coding sequence (or gene) of inlB has been deleted from the genome of the strain. In still another embodiment, the coding sequences (or genes) of both inlB and acts has been deleted. A variety of pharmaceutically acceptable carriers suitable for use with bacterial strains are known to those of ordinary skill in the art.

The invention also provides a method of decreasing the toxicity of a pharmaceutical composition comprising a first strain of *Listeria* for administration to a host, comprising substituting the first strain with a mutant *Listeria* strain, wherein the mutant *Listeria* strain is attenuated for entry into non-phagocytic cells relative to the first *Listeria* strain, but retains an ability to enter phagocytic cells. In some embodiments, the mutant strain is defective with respect to internalin B. In other embodiments, the mutant strain is defective with respect to both internalin B and ActA.

The invention also provides immunogenic compositions comprising the attenuated *Listeria* described herein. For instance, the invention provides an immunogenic composition comprising an attenuated *Listeria bacterium* which is attenuated for entry into non-phagocytic cells and comprises a nucleic acid molecule encoding a non-Listerial antigen. The invention further provides an immunogenic composition comprising an attenuated *Listeria bacterium* that is attenuated for entry into non-phagocytic cells and for cell-to-cell spread.

In addition, the invention provides an immunogenic composition comprising a mutant *Listeria* strain, wherein the mutant *Listeria* strain is attenuated for entry into non-phagocytic cells relative to a non-mutant *Listeria* strain, but retains an ability to enter phagocytic cells, and comprises a heterologous nucleic acid molecule encoding an antigen. In some embodiments, the strain is defective with respect to internalin B and comprises a heterologous nucleic acid molecule encoding an antigen. In other embodiments, the mutant strain is defective with respect to both internalin B and ActA.

The invention also provides a variety of vaccine compositions comprising the attenuated *Listeria* described herein. For instance, the invention provides a vaccine comprising (a) an attenuated *Listeria bacterium* which is attenuated for entry into non-phagocytic cells and comprises a nucleic acid molecule encoding a non-Listerial antigen, and (b) a pharmaceutically acceptable carrier and/or an adjuvant. The invention further provides a vaccine comprising (a) an attenuated *Listeria bacterium* that is attenuated for entry into non-phagocytic cells and for cell-to-cell spread, and (b) a pharmaceutically acceptable carrier and/or an adjuvant. The invention also provides a vaccine comprising (a) an attenuated *Listeria bacterium* which is attenuated for entry into non-phagocytic cells, and (b) a pharmaceutically acceptable carrier or an adjuvant. In some embodiments, the vaccines described herein comprise more than one type of attenuated *Listeria bacterium*. For instance, in some embodiments, the vaccine Comprises multiple different types of attenuated *Listeria*. The different types of attenuated *Listeria* may differ from each other with respect to the antigens they express and/or the nature of their modifications and mutations.

The present invention further provides a vaccine comprising a mutant *Listeria* strain, wherein the mutant *Listeria* strain is attenuated for entry into non-phagocytic cells relative to a non-mutant *Listeria* strain, but retains an ability to enter phagocytic cells. In some embodiments, the strain is defective with respect to internalin B. In other embodiments, the mutant strain in the vaccine is defective with respect to both internalin B and ActA. In some embodiments, the vaccine comprises more than one mutant *Listeria* strain, each of is attenuated for entry into non-phagocytic cells.

The term vaccine as used herein is intended to encompass a prophylactic vaccine, such as one given to induce an immune response prior to exposure to an agent encompassing an antigen in order to permit the individual to mount a stronger immune response upon exposure to that antigen, therefore increasing its ability to resist the agent or cells carrying the agent. The term vaccine is also intended to encompass a therapeutic vaccine, such as one administered to an individual that already has a disease associated with the vaccine antigen, wherein the vaccine can boost the individual's immune response to the antigen to provide an increased ability to combat the disease or cells carrying the antigen.

Methods of administration of such a vaccine composition are known in the art, and include in vitro, oral, intraveneous, intradermal, intraperitoneal, intramuscular, intralymphatic, intranasal and subcutaneous routes of administration. The vaccine compositions may further comprise additional components known in the art to improve the immune response to a vaccine, such as adjuvants or co-stimulatory molecules. For instance, co-stimulatory molecules comprise one or more factors selected from the group consisting of GM-CSF, IL-2, IL-12, IL-14, IL-15, B7.1, B7.2, and B7-DC are optionally included in the vaccine compositions of the present invention. Other co-stimulatory molecules are known to those of ordinary skill in the art.

Vaccine formulations are known in the art and may include numerous additives, such as preservatives, stabilizers, adjuvants, antibiotics, and other substances. Stabilizers, such as lactose or monosodium glutamate (MSG), are added to stabilize the vaccine formulation against a variety of conditions, such as temperature variations or a freeze-drying process. Vaccine formulations may also include a suspending fluid such as sterile water or saline. In some embodiments, the vaccine is a frozen or lyophilized formulation comprising one or more pharmaceutically acceptable excipients that are suitable for parenteral or oral administration. In other embodiments, the vaccine is a frozen or lyophilized formulation comprising one or more pharmaceutically acceptable excipients that are suitable for mucosal administration or administration as an aerosol.

The efficacy of the vaccines may be evaluated using in vivo models, for example a mouse model. Vaccines can be evaluated for their ability to provide either a prophylactic or therapeutic effect against a particular disease. For example, in the case of infectious diseases, a population of mice can be vaccinated with a desired amount of the appropriate vaccine of the invention, where the *bacterium* expresses an infectious disease associated antigen. This antigen can be from the *Listeria* itself or can be a heterologous antigen. The mice can be subsequently infected with the infectious agent related to the vaccine antigen and assessed for protection against infection. The progression of the infectious disease can be observed relative to a control population (either non-vaccinated or vaccinated with vehicle only or *Listeria* that does not express the appropriate antigen).

In the case of cancer vaccines, tumor cell models are available, where a tumor cell line expressing a desired tumor antigen can be injected into a population of mice either before (therapeutic model) or after (prophylactic model) vaccination with a *Listeria* involved in the invention containing the desired tumor-associated antigen or an antigen derived from a tumor-associated antigen. Vaccination with a *Listeria* containing the tumor antigen can be compared to control populations that are either not vaccinated, vaccinated with vehicle, or with a *Listeria* that does not express the desired antigen. The effectiveness of the vaccine in such models can be evaluated in terms of tumor volume as a function of time after tumor injection or in terms of survival populations as a function of time after tumor injection. Generally, the vaccine will result in a reduced tumor volume at most or all time points relative to a negative control (such as a non-vaccinated sample) and will result in a longer median survival.

In some embodiments of the invention, the tumor volume in those mice vaccinated with the mutant *Listeria* is less than or equal to the tumor volume of the control mice. In one embodiment, the tumor volume in mice vaccinated with mutant *Listeria* is at least approximately the same as the tumor volume in the control mice. In another embodiment, the tumor volume in mice vaccinated with mutant *Listeria* is at least about 10%, at least about 20%, at least about 30%, at least about 40% or at least about 50% less than the tumor volume in the control mice. In another embodiment, this differential in tumor volume is observed at least 7, 14, 30, or at least 60 days following the implant of the tumors into the mice. In one embodiment, the median survival time in the mice vaccinated with mutant *Listeria* is approximately the same as that in mice vaccinated with control *Listeria*. In another embodiment, the median survival time in the mice vaccinated with attenuated *Listeria* is at least about 1, at least about 3, or at least about 5 days longer than in mice vaccinated with control *Listeria*. In other embodiments, the median survival time in the mice vaccinated with attenuated *Listeria* is at least about 10 days, at least about 20 days, at least about 30 days longer than in mice vaccinated with control *Listeria*. In one embodiment of the invention, the vaccination with the mutant *Listeria* is done at a dose of *Listeria* that is approximately the same as the dose of control *Listeria*. In another embodiment, the vaccination of mutant *Listeria* is safely dosed at a level that is at least about 2, about 5, about 10, about $10^2$, about $10^3$, or at least about $10^4$ fold higher than the vaccination dose of control *Listeria*.

In addition to measurements of the efficacy of the vaccines, measurements of the safety and toxicity can also be made. Such methods of measuring safety can include determining the number of mutant *Listeria* entering hepatocytes as compared to non-mutant *Listeria*. In some embodiments, the mutant *Listeria* is defective with respect to internalin B. In other embodiments, the mutant *Listeria* is defective with respect to both internalin B and ActA.

In another aspect, the invention provides a method of decreasing the pathogenicity of a strain of *Listeria* used in a vaccine, comprising modifying the strain so as to decrease the ability of the strain to enter non-phagocytic cells, but substantially retain the ability of the strain to enter phagocytic cells. In some embodiments, the invention provides a method of decreasing the pathogenicity of a strain of *Listeria* used in a vaccine, comprising modifying the strain so as to make it defective with respect to internalin B. In some embodiments, the strain is further modified to be defective with respect to ActA.

In other aspects, the invention provides methods of making vaccines. For instance, the invention provides a method of making a vaccine comprising contacting attenuated *Listeria* (such as a mutant strain of *Listeria*) with a professional antigen-presenting cell, under suitable conditions and for a time sufficient to load the professional antigen-presenting cells, wherein the *Listeria* is attenuated for entry into non-phagocytic cells relative to a non-modified *Listeria* such as wild type (e.g., defective with respect to internalin B), but retains an ability to enter phagocytic cells, and comprises a heterologous nucleic acid molecule encoding an antigen. In still another aspect, the invention provides a professional antigen-presenting cell comprising a *Listeria bacterium*, wherein the *Listeria bacterium* is attenuated for entry into non-phagocytic cells. The invention also provides a professional antigen-presenting cell comprising a mutant *Listeria* strain, wherein the mutant *Listeria* strain is attenuated for entry into non-phagocytic cells relative to a non-mutant *Listeria* strain, but retains an ability to enter phagocytic cells. In some embodiments, the mutant *Listeria* is contacted with the professional antigen-presenting cell ex vivo or in viva. In some embodiments, the professional antigen-presenting cell is a dendritic cell. In other embodiments, the professional antigen-presenting cell is a macrophage. For descriptions of some exemplary antigens, see Section II.C, above.

IV. Methods of Inducing Immune Responses and Methods of Treatment

The present invention also provides methods of inducing immune responses and treating and/or preventing disease comprising the use of the attenuated *Listeria*, cells, compositions, and vaccines described herein. (Exemplary attenuated *Listeria* useful in the methods of the present invention are described in Section II.A-D, above, and in the Examples, below. Exemplary compositions, vaccines, and cells are described in Section III, above.)

For instance, the invention provides a method of inducing an immune response in a host to a non Listerial antigen comprising administering to the host an effective amount of a composition comprising a *Listeria bacterium* that is attenuated for entry into non-phagocytic cells and comprises a nucleic acid molecule encoding the non-Listerial antigen. The invention also provides a method of inducing an immune response in a host to an antigen comprising administering to the host an effective amount of a composition comprising a *Listeria bacterium* that is attenuated both for entry into non-phagocytic cells and for cell-to-cell spread, wherein the mutant *Listeria* strain comprises a nucleic acid encoding the antigen. The invention further provides a method of inducing an immune response in a host to an antigen, comprising administering to the host an effective amount of a vaccine comprising (a) a *Listeria* bacterium that is attenuated for entry into non-phagocytic cells, and (b) a pharmaceutically acceptable carrier and/or an adjuvant.

The invention also provides a method of inducing an immune response to an antigen in a host comprising administering to the host an effective amount of a composition comprising a mutant *Listeria* strain, wherein the mutant *Listeria* strain is attenuated for entry into non-phagocytic cells relative to a non-mutant *Listeria* strain, but retains an ability to enter phagocytic cells, and comprises a nucleic acid molecule encoding the antigen. The immune response may be a cell-mediated response. In one embodiment, the immune response is a CD8+ T-cell response. In another embodiment, the immune response is a CD4+ T-cell response. In still another embodiment, the immune response induced in the host comprises both a CD8+ and CD4+ T-cell response. For descriptions of some exemplary antigens, see Section II.C, above. In one embodiment the antigen is a tumor-associated antigen or derived from a tumor-associated antigen. In some embodiments, the mutant strain is defective with respect to internalin B. In other embodiments, the mutant strain is defective with respect to both internalin B and ActA.

In another aspect, the invention provides a method of inducing MHC class I antigen presentation on a professional antigen-presenting cell (in vitro, in vivo, or ex vivo) comprising contacting a mutant *Listeria* strain with the professional antigen-presenting cell, wherein the mutant *Listeria* strain is attenuated for entry into non-phagocytic cells relative to a non-mutant *Listeria* strain, but retains an ability to enter phagocytic cells, and comprises a heterologous nucleic acid molecule encoding an antigen comprising an MHC class I epitope. In some embodiments, the mutant strain is defective with respect to internalin B. In other embodiments, the mutant strain is defective with respect to both internalin B and ActA.

Additionally, the invention provides a method of inducing MHC class I antigen presentation or MHC class II antigen presentation on an antigen-presenting cell (either in vivo or in vitro), comprising contacting a *Listeria* bacterium with an antigen-presenting cell, wherein the *Listeria* bacterium is attenuated for entry into non-phagocytic cells and comprises a nucleic acid molecule encoding a non-Listerial antigen comprising an MHC class I epitope or an MHC class II epitope. The invention further provides a method of inducing MHC class II antigen presentation on a professional antigen-presenting cell (in vitro, in vivo, or ex vivo) comprising contacting a mutant *Listeria* strain with the professional antigen-presenting cell, wherein the mutant *Listeria* strain is attenuated for entry into non-phagocytic cells relative to a non-mutant *Listeria* strain, but retains an ability to enter phagocytic cells, and comprises a heterologous nucleic acid molecule encoding an antigen comprising an MHC class II epitope. In some embodiments, the mutant strain is defective with respect to internalin B. In other embodiments, the mutant strain is defective with respect to both internalin B and ActA.

The invention also provides a method of inducing an immune response in a host to an antigen comprising administering to the host an effective amount of a professional antigen presenting cell comprising an attenuated *Listeria* bacterium, wherein the attenuated *Listeria* bacterium is attenuated for entry into non-phagocytic cells and comprises a nucleic acid encoding the antigen.

The invention further provides a method of inducing an immune response in a host to an antigen, comprising the following steps: (a) contacting an attenuated *Listeria* bacterium with an antigen-presenting cell from the host, under suitable conditions and for a time sufficient to load the antigen-presenting cells, wherein the attenuated *Listeria* bacterium is attenuated for entry into non-phagocytic cells and comprises a nucleic acid molecule encoding the antigen; and (b) administering the antigen-presenting cell to the host. The invention also provides a method of inducing an immune response in a host to an antigen comprising the following steps: (a) contacting a mutant *Listeria* strain with a professional antigen-presenting cell from the host, under suitable conditions and for a time sufficient to load the antigen-presenting cells, wherein the mutant *Listeria* strain is attenuated for entry into non-phagocytic cells relative to a non-mutant *Listeria* strain, but retains an ability to enter phagocytic cells, and comprises a nucleic acid molecule encoding an antigen; and (b) administering the antigen-presenting cell to the host. In one embodiment, the antigen is a tumor-associated antigen or is derived from a tumor-associated antigen. In some embodiments, the mutant strain is defective with respect to internalin B. In other embodiments, the mutant strain is defective with respect to both internalin B and ActA.

In a further aspect, the invention provides a method of selectively delivering a heterologous protein into phagocytic cells in a host, comprising administering to the host a composition comprising a mutant *Listeria* strain that is attenuated for entry into non-phagocytic cells relative to a non-mutant *Listeria* strain, but substantially retains an ability to enter phagocytic cells, wherein the genome of the mutant *Listeria* strain comprises at least one mutation in at least one gene encoding an invasin, such as an internalin.

The invention further provides methods of preventing or treating disease (such as cancer, an infectious disease, or Listeriosis) in a host using the attenuated *Listeria* described herein. For instance, the invention provides a method of preventing or treating disease in a host comprising administering to the host an effective amount of a composition comprising an attenuated *Listeria* bacterium that is attenuated for entry into non-phagocytic cells and comprises a nucleic acid molecule encoding a non-Listerial antigen. The invention also provides a method of preventing or treating disease in host comprising administering to the host an effective amount of a composition comprising an attenuated *Listeria* bacterium which is attenuated both for entry into non-phagocytic cells and for cell-to-cell spread. The invention further provides a method of preventing or treating disease in a host, comprising administering to the host an effective amount of a vaccine comprising (a) an attenuated *Listeria* bacterium which is attenuated for entry into non-phagocytic cells, and (b) a pharmaceutically acceptable carrier and/or an adjuvant.

In one aspect, the present invention provides a method of preventing or treating disease in a host, comprising administering to the host a vaccine comprising a mutant *Listeria* strain, wherein the mutant *Listeria* strain is attenuated for entry into non-phagocytic cells relative to a non-mutant *Listeria* strain, but retains an ability to enter phagocytic cells. The disease is prevented or treated by the induction of a therapeutically beneficial immune response against an antigen related to the disease. In some embodiments, the mutant strain is defective with respect to internalin B. In other embodiments, the mutant strain is defective with respect to both internalin B and ActA. In one embodiment, the disease is cancer. In another embodiment, the disease is an autoimmune disease. In still other embodiments, the disease is an infectious disease or another disease caused by a pathogen such as a virus, bacterium, fungus, or protozoa.

The invention also provides a method of preventing or treating disease in a host comprising administering to the host an effective amount of a professional antigen-presenting cell comprising an attenuated *Listeria bacterium*, wherein the attenuated *Listeria bacterium* is attenuated for entry into non-phagocytic cells.

The invention further provides a composition comprising a *Listeria bacterium* for medical use, wherein the *Listeria bacterium* is attenuated for entry into non-phagocytic cells and comprises a nucleic acid molecule encoding a non-Listerial antigen. In another embodiment, the invention provides a *Listeria bacterium* for medical use, wherein the *Listeria bacterium* is attenuated for entry into non-phagocytic cells and comprises a nucleic acid molecule encoding a non-Listerial antigen.

The invention also provides a composition comprising a *Listeria bacterium* for medical use, wherein the *bacterium* is attenuated both for entry into non-phagocytic cells. The invention also provides a *Listeria bacterium* for medical use, wherein the *bacterium* is attenuated both for entry into non-phagocytic cells.

In addition, the invention provides a composition comprising a *Listeria bacterium* for medical use, wherein the *bacterium* is attenuated both for entry into non-phagocytic cells and for cell-to-cell spread. The invention also provides a *Listeria bacterium* for medical use, wherein the *bacterium* is attenuated both for entry into non-phagocytic cells and for cell-to-cell spread.

Additionally, the invention provides the use of a *Listeria bacterium* for the manufacture of a medicament for treatment of a disease unrelated to and/or not caused by *Listeria*, wherein the *Listeria bacterium* is attenuated for entry into non-phagocytic cells and comprises a nucleic acid molecule encoding a non-Listerial antigen. For instance, in some embodiments, the disease is cancer and the antigen is a tumor antigen or is an antigen derived from a tumor antigen.

The invention also provides the use of a *Listeria bacterium* for the manufacture of a medicament for treatment of a disease unrelated to and/or not caused by *Listeria*, wherein the *bacterium* is attenuated for entry into non-phagocytic cells. In some embodiments, the *Listeria bacterium* is further attenuated for cell-to-cell spread. In some embodiments, the disease is cancer and the antigen is a tumor antigen or is an antigen derived from a tumor antigen.

In some embodiments, the use of the attenuated *Listeria* in the prophylaxis or treatment of a cancer comprises the delivery of the attenuated *Listeria* to cells of the immune system of an individual to prevent or treat a cancer present or to which the individual has increased risk factors, such as environmental exposure and/or familial disposition. In some embodiments, the individual who is treated with the vaccine has had a tumor removed and/or has had cancer in the past.

The delivery of the attenuated *Listeria*, or a composition comprising the attenuated *Listeria*, may be by any suitable method, including, but not limited to, intradermal, subcutaneous, intraperitoneal, intravenous, intramuscular, intralymphatic, oral or intranasal. In some embodiments delivery of the attenuated *Listeria* is parenteral. In some embodiments, mucosal delivery is used.

In some embodiments, the compositions comprising the attenuated *Listeria* are administered to a host in combination with an immunostimulatory agent. The attenuated *Listeria* and the immunostimulatory agent can be administered simultaneously, sequentially or separately. Examples of immunostimulatory agents include, but are not limited to IL-2, IL-12, GMCSF, IL-15, B7.1, B7.2, and B7-DC and IL-14. In some embodiments, the immunostimulatory agent is an antibody or small molecule that targets T-cell regulatory molecules. For instance, in some embodiments, the immunostimulatory agent is CTLA-4 or BTLA-4. In some embodiments, the immunostimulatory agent is an agent that targets regulatory T-cells. For instance, the immunostimulatory agent used in conjunction with the attenuated *Listeria* may be an anti-CD25 antibody, an anti-LAG-3 antibody, or cytoxan.

The host in the methods described herein, is any vertebrate, preferably a mammal, including domestic animals, sport animals, and primates, and including humans.

The dosage of the pharmaceutical compositions or vaccines that are given to the host will vary depending on the species of the host, the size of the host, and the condition or disease of the host. The dosage of the compositions will also depend on the frequency of administration of the compositions and the route of administration. In some embodiments, a single dose comprises from about $10^2$ to about $10^{12}$ of the attenuated *Listeria* organisms. In another embodiment, a single dose comprises from about $10^6$ to about $10^{11}$ of the attenuated *Listeria* organisms. In still another embodiment, a single dose of the pharmaceutical composition or vaccine comprises from about $10^7$ to about $10^{10}$ of the attenuated organisms.

V. Kits

The invention further provides kits (or articles of manufacture) comprising the attenuated *Listeria* of the invention (as described above and in the Examples below).

In one aspect, the invention provides a kit comprising (a) a composition comprising a *Listeria bacterium*, wherein the *Listeria bacterium* is attenuated for entry into non-phagocytic cells and comprises a nucleic acid molecule encoding a non-Listerial antigen; and (b) instructions for the use of the composition in the prevention or treatment of a disease in a host. In some embodiments, the instructions are on a label on or in the kit. In other embodiments, the instructions are on an insert contained within the kit.

In another aspect, the invention provides a kit comprising (a) a composition comprising a *Listeria bacterium*, wherein the *Listeria bacterium* is attenuated for entry into non-phagocytic cells and comprises a nucleic acid molecule encoding a non-Listerial antigen; and (b) instructions for the administration of the composition to a host. In some embodiments, the instructions are on a label on or in the kit. In other embodiments, the instructions are on an insert contained within the kit, in some embodiments, the instructions are on a label on or in the kit. In other embodiments, the instructions are on an insert contained within the kit.

In still another aspect, the invention provides a kit comprising (a) a composition comprising the *Listeria bacterium*, wherein the *Listeria bacterium* is attenuated for entry into non-phagocytic cells; and (b) instructions for the use of the composition in the prevention or treatment of a disease in a host. In some embodiments, the *Listeria bacterium* is further attenuated for cell-to-cell spread. In some embodiments, the instructions are on a label on or in the kit. In other embodiments, the instructions are on an insert contained within the kit.

The invention further provides a kit comprising (a) a composition comprising the *Listeria bacterium*, wherein the *Listeria bacterium* is attenuated for entry into non-phagocytic cells: and (b) instructions for the administration of the composition to a host. In some embodiments, the *Listeria bacterium* is further attenuated for cell-to-cell spread. In some embodiments, the instructions are on a label on or in the kit. In other embodiments, the instruction are on an insert contained within the kit.

EXAMPLES

The following examples are provided to illustrate, but not to limit, the invention.

Example 1

Construction of Mutant *Listeria* Strains

A. Preparation of Mutant *Listeria* Strains.

*Listeria* strains were derived from 10403S (Bishop et al., *J. Immunol.* 139:2005 (1987)). *Listeria* strains with in-frame deletions of the indicated genes were generated by SOE-PCR and allelic exchange with established methods (Camilli, et al, *Mol. Microbiol.* 8:143 (1993)). The mutant strain LLO L461T (DP-L4017) was described in Glomski, et al, *J. Cell. Biol.* 156: 1029 (2002), incorporated by reference herein. The ΔactA mutant (DP-L4029) is the DP-L3078 strain described in Skoble et al., *J. of Cell Biology*, 150: 527-537 (2000), incorporated by reference herein in its entirety, which has been cured of its prophage. (Prophage curing is described in (Lauer et al., *J. Bacteriol.* 184:4177 (2002); U.S. Patent Publication No. 2003/0203472).) The LLO⁻ mutant (DP-L4027) (Lauer et al., *J. of Bacteriology*, 184:4177-4186 (2002)), and LLO Δ26 (DP-L4042) (Decatur et al, *Science* 290:992 (2000)) were also described previously. Construction of an ΔactAΔuvrAB strain is described in the copending U.S. provisional application No. 60/446,051, filed Feb. 6, 2003, as L4029/uvrAB (see, e.g. Example 7 of that application). DP-L4029uvrAB (also known as ΔactAΔuvrAB or actA⁻/uvrAB⁻) was deposited with ATCC Oct. 3, 2003, assigned PTA-5563.

B. Construction of pKSV7-dl inlB for Deletion of inlB from *Listeria* by Allelic Exchange.

Deletion of inlB from *Listeria* DP-L4029 (or from other selected mutant strains or from wild-type *Listeria*) can be effected by allelic exchange, as described by Camilli et al., *Mol. Microbiol.* 8:143-147 (1993). Splice Overlap Extension (SOE) PCR can be used to prepare the construct used in the allelic exchange procedure. The source of the internalin B gene is the sequence listed as Genbank accession number AL591975 (*Listeria monocytogenes* strain EGD, complete genome, segment 3/12; inlB gene region; nts. 97008-98963), incorporated by reference herein in its entirety, and/or the sequence listed as Genbank accession number NC_003210 (*Listeria monocytogenes* strain EGD, complete genome, inlB gene region: nts. 457008-458963), incorporated by reference herein in its entirety.

In the primary PCR reactions, approximately 1000 bps of sequence upstream and downstream from the *Listeria* inlB gene 5' and 3' ends, respectively, are amplified using the following template and primers:

Template: DP-L4056 or DP-L4029 genomic DNA

Primer pair 1 (For amplification of region upstream from 5' end of inlB):

```
Lm-96031F:
                                          (SEQ ID NO: 2)
5'-GTTAAGTTTCATGTGGACGGCAAAG
(Tm:72° C.)

Lm-(3' inlB-R +) 97020R:
```

-continued

```
                                          (SEQ ID NO: 3)
5'-AGGTCTTTTTCAGTTAACTATCCTCTCCTTGATTCTAGTTAT
(Tm: 114° C.)
```

(The underlined sequence complementary to region downstream of InlB carboxy terminus.)

Amplicon Size (bps): 1007

Primer pair 2 (For amplification of region downstream from 3' end of inlB):

```
Lm-(5' inlB-F +) 98911F:
                                          (SEQ ID NO: 4)
5'-CAAGGAGAGGATAGTTAACTGAAAAAGACCTAAAAAAGAAGGC
Tm: 118° C.)
```

(The underlined sequence complementary to region upstream of InlB amino terminus.)

```
Lm-99970R:
                                          (SEQ ID NO: 5)
5'-TCCCCTGTTCCTATAATTGTTAGCTC
(Tm:74° C.)
```

Amplicon size (bps): 1074

In the secondary PCR reaction, the primary PCR amplicons are fused through SOE PCR, taking advantage of complementarity between reverse primer from pair 1 and the forward primer of pair 2. This results in precise deletion of inlB coding sequence: nts. 97021-98910=1889 bps. The following template and primers were utilized in the secondary PCR reaction:

Template: Cleaned primary PCR reactions

Primer pair:

```
Lm-96043F:
                                          (SEQ ID NO: 6)
5'-GTGGACGGCAAAGAAACAACCAAAG
(Tm: 74° C.)

Lm-99964R:
                                          (SEQ ID NO: 7)
5'-GTTCCTATAATTGTTAGCTCATTTTTTTC
(Tm: 74° C.)
```

(Amplicon size (bps): 2033)

A protocol for completing the construction process is as follows:

The primary PCR reactions (3 temperature cycle) are performed using Vent DNA polymerase (NEB) and 10 μl of a washed 30° C. *Listeria* DP-L4056 OR DP-L4029 overnight culture. The expected size of *Listeria* amplicons by 1% agarose gel (1007 bps and 1074 bps). The primary PCR reactions are gel purified and the DNA eluted with GeneClean (BIO 101).

A secondary PCR reaction is performed, utilizing approximately equal amounts of each primary reaction as template (ca. 5 μl). The expected size of the *Listeria* amplicon from the secondary PCR reaction is verified by 1% agarose gel (2033 bps). Adenosine residue are added at the 3' ends of *Listeria* dl inlB amplicon with Taq polymerase.

The *Listeria* dl inlB amplicon is then inserted into a pCR2.1-TOPO vector. The pCR2.1-TOPO-dl inlB plasmid DNA is digested with XhoI and KpnI and the 2123 bp fragment is gel purified. The KnpI/XhoI 2123 bp fragment is inserted into a pKSV7 vector that has been prepared by digestion with KpnI and XhoI and treatment with CIAP (pKSV7-dl inlB). The fidelity of dl inlB sequence in pKSV7-dl inlB is then verified. The inlB gene is deleted from desired *Listeria* strains by allelic exchange with pKSV7-dl inlB plasmid.

C. Construction of Antigen-Expressing Strains.

Mutant *Listeria* strains expressing a truncated form of a model antigen ovalbumin (OVA), the immunodominant epitope from mouse colorectal cancer (CT26) known as AH1 (SPSYVYHQF (SEQ ID NO:8)), and the altered epitope AH1-A5 (SPSYAYHQF (SEQ ID NO:9); Slansky et al., *Immunity*, 13:529-538 (2000)) were prepared. The pPL2 integrational vector (Lauer et al., *J. Bacteriol*. 184:4177 (2002); U.S. Patent Publication No. 2003/0203472) was used to derive OVA and AH1-A5/OVA recombinant *Listeria* strains containing a single copy integrated into an innocuous site of the *Listeria* genome.

i. Construction of OVA-Expressing *Listeria* (DP-L4056).

An antigen expression cassette consisting of hemolysin-deleted LLO fused with truncated OVA and contained in the pPL2 integration vector (pPL2/LLO-OVA) is first prepared. The *Listeria*-OVA vaccine strain is derived by introducing pPL2/LLO-OVA into the phage cured *L. monocytogenes* strain DP-L4056 at the PSA (Phage from ScottA) attachment site tRNA$^{Arg}$-attBB'.

PCR is used to amplify the hemolysin-deleted LLO using the following template and primers:
Source: DP-L4056 genomic DNA
Primers:
Forward (KpnI-LLO nts. 1257-1276):

(SEQ ID NO: 10)
5'-CTCTGGTACCTCCTTTGATTAGTATATTC
($T_m$: LLO-spec: 52° C. Overall: 80° C.)

Reverse (BamHI-XhoI-LLO nts. 2811-2792):

(SEQ ID NO: 11)
5'-CAATGGATCCCTCGAGATCATAATTTACTTCATCCC
($T_m$: LLO-spec: 52° C. Overall: 102° C.)

PCR is also used to amplify the truncated OVA using the following template and primers:
Source: pDP3616 plasmid DNA from DP-E3616 *E. coli* (Higgins et al., *Mol. Molbiol*. 31:1631-1641 (1999)).
Primers:
Forward (XhoI-NcoI OVA cDNA nts. 174-186):

(SEQ ID NO: 12)
5'-ATTTCTCGAGTCCATGGGGGGTTCTCATCATC
($T_m$: OVA-spec: 60° C. Overall: 88° C.)

Reverse (XhoI-NotI-HindHIII):

(SEQ ID NO: 13)
5'-GGTGCTCGAGTGCGGCCGCAAGCTT
($T_m$: Overall: 82° C.)

One protocol for completing the construction process involves first cutting the LLO amplicon with KpnI and BamHI and inserting the KpnI/BamHI vector into the pPL2 vector (pPL2-LLO). The OVA amplicon is then cut with XhoI and NotI and inserted into the pPL2-LLO which has been cut with XhoI/NotI, (Note: The pPL2 vector does not contain any XhoI sites; pDP-3616 contains one XhoI site, that is exploited in the OVA reverse primer design.) The construct pPL2/LLO-OVA is verified by restriction analysis (KpnI-LLO-XhoI-OVA-NotI) and sequencing. The plasmid pPL2/LLO-OVA is introduced into *E. coli* by transformation, followed by introduction and integration into *Listeria* (DP-L4056) by conjugation, exactly as described by Lauer et al. (or into another desired strain of *Listeria*, such as an ΔinlB mutant or an ΔactAΔinlB double mutant).

A description of the insertion of an antigen expression cassette that expresses OVA can also be found in Example 8 of the U.S. provisional application entitled "Free-Living Microbe Based Vaccine Compositions", U.S. Ser. No. 60/511,869, filed Oct. 15, 2003.

ii. Construction of *Listeria* Strains Expressing AH1/OVA or AH1-A5/OVA.

To prepare *Listeria* expressing either the AH1/OVA or the AH1-A5/OVA antigen sequences, inserts bearing the antigen are first prepared from oligonucleotides and then ligated into the vector pPL2-LLO-OVA (prepared as described above).

The following oligonucleotides are used in preparation of the AH1 or AH1-A5 insert:
AH1 epitope insert (ClaI-PstI compatible ends):
Top strand oligo (AH1 Top):

(SEQ ID NO: 14)
5'-CGATTCCCCTAGTTATGTTTACCACCAATTTGCTGCA

Bottom strand oligo (AH1 Bottom):

(SEQ ID NO: 15)
5'-GCAAATTGGTGGTAAACATAACTAGGGGAT

AH1-A5 epitope insert (ClaI-AvaII compatible ends):
The sequence of the AH1-A5 epitope is (SEQ ID NO: 9)
SPSYAYHQF (SEQ ID NO: 16)
(5'-CCA AGT TAT GCA TAT CAT CAA TTT-3').

Top:
(SEQ ID NO): 17)
5'-CGATAGTCCAAGTTATGCATATCATCAATTTGC

Bottom:
(SEQ ID NO: 18)
5'-GTCGCAAATTGATGATATGCATAACTTGGACTAT

The oligonucletide pair for a given epitope are mixed together at an equimolar ratio, heated at 95° C. for 5 min. The oligonucleotide mixture is then allowed to slowly cool. The annealed oligonucleotide pairs are then ligated at a 200 to 1 molar ratio with pPL2-LLO/OVA plasmid prepared by digestion with the relevant restriction enzymes. The identity of the new construct can be verified by restriction analysis and/or sequencing.

The plasmid can then be introduced into *E. coil* by transformation, followed by introduction and integration into *Listeria* (DP-L4056) by conjugation, exactly as described by Lauer et al. (or into another desired strain of *Listeria*, such as an ΔinlB mutant or an ΔactAΔinlB double mutant).

Example 2

*Listeria* Pathogenicity Studies

The median lethal dose ($LD_{50}$) of the some of the mutant *Listeria* strains was determined by IV infection of mice. Three to five female C57BL/6 micer were infected IV with three 5-fold dilutions of the indicated strain. The mice were monitored daily for 10 days and sacrificed when they showed signs of distress. The median lethal dose was calculated. The data is shown in Table 1, below. The results show that the mutant *Listeria* strains that are deficient with respect to internalin B (ΔinlB, ΔactAΔinlB, and ΔactAΔinlAB) are less toxic when combined with an actA deletion. The ΔinlB only strain shows toxicity similar to wild-type *Listeria*.

TABLE 1

Attenuated *Listeria monocytogenes* strains

| Strain | Genotype | Phenotype | Pathogenicity $LD_{50}$ (cfu) in C57BL/6 mice Parental |
|---|---|---|---|
| DP-L4056 | Wild type; 10403S, phage free | Wild-type | $1 \times 10^5$ |
| DP-L4406 | ΔinlB | Impaired inlB-mediated infection | $1 \times 10^5$ |
| DP-L4029 | ΔactA | Defective cell-to-cell spread | $1 \times 10^8$ |
|  | ΔactAΔinlB | No host actin nucleation; defective cell-to-cell spread; impaired inlB-mediated infection | $1 \times 10^8$ |
|  | ΔactAΔinlAB |  | $1 \times 10^9$ |

Example 3

Assessment of In Vivo Cytotoxic Activity in Mice Vaccinated with *Listeria* Monocytogenes A series of studies were done to assess the ability of vaccinated mice to lyse antigen specific target cells in vivo. In the first study, Balb/c mice were vaccinated either intraveneously (IV) or intramuscularly (IM) with *Listeria monocytogenes* strains DP-L4029 (ΔactA), DP-L4029 ΔinlB (ΔactAΔinlB) and the same strains engineered to express AH1-A5 according to Table 2. The *Listeria* constructs expressing AH1-A5 also express hemolysin-deleted LLO and truncated OVA (see Example 1.C, above). The vaccination dose was 0.1 $LD_{50}$. A target cell population was prepared by harvesting the spleens of 10 naïve Balb/c mice in RPMI 1640 medium. The cells were dissociated and the red cells lysed. The white blood cells were counted and split into two equal populations. Each group was pulsed with a specific peptide, either target (AH1, SPSYVYHQF (SEQ ID NO:8), from SynPep, Dublin, Calif.) or control (β-gal, TPHPARIGL (SEQ ID NO:19)), at 0.5 µg/ml, for 90 minutes at 37° C. Cells were then washed 3 times in medium, and twice in PBS+0.1% BSA. Cells were resuspended at $1 \times 10^7$ per mL in warm PBS+0.1% BSA (10 mL or less) for labeling with carboxyfluorescein diacetate succinlmidyl ester (CFSE, Molecular Probes, Eugene, Oreg.). To the target cell suspension, 1.25 µL of a 5 mM stock of CFSE was added and the sample mixed by vortexing. To the control cell suspension, a ten-fold dilution of the CFSE stock was added and the sample mixed by vortexing. The cells were incubated at 37° C. for 10 minutes. Staining was stopped by addition of a large volume (>40 mL) of ice-cold PBS. The cells were washed twice at room temperature with PBS, then resuspended and counted. Each cell suspension was diluted to $50 \times 10^6$ per mL, and 100 µL of each population was mixed and injected via the tail vein of either naïve or vaccinated mice 6 days after vaccination. After 12-24 hours, the spleens were harvested and a total of $5 \times 10^6$ cells were analyzed by flow cytometry. The high (target) and low (control) fluorescent peaks were enumerated, and the ratio of the two was used to establish the percentage of target cell lysis relative to the HBSS control population. The results are shown in Table 2 and FIG. 1A. (The tables in this Example indicate the averages of the three mice, whereas the figures show representative histograms individual mice.) The vaccination using ΔactAΔinlB vs. using ΔactA shows an improvement in the antigen specific in vivo cytotoxicity when administered IV but not IM.

TABLE 2

In vivo cytotoxicity (% kill of target cells relative to a non vaccinated control sample) of Balb/c mice vaccinated as indicated.

| Immunization | # of mice | Vaccination dose | % kill of target cells |
|---|---|---|---|
| HBSS | 3 | 100 µL IV | 0 |
| ΔactA | 3 | $5 \times 10^6$ in 100 µL IV | −0.1 |
| ΔactA AH1-A5 | 3 | $5 \times 10^6$ in 100 µL IV | 11.5 |
| ΔactAΔinlB | 3 | $1 \times 10^7$ in 100 µL IV | 1.7 |
| ΔactAΔinlB AH1-A5 | 3 | $1 \times 10^7$ in 100 µL IV | 23.5 |
| ΔactA | 3 | $5 \times 10^6$ in 100 µL IM | 1.5 |
| ΔactA AH1-A5 | 3 | $5 \times 10^6$ in 100 µL IM | 8.5 |
| ΔactAΔinlB | 3 | $1 \times 10^7$ in 100 µL IM | 2.8 |
| ΔactAΔinlB AH1-A5 | 3 | $1 \times 10^7$ in 100 µL IM | 8.7 |

Another study was done using the ΔactA as well as ΔactAΔinlB double mutant, both strains expressing AH1-A5, vaccinating IV according to Table 3. In this study, the naïve spleen cells were pulsed with β-gal, AH1, or P60-217 (KYGVSVQDI (SEQ ID NO:20), a *Listeria* specific control). The β-gal pulsed cells were labeled with low CFSE, the AH1 and P60-217 with high CFSE. Two mice of each set were injected at day 5 with β-gal and AH-1 pulsed cells as above. The remaining two of each set were injected at day 5 with β-gal and P60-217 pulsed cells. The results are shown in Table 3 and FIG. 1B.

TABLE 3

In vivo cytotoxicity (% kill of target cells relative to a non vaccinated control sample) of Balb/c mice vaccinated as indicated.

| Immunization | # of mice | Vaccination dose | Target | % kill |
|---|---|---|---|---|
| HBSS | 2 | 100 µL | P60-217 | 0 |
| ΔactA AH1-A5 | 2 | $5 \times 10^6$ in 100 µL | P60-217 | 62.4 |
| ΔactAΔinlB AH1-A5 | 2 | $1 \times 10^7$ in 100 µL | P60-217 | 42.0 |
| HBSS | 2 | 100 µL | AH1 | 0 |
| ΔactA AH1-A5 | 2 | $5 \times 10^6$ in 100 µL | AH1 | 19.7 |
| ΔactAΔinlB AH1-A5 | 2 | $1 \times 10^7$ in 100 µL | AH1 | 28.0 |

Another study was done using ΔactAΔinlB double mutant with or without AH1-A5, vaccinating IV according to Table 4. In this study, the naïve spleen cells were pulsed with β-gal, AH1, or AH1-A5 (SPSYAYHQF (SEQ ID NO:9)). The β-gal pulsed cells were labeled with low CFSE, the AH1 and AH1-A5 with high CFSE. Three mice of each set were injected at day 6 with β-gal and AH-1 pulsed cells as above. The remaining three of each set were injected at day 6 with β-gal and AH1-A5 pulsed cells. The results are shown in Table 4 and FIG. 1C.

TABLE 4

In vivo cytotoxicity (% kill of target cells relative to a non vaccinated control sample) of Balb/c mice vaccinated as indicated.

| Immunization | # of mice | Vaccination dose | Target | % kill |
|---|---|---|---|---|
| HBSS | 3 | 100 µL | AH1 | 0 |
| ΔactAΔinlB | 3 | $1 \times 10^7$ in 100 µL | AH1 | 0.7 |
| ΔactAΔinlB AH1-A5 | 3 | $1 \times 10^7$ in 100 µL | AH1 | 31.8 |
| HBSS | 3 | 100 µL | AH1-A5 | 0 |
| ΔactAΔinlB | 3 | $1 \times 10^7$ in 100 µL | AH1-A5 | 5.7 |
| ΔactAΔinlB AH1-A5 | 3 | $1 \times 10^7$ in 100 µL | AH1-A5 | 94.9 |

Example 4

Therapeutic Vaccination with *Listeria monocytogenes* ΔactAΔinlB Double Mutant

Using Balb/c mice, CT26 tumor cells (ATCC CRL-2639) were injected into the mice ($2 \times 10^5$ in 100 µL in HBSS) to establish lung metastases. The CT26 cells are a murine colon adenocarcinoma that express the MMTV gp70 epitope AH1. (The cells were further modified to express a human tumor antigen, although this characteristic is not relevant to the data presented here.) Several studies were done to assess the use of *Listeria monocytogenes* ΔactAΔinlB as an effective therapeutic vaccine strain. In one study, *Listeria monocytogenes* strains ΔactA, ΔactA modified to express AH1-A5, and ΔactAΔinlB modified to express AH1-A5 were used for vaccinating groups of thirteen mice. All strains were grown in BHI medium (Brain Heart Infusion, Fisher Scientific) at 37° C. at 300 rpm and stored frozen prior to use. The frozen stock of each strain was diluted into HBSS and the mice were vaccinated intraveneously with $1 \times 10^7$ CFU in 100 µL for each strain four days after the tumor implant, as well as with 100 µL HBSS control. Twenty days post tumor implant, three mice per group were sacrificed and the lungs harvested (shown in FIG. 2A).

Figure 2B:
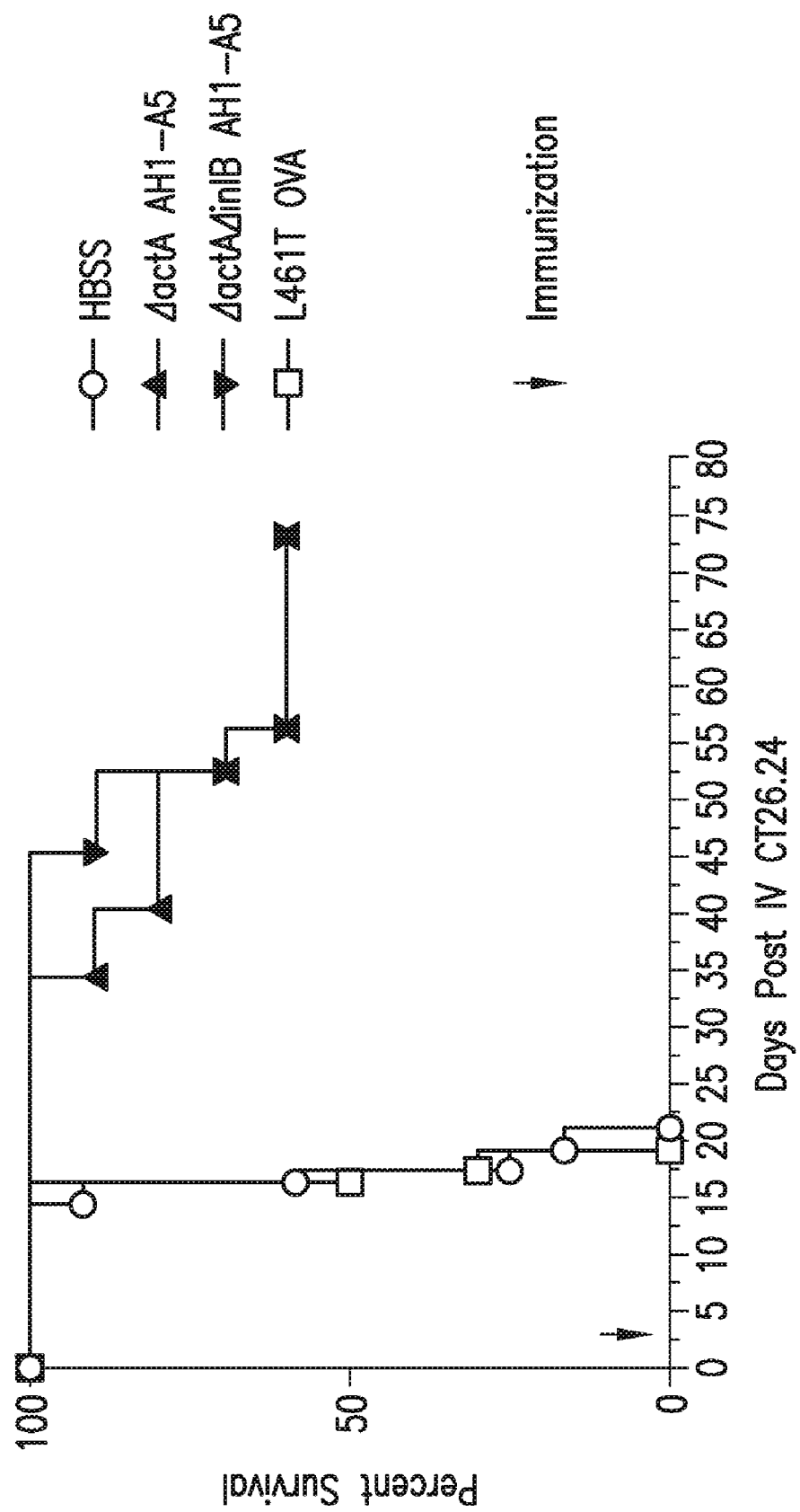
Figure 2C:
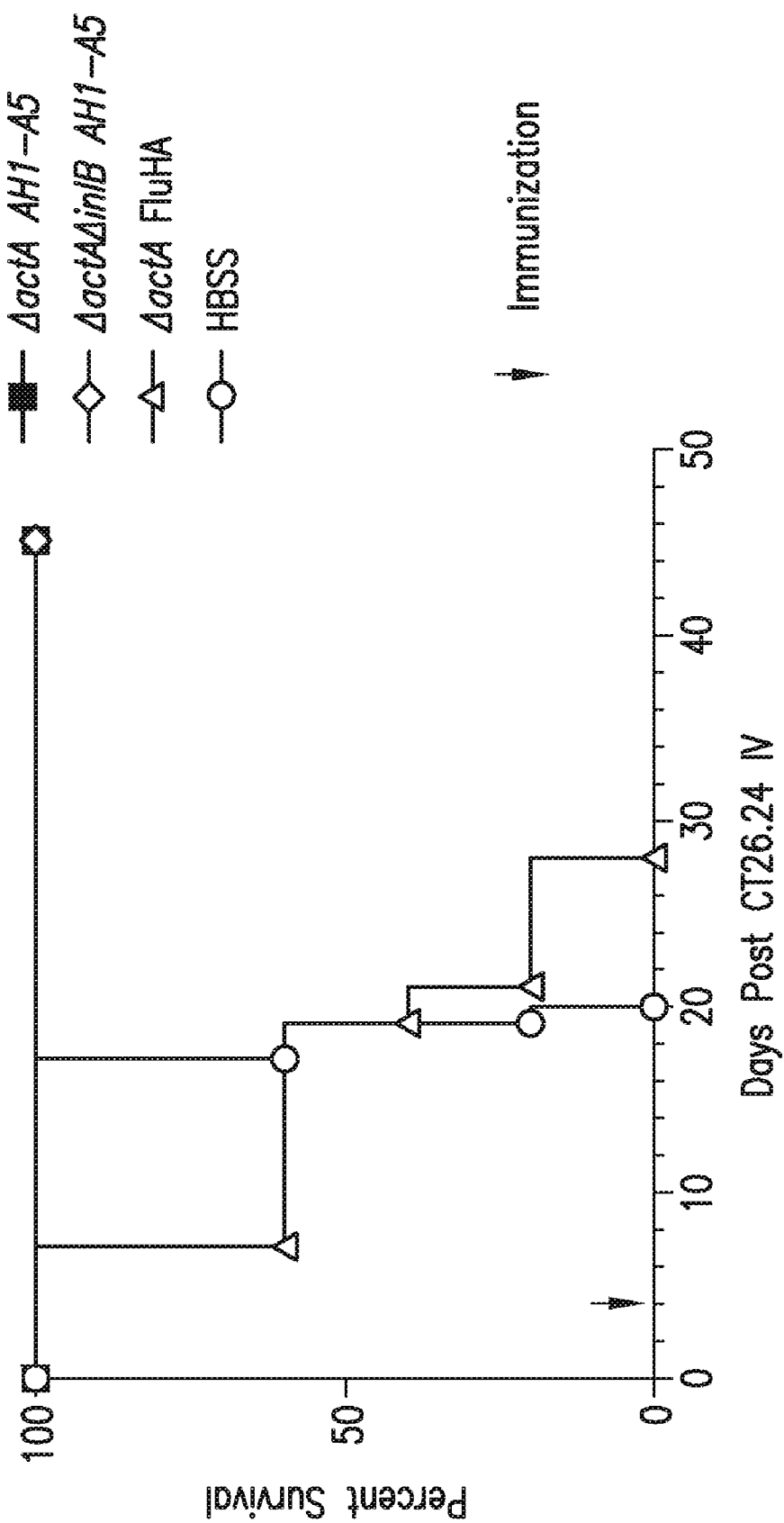
Figure 3A:
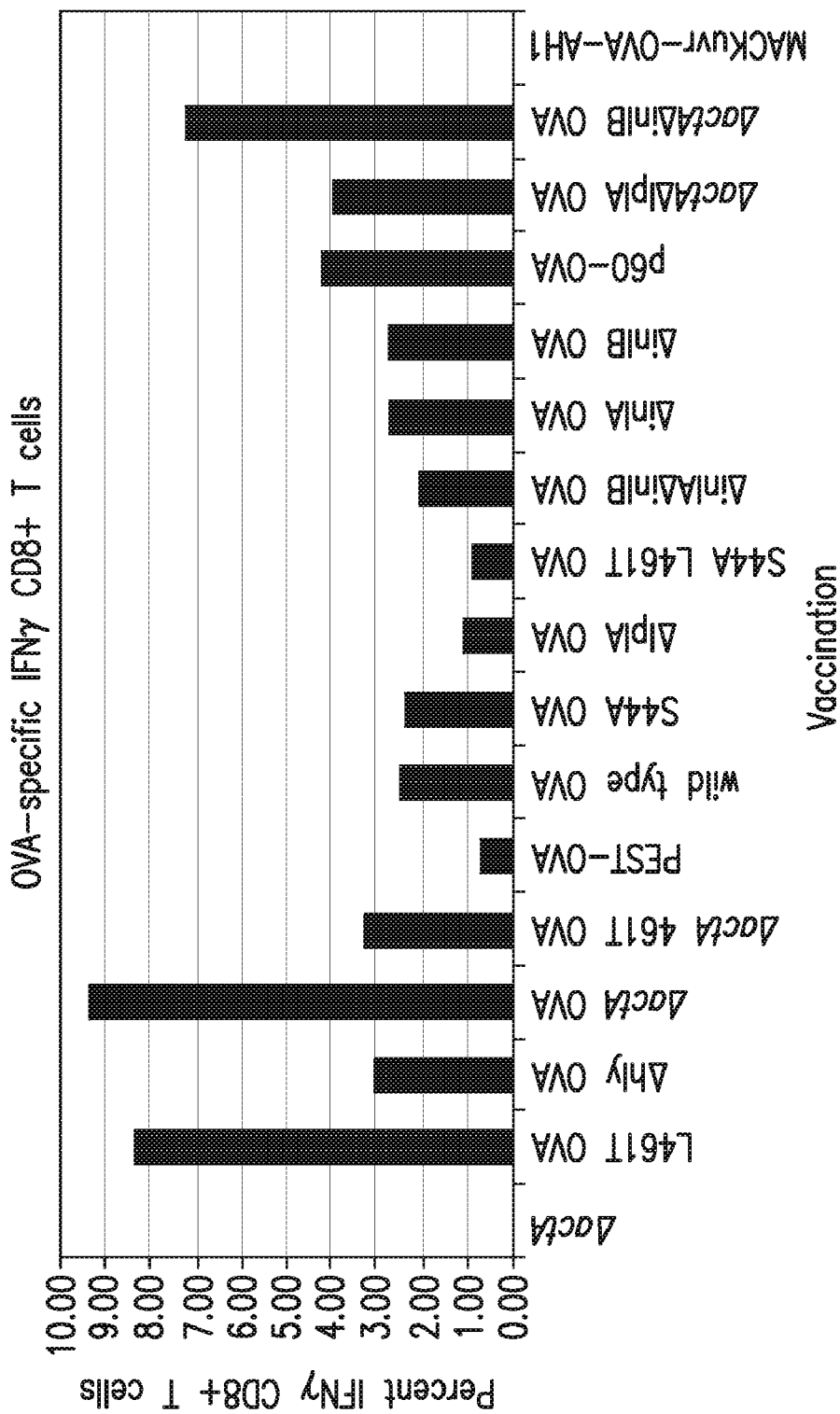
FIGS. 3A-3F show the results of IFN-γ and TNF-α intracellular Cytokine Staining (ICS) assays for splenic CD8+ T cells from mice vaccinated with mutant Listeria, stimulated with SL8 $OVA_{257-264}$ peptide (FIGS. 3A-B), $LLO_{190}$ peptide (FIGS. 3C-D), or the $LLO_{296}$ peptide (FIGS. 3E-F). ("PCT" indicates data for the S-59/UVA inactivated cells.)
Figure 3B:
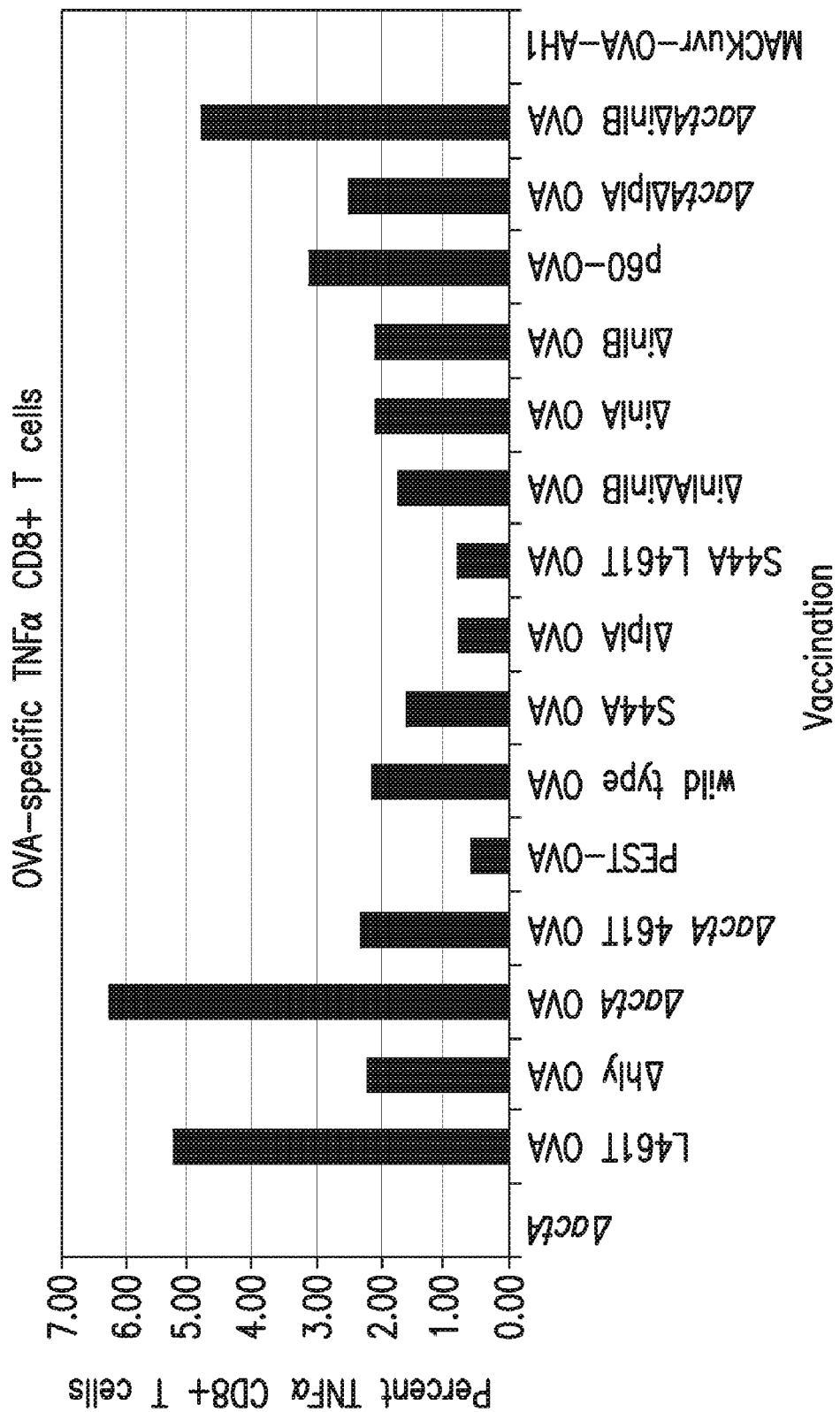
Figure 3C:
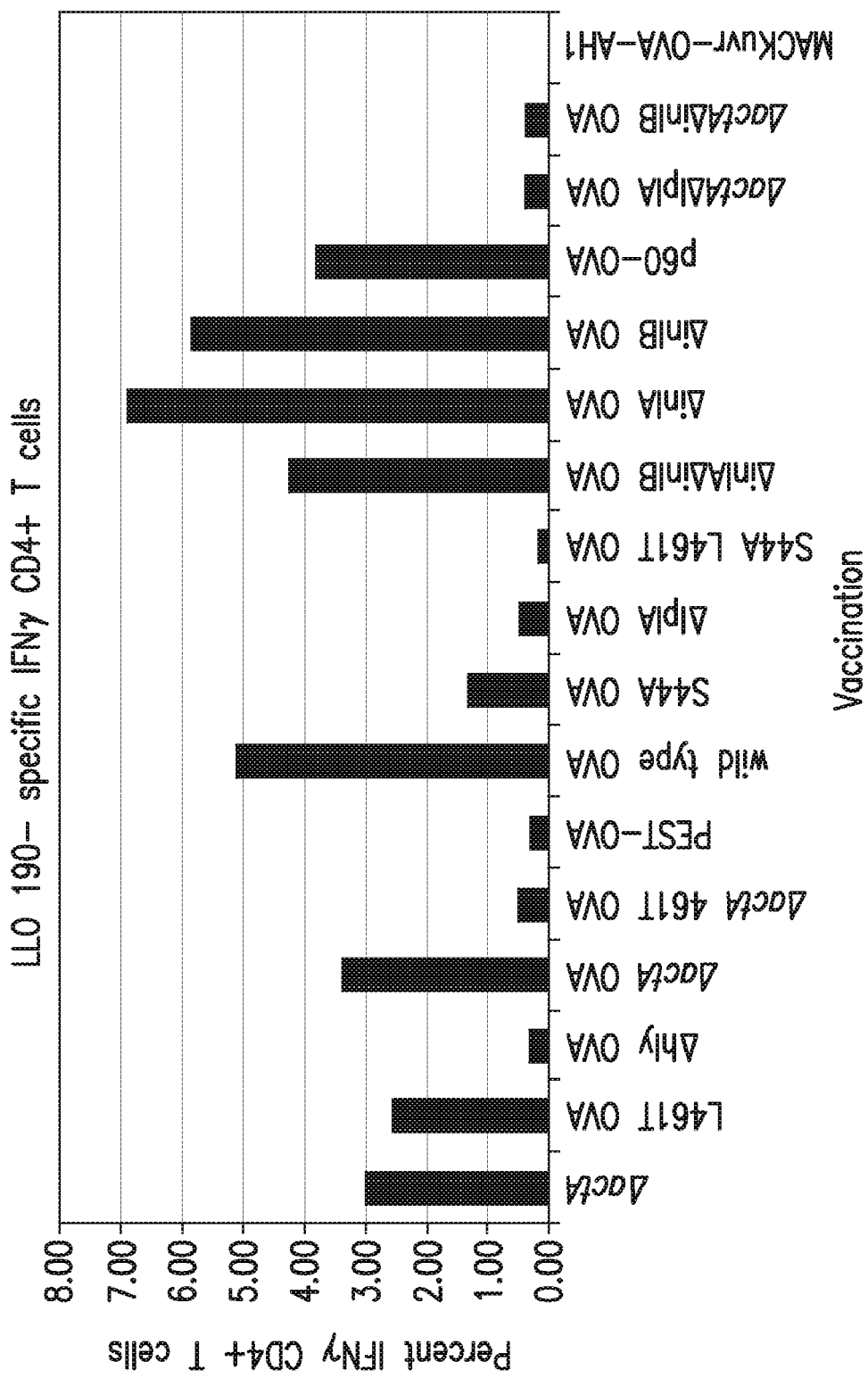
Figure 3D:
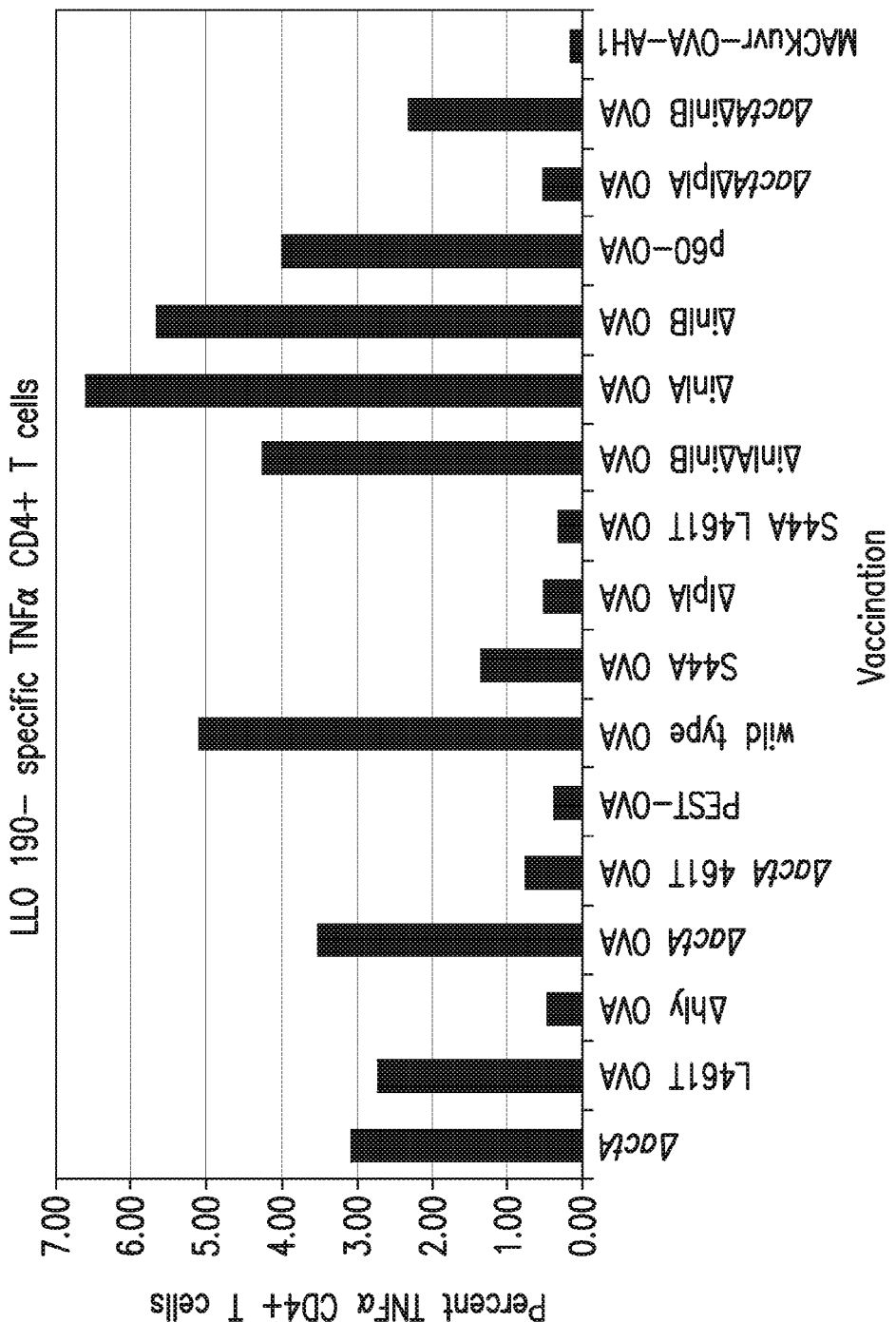
Figure 3E:
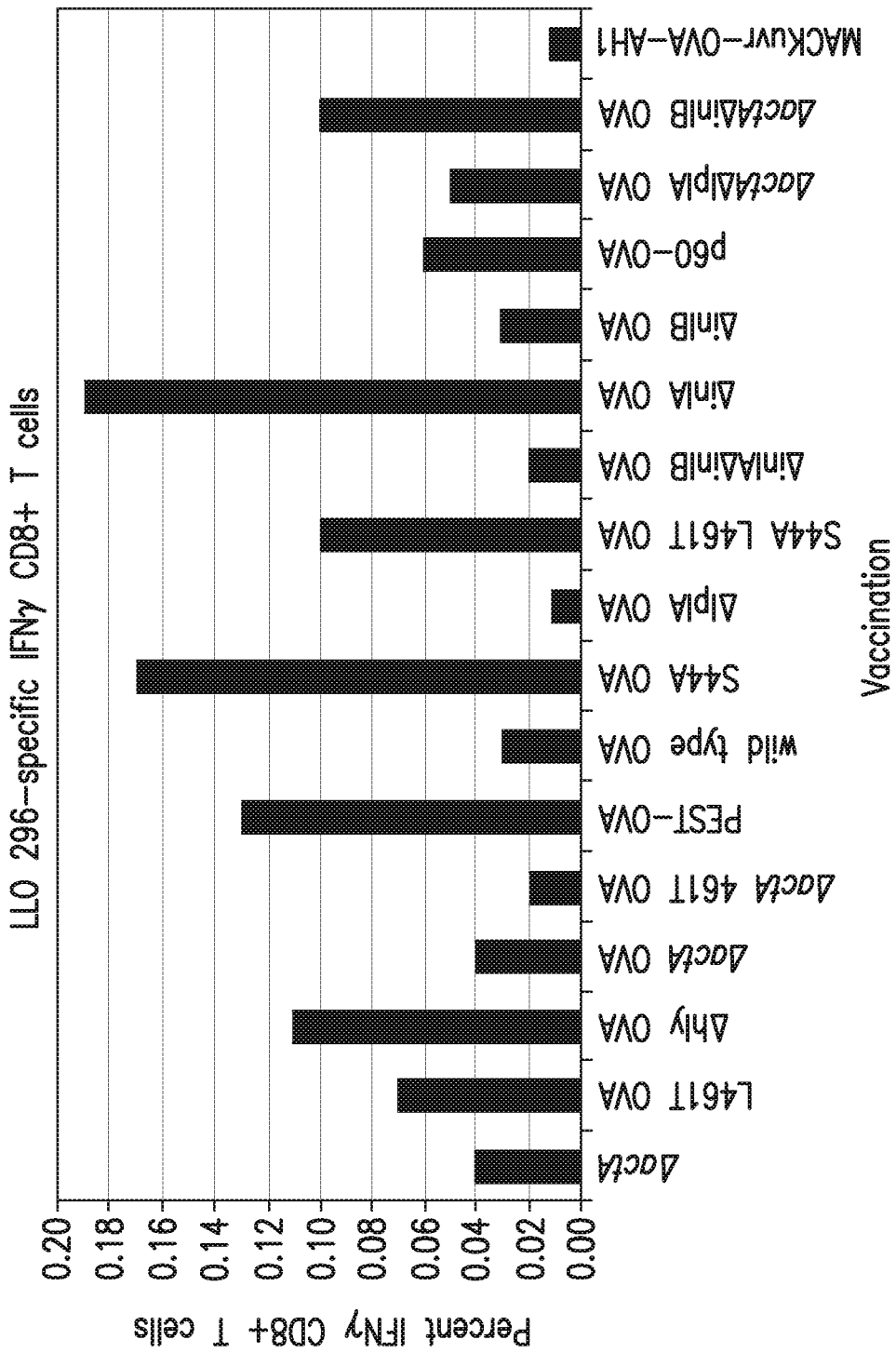
Figure 3F:
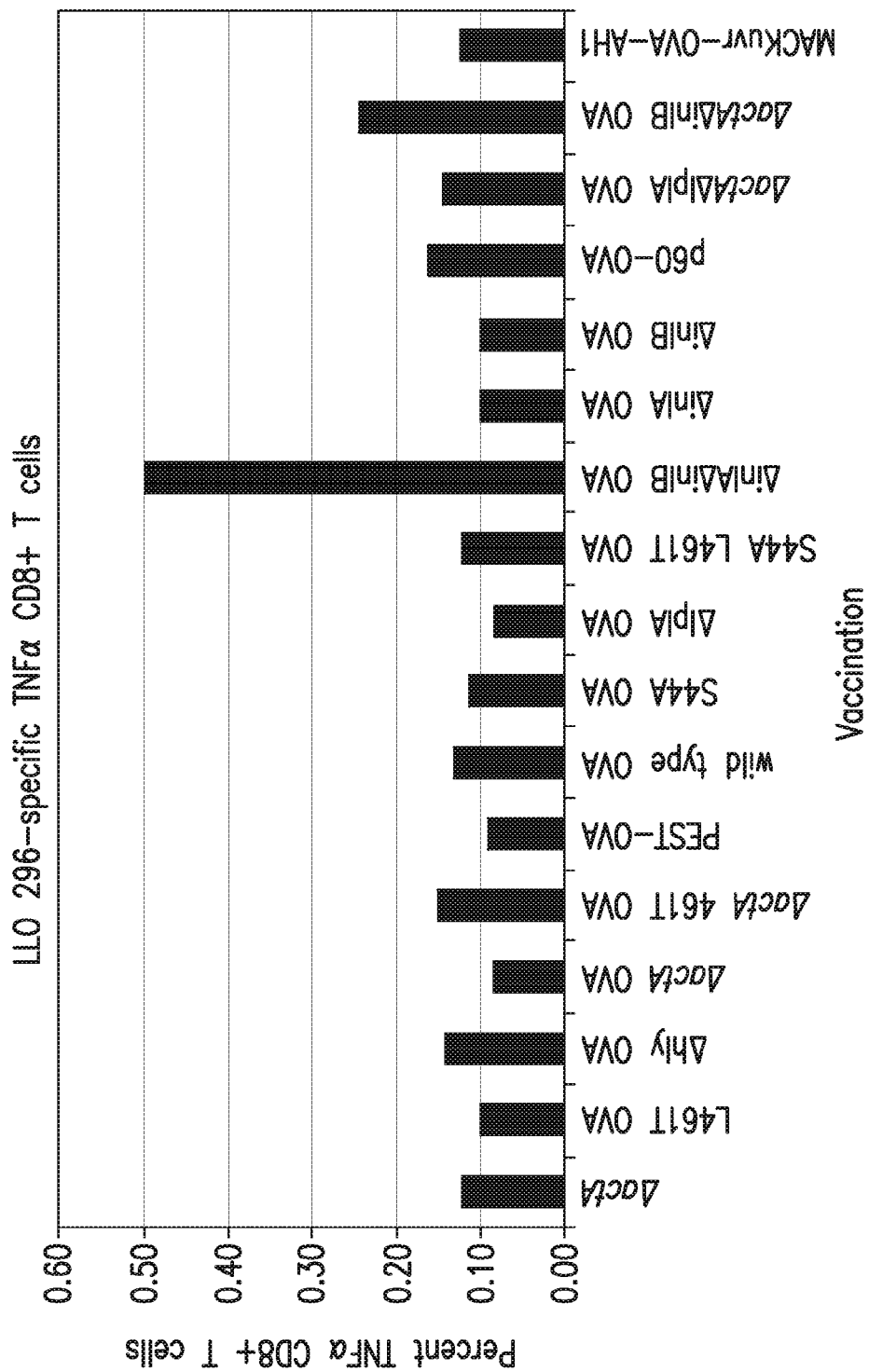

The remaining ten mice per group were monitored for survival (data not shown). Additional studies were done on groups of ten mice (survival only, lungs were not harvested from any of the mice) using ΔactA AH1-A5, and ΔactAΔinlB AH1-A5 as well as L461T expressing OVA as an irrelevant antigen control in one study and ΔactA expressing FluHA as an irrelevant antigen in another study. The survival results for these studies are shown in FIGS. 2B and 2C, respectively. The AH1 antigen is endogenous to the mice, such that any immunization effect would be breaking immune tolerance in the mice. The results indicate that the ΔactAΔinlB mutant is an effective vaccine that breaks tolerance in this model and significantly enhances survival in tumor bearing mice.

Example 5

Immunogenicity of Various Strains of *Listeria monocytogenes* Following Intramuscular Administration C57BL/6 mice (3 per group) were injected 1M with 100 µL HMS containing 0.1 $LD_{50}$ of *Listeria monocytogenes* strains indicated in Table 5. All strains were grown in BHI medium (Brain Heart Infusion, Fisher Scientific) at 37° C. at 300 rpm and stored frozen prior to use. The mice were sacrificed 7 days after vaccination and the spleens were harvested and assessed by Intracellular Cytokine Staining (ICS).

For ICS, spleen cells from vaccinated and control groups of mice were incubated with SL8 $OVA_{257-264}$ peptide (SL8 OVA antigen, SIINFEKL (SEQ ID NO:21), Invitrogen, San Diego, Calif.) which stimulates OVA specific CD8+ cells, $LLO_{190}$ (NEKYAQAYPNVS (SEQ ID NO:22), Invitrogen) an MHC class II epitope for listeriolysin O (*Listeria* antigen), or $LLO_{296}$ (VAYGRQVYL (SEQ ID NO:23), Invitrogen), an MHC class I epitope for listeriolysin O, for 5 hours in the presence of Brefeldin A (Pharmingen). The Brefeldin A inhibits secretion of the cytokines produced upon stimulation of the T cells. Spleen cells incubated with an irrelevant MHC class I peptide were used as controls. PMA (phorbol-12-myristate-13-acetate, Sigma) 20 ng/mL and ionomycin (Sigma) 2 µg/mL stimulated spleen cells were used as a positive control for IFN-γ and TNF-α intracellular cytokine staining. For detection of cytoplasmic cytokine expression, cells were stained with FITC-anti-CD4 mAb (RM 4-5) and PerCP-anti-CD8 mAb (53-6.7), fixed and permeabilized with Cytofix/CytoPerm solution (Pharmingen), and stained with PE-conjugated anti-TNF-α mAb (MP6-XT22) and APC-conjugated anti-IFN-γ mAb (XMG1.2) for 30 minutes on ice. The percentage of cells expressing intracellular IFN-γ and/or TNF-α was determined by flow cytometry (FACScalibur, Becton Dickinson, Mountain View, Calif.) and data analyzed using CELLQuest software (Becton Dickinson Immunocytometry System). As the fluorescent labels on the various antibodies can all be distinguished by the FACScalibur, the appropriate cells were identified by gating for those CD8+ and CD4+ that were stained with either or both of the anti-IFN-γ or anti-TNF-α. The results are indicated in FIGS. 3A-F. The ΔactAΔinlB strain is one of the more effective strains at eliciting an OVA specific immune response.

TABLE 5

Vaccination of C57BL/6 mice with various strains of *Listeria monocytogenes*.

| Vaccination strain | Description | Vaccination dose |
|---|---|---|
| DP-L4029 | ΔactA | $1 \times 10^7$ |
| DP-L4017 OVA | L461T LLO mutant, expresses OVA | $7.5 \times 10^6$ |
| DP-L4027 OVA | Δhl⁻ (LLO⁻) mutant, expresses OVA | $1 \times 10^8$ |
| DP-L4029 OVA | ΔactA mutant, expresses OVA | $1 \times 10^7$ |
| DP-L4038 OVA | ΔactA L461T double mutant, expresses OVA | $2 \times 10^7$ |
| DP-L4042 OVA | LLO Δ26 (PEST⁻) mutant, expresses OVA | $5 \times 10^7$ |
| DP-L4056 OVA | Wild type, expresses OVA | $5 \times 10^4$ |
| DP-L4097 OVA | S44A LLO mutant, expresses OVA | $1 \times 10^7$ |
| DP-L 4364 OVA | Δlpl mutant, expresses OVA | $2 \times 10^7$ |
| DP-L4384 OVA | LLO S44A/L461T double mutant, expresses OVA | $5 \times 10^7$ |

TABLE 5-continued

Vaccination of C57BL/6 mice with various strains of Listeria monocytogenes.

| Vaccination strain | Description | Vaccination dose |
|---|---|---|
| DP-L4404 OVA | ΔinlAΔinlB double mutant, expresses OVA | $5 \times 10^4$ |
| DP-L4405 OVA | ΔinlA mutant, expresses OVA | $5 \times 10^4$ |
| DP-L 4406 OVA | ΔinlB mutant, expresses OVA | $1 \times 10^5$ |
| P60-LLO OVA | ΔP60 mutant, expresses OVA | $1 \times 10^6$ |
| DP-L4029 lplA⁻ OVA | ΔactAΔlplA double mutant, expresses OVA | $2 \times 10^8$ |
| DP-L4029 ΔinlB OVA | ΔactAΔinlB double mutant, expresses OVA | $1 \times 10^8$ |
| MACKuvr⁻ LLO OVA/AH1 | Δuvr mutant, expresses OVA/AH1 | $2 \times 10^5$ |

Example 6

Figure 4:
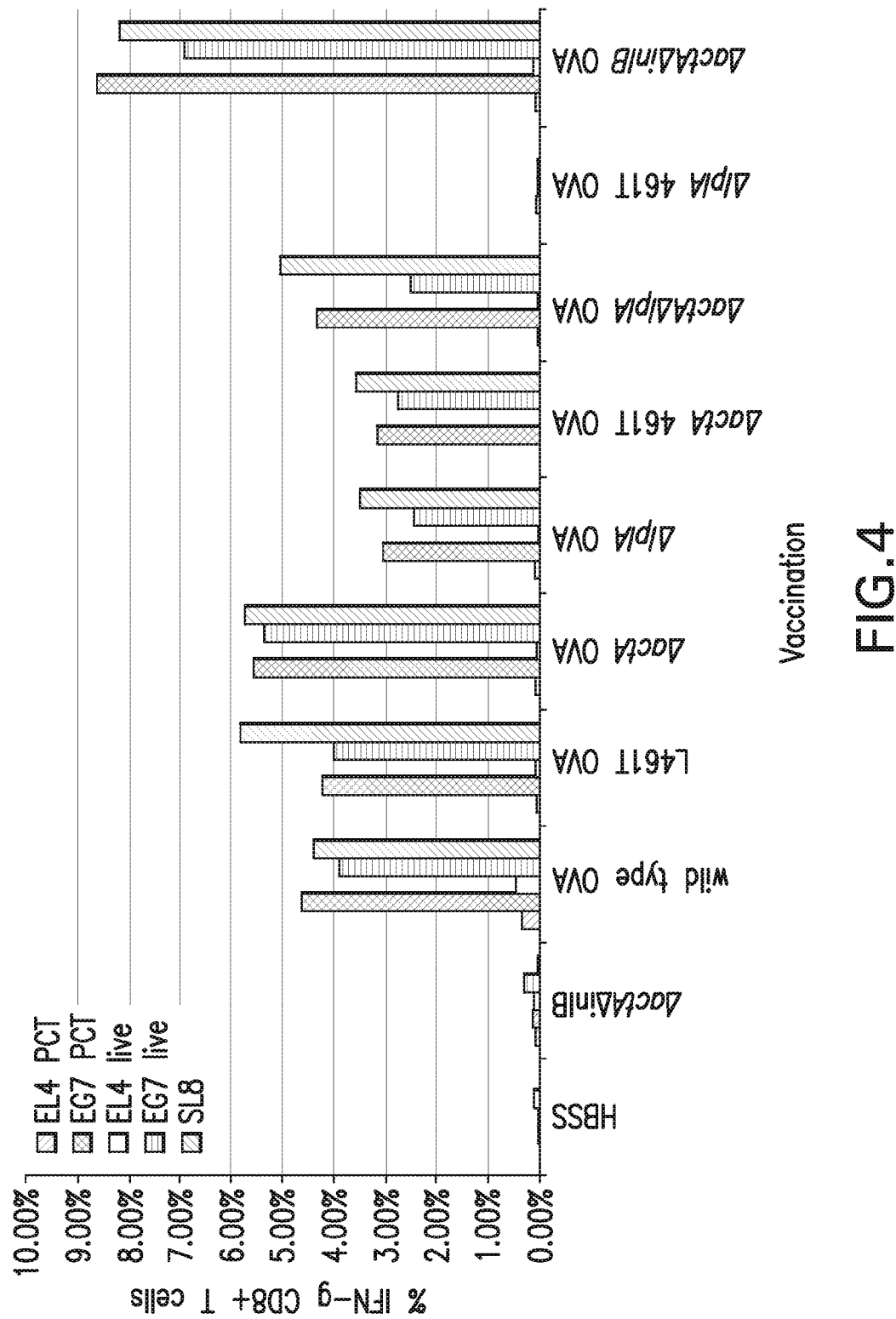
FIG. 4 shows the results of IFN-γ ICS assays for spleen cells from mice vaccinated (intravenously) with mutant Listeria, stimulated with SL8 $OVA_{257-264}$ peptide, live or S-59/UVA inactivated EL-4 cells, or live or S-59/UVA inactivated OVA-expressing EG7 cells.

Assessment of OVA-Specific Immunity Induced by Listeria monocytogenes Strains in C57BL/6 Mice C57BL/6 mice (3 per group) were injected IV with 200 μL HBSS containing 0.1 $LD_{50}$ of the strains indicated in Table 6. The ΔinlB strain was injected at too high of a dose and those mice did not survive 7 days. The mice were sacrificed 7 days after vaccination and the spleens were harvested and antigen-specific T cell responses to the heterologous antigen ovalbumin (OVA) and to Listeria antigen, LLO, were assessed by ICS per Example 5. In addition to stimulating spleen cells of vaccinated and control mice with the T cell epitopes for OVA, SL8 (OVA257-264), and for LLO (LLO190-201, LLO296-304), the cells were stimulated for 5 hours with murine thymoma derived from C57BL/6 mice (EL-4) and EL-4 cells stably transfected with a plasmid encoding ovalbumin (EG-7). The stimulator cells were used either live or following inactivation with 150 μM of psoralen S-59 and 3 J/cm² UVA light (FX 1019 irradiation device, Baxter Fenwal, Round Lake, Ill.). The inactivation with S-59 is referred to as photochemical treatment (PCT) and results in complete inactivation of the cells. The results, excluding the LLO stimulated samples, for IFN-γ are shown in FIG. 4. Comparable stimulation of spleen cells of vaccinated mice was observed when either the optimal T cell epitope SL8 or whole tumor cells, live or inactivated, were used for the 5 hour stimulation. The stimulation with whole cells implies that the OVA-specific T cells recognize endogenous levels of OVA in the context of tumor cells. The ΔactAΔinlB strain results in a relatively strong OVA specific response for stimulation with peptide as well as whole cells.

TABLE 6

Vaccination of C57BL/6 mice with various strains of Listeria monocytogenes.

| Vaccination strain | Description | Vaccination dose (CFU) |
|---|---|---|
| HBSS | Control | 100 μL |
| DP-L4029 ΔinlB | ΔactAΔinlB double mutant | $1 \times 10^8$ |
| DP-L4056 OVA | Wild type | $5 \times 10^4$ |
| DP-L4017 OVA | L461T LLO mutant | $7.5 \times 10^6$ |
| DP-L4029 OVA | ΔactA | $1 \times 10^7$ |
| DP-L 4364 OVA | lplA⁻ | $2 \times 10^7$ |
| DP-L 4406 OVA | ΔinlB | $1 \times 10^6$ |
| DP-L4038 OVA | ΔactA L461T double mutant | $2 \times 10^7$ |
| DP-L4029 lplA⁻ OVA | ΔactAΔlplAdouble mutant | $2 \times 10^8$ |
| DP-L4017 lplA⁻ OVA | lplA⁻L461T double mutant | $1 \times 10^7$ |
| DP-L4029 ΔinlB OVA | ΔactAΔinlB double mutant | $1 \times 10^8$ |

Figure 5:
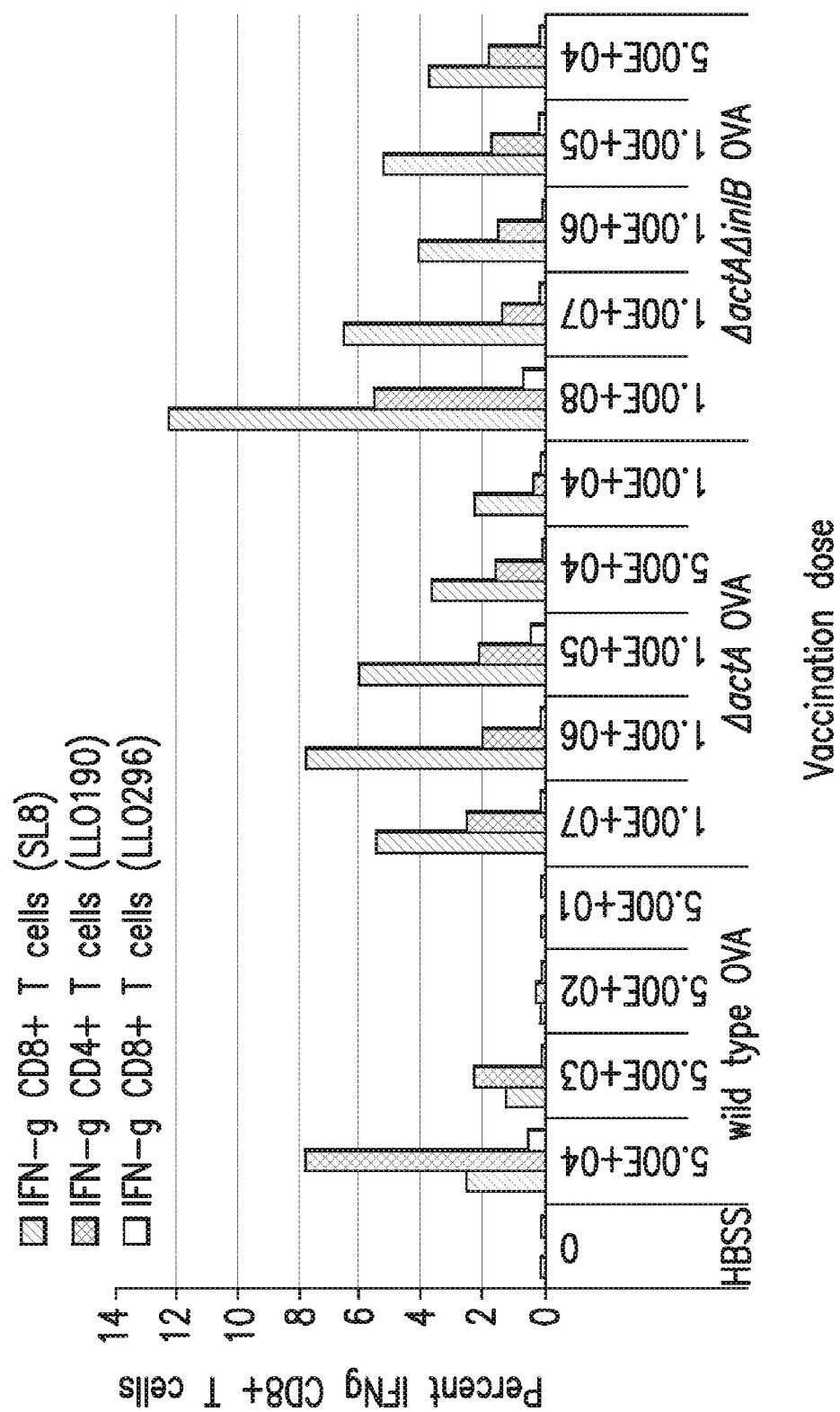
FIG. 5 shows the results of IFN-γ ICS assays for spleen cells from mice vaccinated (intravenously) with varying doses of mutant Listeria, stimulated with SL8 $OVA_{257-264}$ peptide.

Another study was done to look at a dose response using Listeria monocytogenes wild type, ΔactA and ΔactAΔinlB strains modified to express OVA. C57BL/6 mice (3 per group) were injected IV with 200 μL HBSS as follows; wild type at $5 \times 10^4$, $5 \times 10^3$, $5 \times 10^2$, $5 \times 10^1$, ΔactA at $1 \times 10^7$, $1 \times 10^6$, $1 \times 10$, $5 \times 10^4$, $1 \times 10^4$, and ΔactAΔinlB at $1 \times 10^8$, $1 \times 10^7$, $1 \times 10^6$, $1 \times 10^5$, $5 \times 10^4$. The mice were sacrificed 7 days after vaccination and the spleens were harvested and assessed by ICS, stimulating with SL8, $LLO_{190}$ and $LLO_{296}$ peptides. The results are shown in FIG. 5.

Example 7

Figure 6:
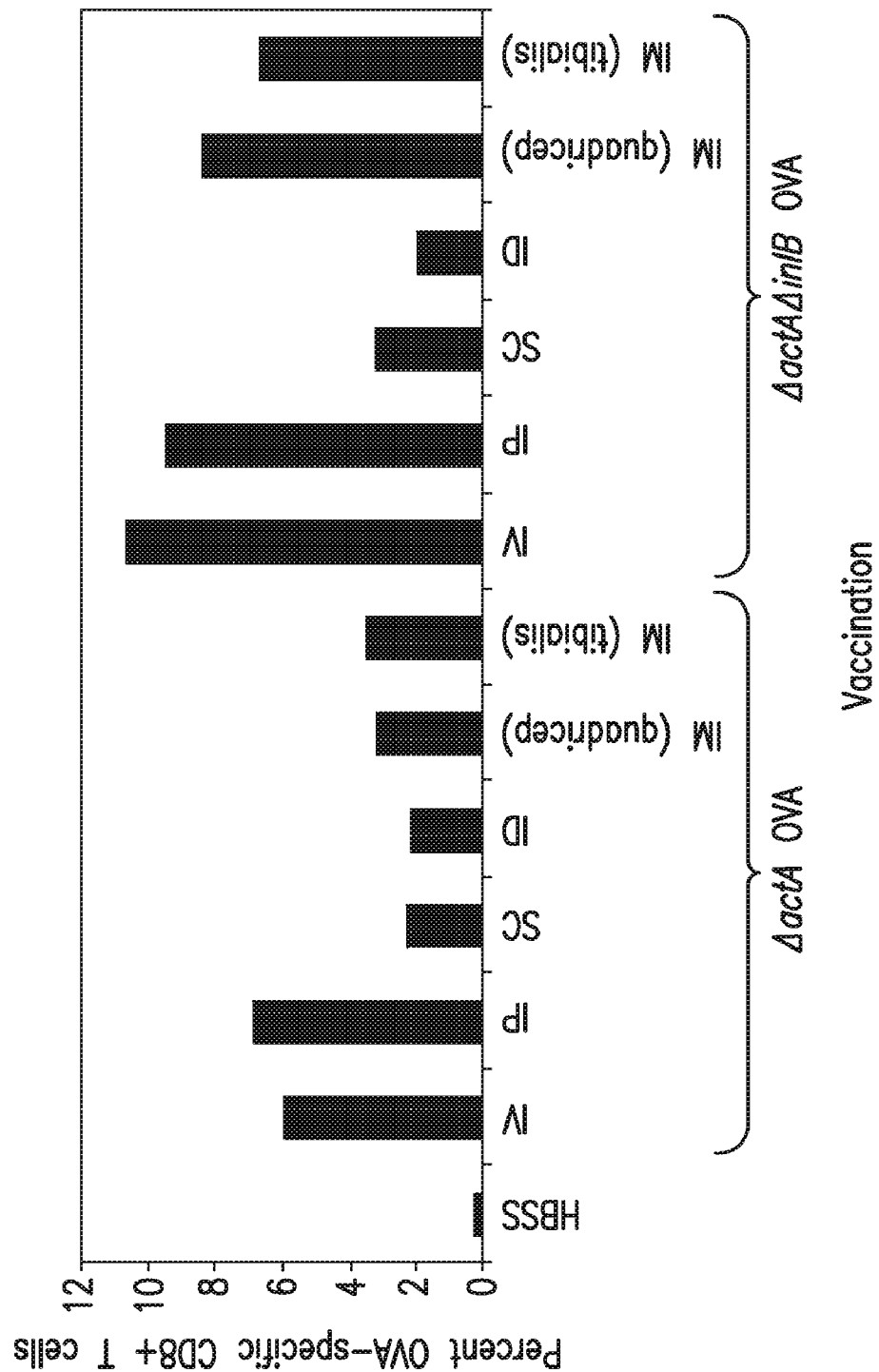
FIG. 6 shows the results of IFN-γ ICS assays for spleen cells from mice vaccinated via different routes with mutant Listeria, stimulated with SL8 $OVA_{257-264}$ peptide.

Immunogenicity of Listeria monocytogenes ΔactAΔinlB Double Mutant Expressing LLO-OVA Administered via Different Routes in Mice Balb/c mice were injected with Listeria monocytogenes ΔactA (DP-L4029) or Listeria monocytogenes ΔactAΔinlB double mutant, where both mutants were engineered to express OVA antigen. Mice (three per group) were injected with $1 \times 10^7$ CFU of ΔactA or $1 \times 10^8$ CFU of ΔactAΔinlB in HBSS either 200 μL IV (intraveneous), 100 μL SC (subcutaneous), 100 μM (intramuscular, 50 μL per quadricep of each leg), 50 μL IM (25 μL per tibial is of each leg), 50 μL ID (intradermal), or 200 μL IP (intraperitoneal). Seven days post vaccination, the spleens were removed and assessed by Intracellular Cytokine Staining (ICS) per Example 5 (SL8 only, IFN-γ only). FIG. 6 shows the % of CD-8+ OVA specific T-cells in the spleen, indicating that the actA/inlB mutant gives a greater response than ΔactA by several routes of administration, with IV, IP, and IM routes showing the highest responses.

Example 8

In Vivo Growth Kinetics of Listeria monocytogenes ΔactAΔinlB Mutant in Naïve Immuno-Competent C57BL/6 Mice Although attenuated strains of Listeria can be administered at higher doses compared to wild type, it is important for the development of a safe vaccine that the infection can be cleared rapidly, without damaging the primary organs of infection, i.e. liver or spleen.

Figure 7A:
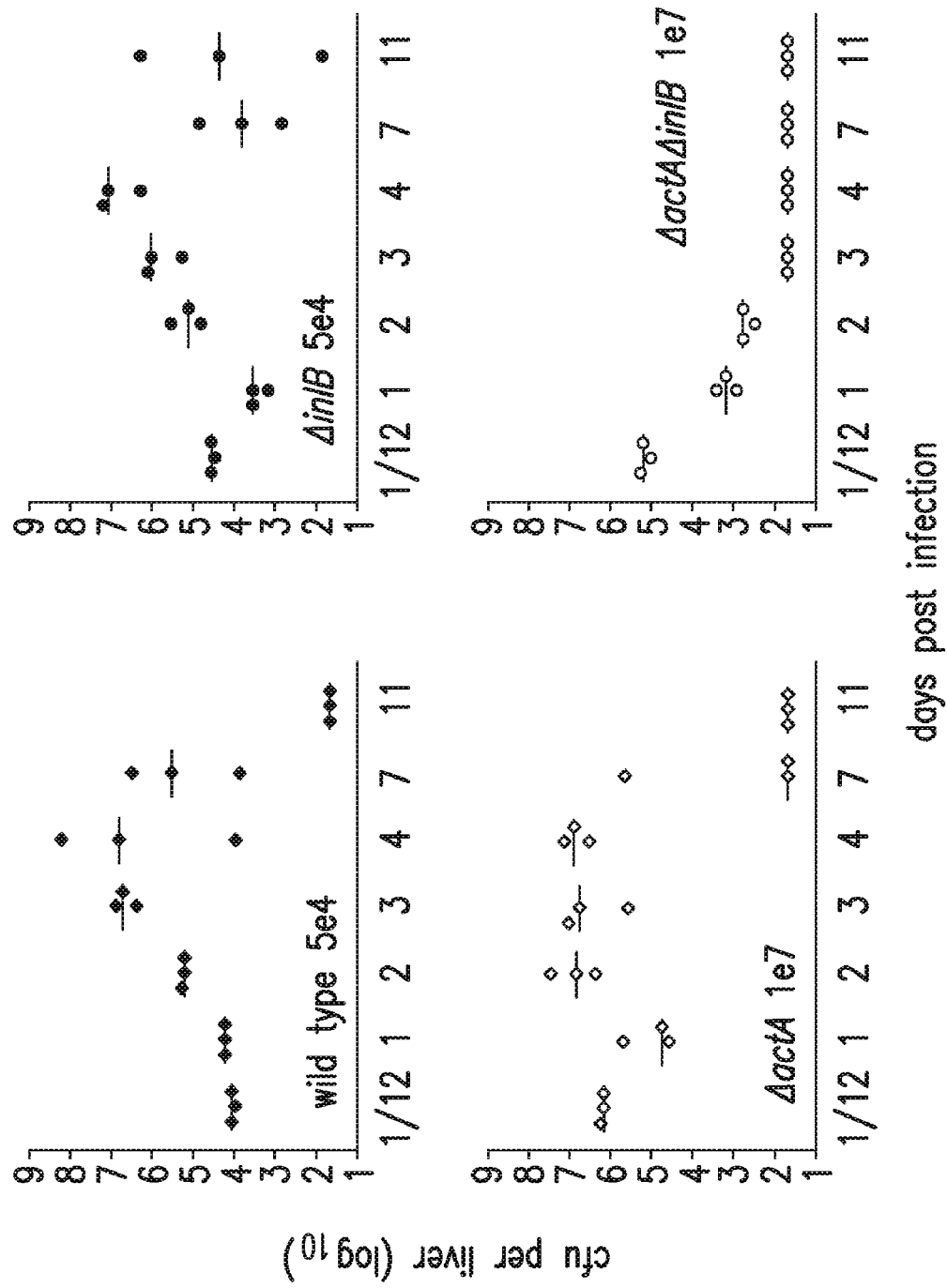
FIGS. 7A and 7B show the accelerated clearance of Listeria monocytogenes ΔactAΔinlB strain in vivo. Bacteria levels in the liver over time are shown in the figure.
Figure 7B:
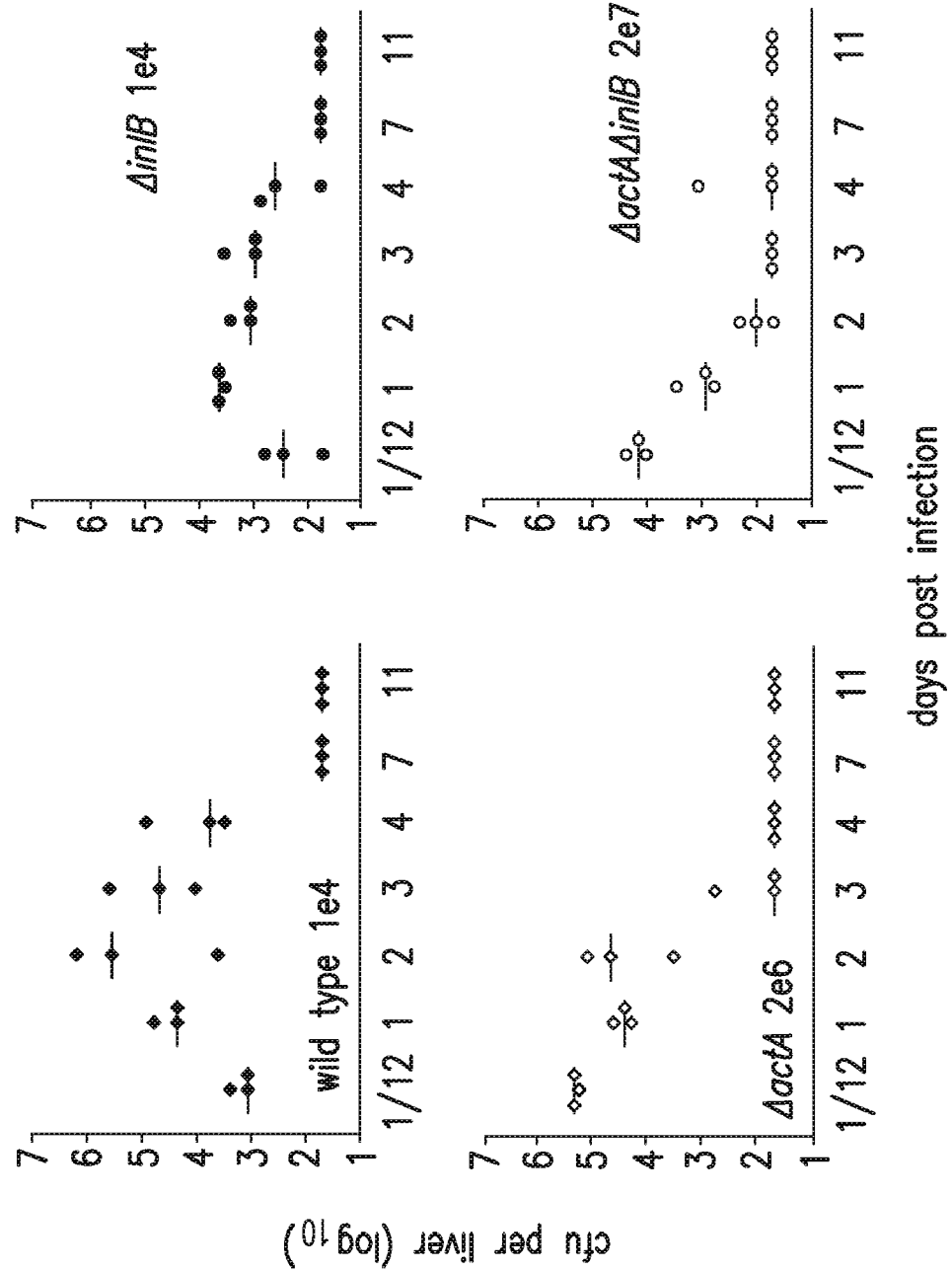
Figure 8A:
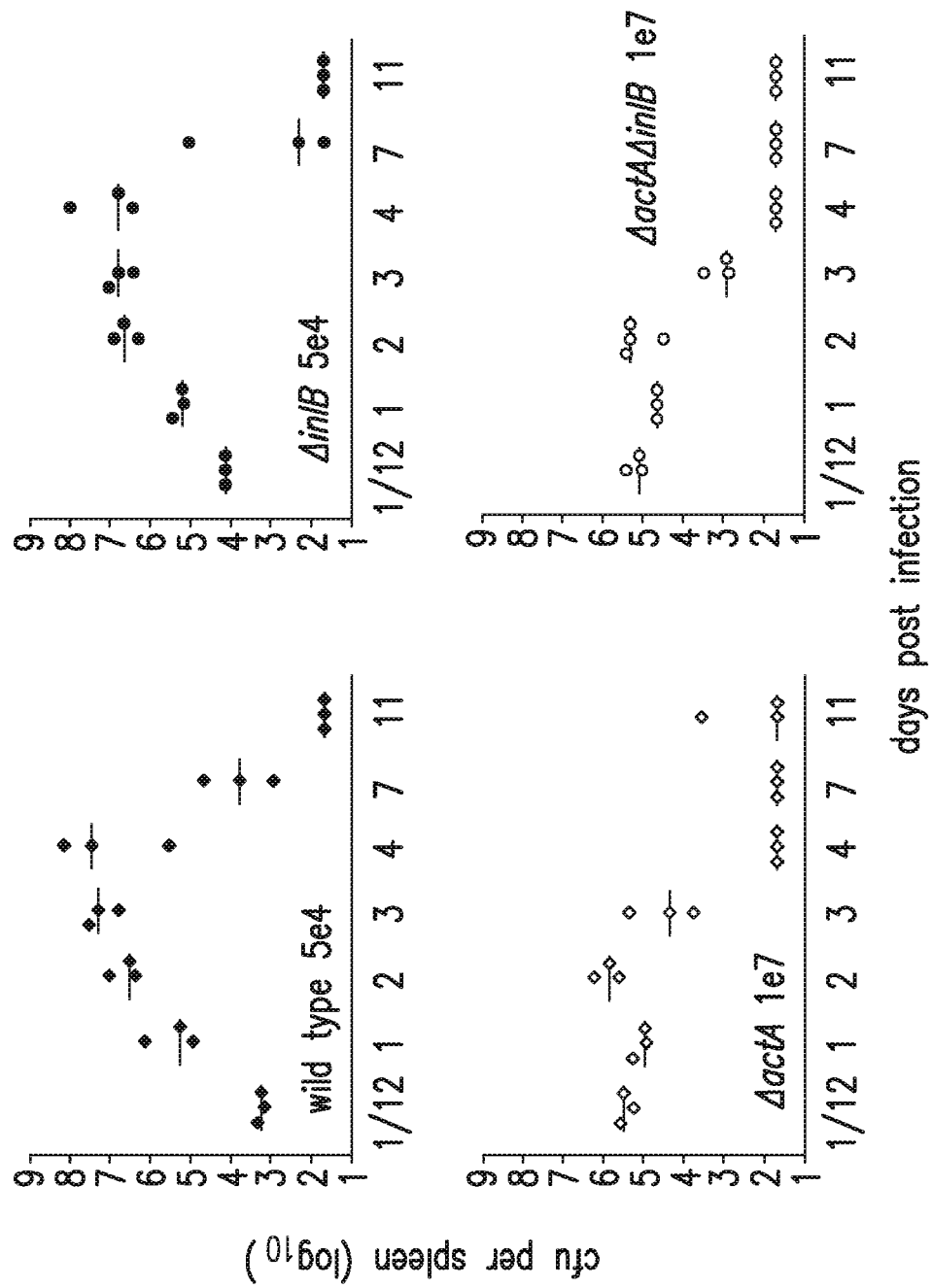
FIGS. 8A and 8B show the accelerated clearance of Listeria monocytogenes ΔactAΔinlB strain in vivo. A time course of bacteria levels in the spleen is shown in the figure.
Figure 8B:
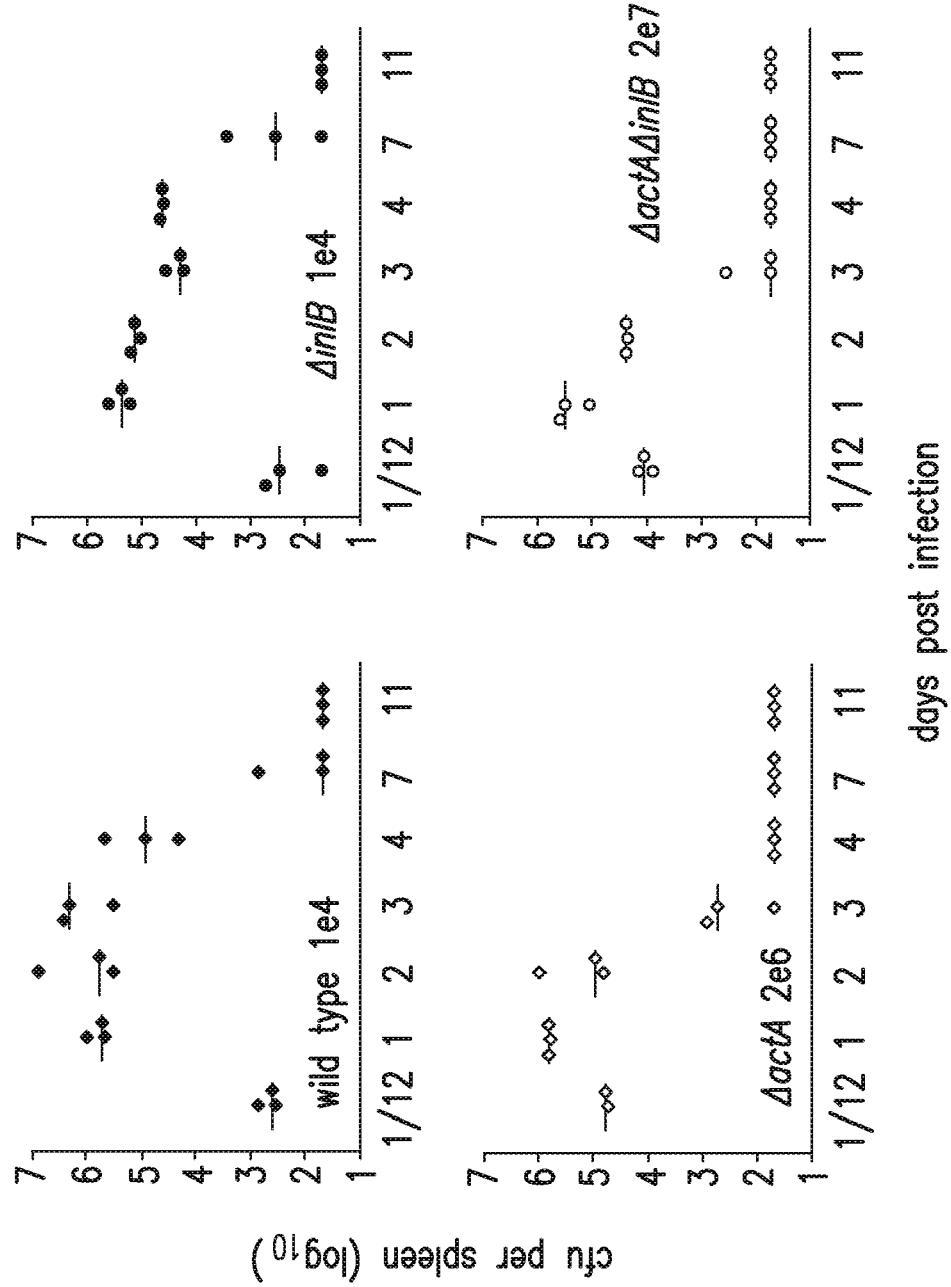

C57BL/6 mice were injected with either DP-L4056 (wild type) DP-L4029 (ΔactA), DP-L 4406 (ΔinlB) or ΔactAΔinlB strains of Listeria monocytogenes. Injections were 100 μL IV in HBSS at the levels indicated in Table 7, 35 mice per group including HBSS control group. All strains were grown in BHI medium (Brain Heart Infusion, Fisher Scientific) at 37° C. at 300 rpm and stored frozen prior to use. Three mice per group were sacrificed at the timepoints indicated in Table 7, and blood, spleen and liver were removed for analysis. The liver and spleens were homogenized in 5 mL of double distilled water with 0.05% Triton X-100 and the number of viable Listeria were determined by plating serial dilutions on BHI/streptomycin plates. The liver and spleens were fixed in 10% buffered formalin for 2 mice per group. The results for CFU per liver and spleen are indicated in FIGS. 7A and 8A. The experiments were also repeated at the strain concentrations shown in FIGS. 7B and 8B.

Infection of mice with wild type Listeria resolved within 8 to 11 days post administration. The number of wild type Listeria steadily increased significantly over the time period of 4 days and decreased to the minimum level of detection in spleen and liver by day 11. Interestingly, the ΔinlB mutant demonstrated a similar kinetic in spleen as well as the liver, with induction of sterile immunity at day 11. In contrast, the number of ΔactA mutant only increased over the first 24 hrs 10-fold in the liver, but not in the spleen, and eventually decreased following day 4 post infection. The ΔactAΔinlB double mutant, although administered at the highest dose, was eliminated very quickly in the liver as compared to the other three strains and sterile immunity was induced by day 4. The accelerated clearance of the bacteria stands in contrast with its ability to induce potent protective as well as antigen-specific immunity in therapeutic tumor model.

TABLE 8

Dosing and sampling schedule for in vivo growth kinetic study of attenuated Listeria monocytogenes.

| Strain | Dose | Take down time post injection |
|---|---|---|
| HBSS | 100 μL | 2 hrs, days 1, 2, 3, 4, 7, and 10 |
| Wild type | $5 \times 10^4$ | 2 hrs, days 1, 2, 3, 4, 7, and 10 |
| ΔactA | $1 \times 10^7$ | 2 hrs, days 1, 2, 3, 4, 7, and 10 |
| ΔinlB | $5 \times 10^4$ | 2 hrs, days 1, 2, 3, 4, 7, and 10 |
| ΔactAΔinlB | $1 \times 10^7$ | 2 hrs, days 1, 2, 3, 4, 7, and 10 |

Example 9

In Vitro Infection of Non-Phagocytic vs Phagocytic Cells with Various Strains of Listeria monocytogenes Listeria monocytogenes wild type, ΔactA, ΔinlB and ΔactAΔinlB strains were incubated (37° C. with 5% $CO_2$) with human monocyte cell line THP-1 (ATCC #TIB-202), primary human monocytes, human hepatocyte cell line HepG2 (from Drew Pardoll, Johns Hopkins University; also available as ATCC # HB8065), or primary human hepatocytes (In vitro Technologies, Baltimore, Md.). Primary human monocytes were prepared from whole blood using a Ficoll gradient to purify lymphocytes, then monocytes were isolated using magnetic beads conjugated to monocyte specific antibody (Miltenyi Biotec). THP-1 and human monocytes were incubated in RPMI media supplemented with 10% heat-inactivated fetal bovine serum (FBS), 23.8 mM sodium bicarbonate, 1× non-essential amino acids, 2 mM L-glutamine, 10 mM HEPES buffer, and 1 mM sodium pyruvate. The Listeria strains were added at $5 \times 10^5$ CFU to $5 \times 10^5$ THP-1 cells and $3.5 \times 10^7$ CFU to $3.5 \times 10^5$ monocytes. HepG2 cells were incubated in Minimal Essential Media Eagle supplemented with 20% heat-inactivated fetal calf serum, 2 mM L-glutamine, and 1× nonessential amino acids. The Listeria strains were added at $1 \times 10^6$ CFU to $1 \times 10^5$ HepG2 cells. Primary human hepatocytes were incubated in Hepatocyte Growth Incubation Media (In vitro Technologies) prior to adding Listeria and incubated in DMEM supplemented with 10% FBS, 2 mM L-glutamine and 1x non-essential amino acids after adding the Listeria. The Listeria strains were added at $3.5 \times 10^6$ CFU to $3.5 \times 10^5$ hepatocytes. After incubation for one hour, the cells were washed with complete media containing gentamicin (50 μg/mL) in order to kill any extracellular bacteria. The cells were then lysed with 225 μL sterile water, then 25 mL of 10× PBS was added. The resulting solution was plated on BHI with serial dilutions to assess the bacterial titer from each sample. The number of Listeria infecting the cells was divided by the Listeria added to the cells to determine the infectivity of the strain, normalized to the infectivity of the wild type strain.

Figure 9:
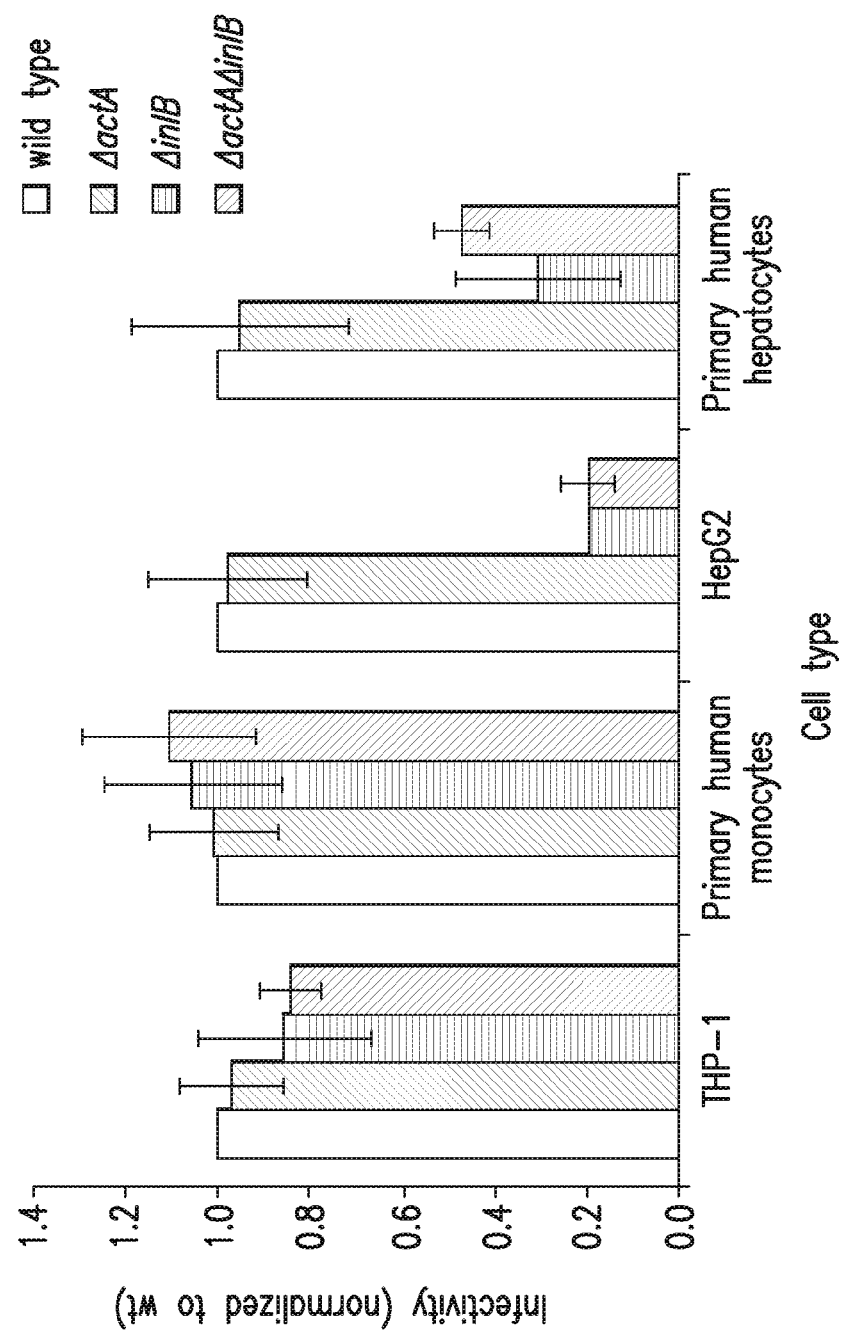
FIG. 9 shows that the Listeria monocytogenes ΔinlB strain and the Listeria monocytogenes ΔactAΔinlB strain are attenuated for entry into non-phagocytic cells, but not phagocytic cells in vitro.

The results are shown in FIG. 9. As shown in FIG. 9, all strains are able to infect THP-1 cells and human monocytes at a similar rate, demonstrating that the absence of ActA or InlB does not affect the infection of phagocytic cells. However, the infection of hepatocytes was significantly decreased for Listeria strains lacking InlB. There is approximately a 60% reduced infection of human hepatocytes and a 80% reduction in HepG2 cells when infecting with either of the InlB null mutant strains, ΔinlB or ΔactAΔinlB. These studies demonstrate that the deletion of InlB protein selects for uptake by phagocytic cells by preventing the infection of cultured and primary hepatocytes.

Example 10

In Vitro Infection of Non-Phagocytic vs Phagocytic Cells with Opsonized Listeria monocytogenes Wild-type Listeria was pre-incubated with high titer Listeria-specific mouse serum from mice infected iv with ΔactA Listeria mutant (1:20 dilution) or HBSS as a control for 1 hour in ice. The phagocytic dendritic cell-like cell line (DC 2.4) and the non-phagocytic colon epithelial cell line (Caco-2) were infected at MOIs of 1 and 10, respectively, for 1 hour at 37° C. The cells were washed three times to remove extracellular bacteria. Cells were cultured for an additional 2 hours in the presence of 50 mg/ml gentamicin to kill remaining extracellular bacteria. To determine the infectivity of the cell lines, cells were lysed with $dH_2O$ containing 0.01% Triton X-100. The number of viable Listeria was determined by plating serial dilutions onto BHI agar plates.

Figure 10:
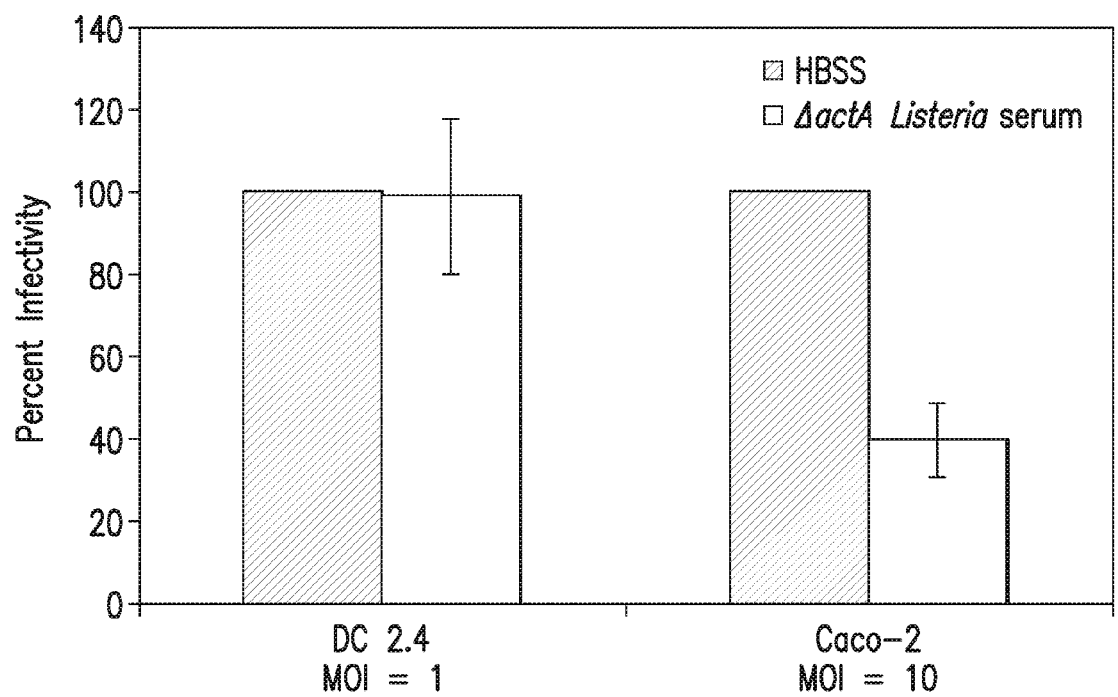
FIG. 10 shows that high titer anti-Listeria serum inhibits uptake by non-phagocytic cells, but not by phagocytic cells.

As shown in FIG. 10, Listeria ΔactA incubated with high-titer immune serum from vaccinated mice have a reduced ability to infect the non-phagocytic cell line Caco-2, but not of the phagocytic dendritic cell line DC2.4. The decreased infection of non-phagocytic cells by opsonized Listeria is comparable to the attenuated Listeria strain that is deleted for actA and inlB (FIG. 9). Without wishing to be bound by theory, the use of Listeria-specific antibodies (monoclonal antibody targeting internalins, or polyclonal Abs) may block the receptors on the surface of the Listeria ΔactA bacterium that enable the infection of non-phagocytic cells in vivo.

Example 11

Exemplary S-59 Psoralen UVA Treatment of Listeria

An ΔactAΔuvrAB mutant strain of Listeria (DP-L4029 uvrAB) was modified to express the OVA antigen. This strain and DP-L4029 modified to express OVA were treated with the psoralen S-59 at various concentrations. The Listeria strains were grown overnight at 37° C. and a 2 mL aliquot was diluted into 100 mL of BHI and grown approximately 4 hours at 37°

C. to an OD600 of 0.5 (approximately $1\times10^9$ CFU/mL). A 5 mL aliquot of each *Listeria* strain was added to a 15 mL tube and centrifuged for 20 minutes at 2300×g, the supernatant removed, and the bacteria resuspended in 5 mL of PBS resulting in approximately $1\times10^9$ CFU/mL. For the uvrAB mutant strain, 3 mM S-59 stock was diluted 33.3 µL to 10 mL PBS to give a 10 µM solution, and appropriate aliquots of this was added to the *Listeria* to final concentrations of 10, 20, 30, 40, 50, 60, 70, 80, 90, and 100 nM, while for the DP-L4029, S-59 was added to final concentrations of 100, 200, 400, 800, and 1000 nM in a final volume of 5 mL. These were transferred to a 6 well culture plate and irradiated for a dose of 0.5 J/cm$^2$ (FX1019 UVA device). The samples were transferred to 15 mL tubes, 5 mL PBS was added, and they were centrifuged for 20 minutes at 2300×g to wash out unreacted psoralen. The supernatant was removed and the bacteria resuspended in 5 mL PBS and transferred to new 6 well plates. These were irradiated at a UVA dose of 5.5 J/cm$^2$ in order to convert psoralen monoadducts to crosslinks. A sample of each *Listeria* strain was also heat killed by treating at 72° C. for 3 hours.

The antigen presentation of the bacterial samples was assessed using a murine DC 2.4 cell line (dendritic cell line from the Dana Farber Cancer institute, see Shen et al., J Immunol 158(6):2723-30 (1997)) and a B3Z T cell hybridoma (obtained from Dr. Shastri, University of California, Berkeley). The B3Z is a lacZ inducible CD8+ T cell hybridoma that expresses a β-galactosidase gene upon recognition of OVA antigen in context of MHC class I molecules. The metabolism of CPRG (chlorophenolred-β-D-galactopyranoside, Calbiochem, La Jolla, Calif.), a substrate for the β-galactosidase, was used to assess the level of β-galactosidase produced, which is directly correlated to the amount of OVA antigen presented by the DC 2.4 cells. The DC 2.4 cells and the B3Z T cell hybrid were maintained in RPMI 1640 culture medium (RPMI, Invitrogen) with 10% FBS (fetal bovine serum, HyClone). The DC 2.4 cells were transferred in 200 µL aliquots to the wells of a 96 well culture plate ($1\times10^5$ DC 2.4 per well). The bacterial samples were serially diluted 50 µL stock to 450 µL PBS down to $1\times10^5$ CFU/mL (S-59 treated samples are CFU equivalents, i.e. it is the number of colony forming units prior to S-59 treatment). A 20 µL aliquot of each dilution is transferred to a well containing the DC 2.4 cells to give approximately $1\times10^4$, $1\times10^5$, $1\times10^6$, $1\times10^7$, or $1\times10^8$ CFU/mL. In addition, a 20 µL aliquot of PBS only was added as a negative control. The samples were incubated for 1 hour at 37° C. in 5% CO$_2$. The plate was washed three times with PBS to remove extracellular bacteria. A 200 µL aliquot of B3Z T cells ($1\times10^5$ cell) and 100 µg/mL Gentamycin (Sigma) was added to each well. As a positive control, 100 nM SL8 OVA$_{257-264}$ peptide (SL8 OVA antigen, SIINFEKL, (SEQ ID NO:21), Invitrogen, San Diego, Calif.) was added to a well containing $1\times10^5$ each of the DC 2.4 and B3Z cells. The samples were incubated overnight at 37° C. in 5% CO$_2$. The plate was centrifuged for 3 minutes at 400×g and each well washed with 250 µL of PBS. A 100 µL aliquot of PBS containing 100 µM 2-mercaptoethanol, 9 mM MgCl$_2$, 0.125% Igepal CA-630 ((Octaphenoxy)polyethoxyethanol, Sigma), and 0.15 mM CPRG was added to each well. The samples were incubated at 37° C. for at least 4 hours. The absorbance was measured at 595 nm with a reference measurement at 655 nm using a plate reader.

The results for the S-59 treated samples are found in Table 8A and FIGS. 11A and 11B (antigen presentation at 1 *Listeria* per DC 2.4 cell, calculated without subtracting background levels. The results for both heat killed strains showed a titer below the limit of detection (complete inactivation) and the heat killed bacteria did not present OVA antigen in the B3Z assay. The results indicate that the uvrAB mutant shows very strong antigen presentation even with attenuation of proliferation to the limit of detection where the non uvrAB mutant strain shows a greater reduction in the antigen presentation as a function of attenuation of proliferation (to approximately background levels with essentially complete inactivation). This demonstrates that the uvrAB mutant retains MHC class I presentation in the context of psoralen attenuated *Listeria* and should provide a vaccine with an effective immune response and significantly increased level of safety.

TABLE 8A

Log attenuation and OVA antigen presentation of *Listeria* strains UVA treated with varying concentrations of psoralen S-59.

| | Log attenuation | | % OVA antigen presented* | |
|---|---|---|---|---|
| [S-59] nM | DP-L4029- OVA | DP-L4029 uvrAB-OVA | DP-L4029- OVA | DP-L4029 uvrAB-OVA |
| 10 | | 2.47 | | 84 |
| 20 | | 3.93 | | 84 |
| 30 | | 5.28 | | 76 |
| 40 | | 6.44 | | 76 |
| 50 | | 6.92 | | 68 |
| 60 | | >7.62 | | 84 |
| 70 | | >7.62 | | 84 |
| 80 | | >7.62 | | 88 |
| 90 | | >7.62 | | 92 |
| 100 | 3.85 | >7.62 | 50 | 92 |
| 200 | 5.48 | | 47 | |
| 400 | 6.78 | | 19 | |
| 800 | >7.78 | | 13 | |
| 1000 | >7.78 | | 13 | |

*As percent of untreated, measured at 1 *Listeria* per DC 2.4 cell.

Another study was done using the same strains. In this study the *Listeria* were grown in BHI at 37° C. overnight. These were diluted 1:50 into BHI and grown at 37° C. at 300 rpm to an OD$_{600}$ of 0.5, at which point 50 mL of solution was transferred to a clean flask and S-59 was added to a to the levels indicated in Table 12B. These samples were incubated at 37° C. at 300 rpm for approximately 1 hour (OD$_{600}$ approximately 1.0, approximately $1\times10^9$/mL). A 1 mL aliquot was removed to assess the titer and the remaining was transferred to a 150 mm Petri dish and irradiated at a dose of 6 J/cm$^2$ (FX1019). The titer post irradiation was determined for each sample and the OVA antigen presentation was assessed as above. The results are found in Table 8B and FIGS. 11C and 11D (antigen presentation at 10 *Listeria* per DC 2.4 cell, calculated without subtracting background levels). The results indicate that for the parent strain, the antigen presentation is at background levels where there is essentially complete inactivation whereas for the uvrAB mutant, there is an approximately 10-fold range of S-59 concentration over which there is essentially complete inactivation along with adequate antigen presentation.

TABLE 8B

Log attenuation and OVA antigen presentation of *Listeria* strains UVA treated with varying concentrations of psoralen S-59 present during growth of the bacteria.

| | Log attenuation | | % OVA antigen presented* | |
|---|---|---|---|---|
| [S-59] µM | DP-L4029- OVA | DP-L4029 uvrAB-OVA | DP-L4029- OVA | DP-L4029 uvrAB-OVA |
| 0.025 | | 3.64 | | 91 |
| 0.05 | | 5.70 | | 86 |
| 0.1 | | >8.10 | | 87 |
| 0.2 | | >8.10 | | 86 |

TABLE 8B-continued

Log attenuation and OVA antigen presentation of *Listeria* strains UVA treated with varying concentrations of psoralen S-59 present during growth of the bacteria.

| [S-59] μM | Log attenuation | | % OVA antigen presented* | |
|---|---|---|---|---|
| | DP-L4029-OVA | DP-L4029 uvrAB-OVA | DP-L4029-OVA | DP-L4029 uvrAB-OVA |
| 0.25 | 2.00 | | 50 | |
| 0.4 | | >8.10 | | 74 |
| 0.5 | 5.28 | | 31 | |
| 0.8 | | >8.10 | | 50 |
| 1.0 | 7.57 | | 14 | |
| 1.6 | | >8.10 | | 35 |
| 2.0 | >8.38 | | 11 | |
| 3.2 | | >8.10 | | 16 |
| 4.0 | >8.38 | | 10 | |
| 6.4 | | >8.10 | | 11 |
| 8.0 | >8.38 | | 10 | |
| 16.0 | >8.38 | | 11 | |

*As percent of untreated, measured at 10 Listeria per DC 2.4 cell.

Example 12

Effectiveness of *Listeria* Mutants in Stimulating Antigen-Specific Responses in the Presence of Pre-Existing Immunity and/or Antibodies Pre-existing anti-*Listeria* immunity was induced by infecting C57BL/6 mice IP with 0.1 $LD_{50}$ of wild-type *Listeria* given once or three times (10 days apart). Mice with *Listeria* immunity (1 or 3 vx) and naïve mice were vaccinated ip 32 days post last *Listeria* exposure with 0.1 LD50 of the indicated *Listeria* strain. Seven days later spleens were harvested and the frequency of OVA-specific CD8+ T cells was determined by intracellular cytokine staining for IFN-g. The results are shown in FIG. 12A. Priming of OVA-specific CD8+ T-cell responses were observed in mice with a level of pre-existing immunity that protects against a lethal challenge of wild type *Listeria*.

Pre-existing anti-*Listeria* immunity was induced in all C57BL/6 mice by infecting intraperitoneally with 0.1 LD50 of wild-type *Listeria*. Mice were vaccinated ip 70 days later with 0.1 LD50 of the indicated *Listeria* strain. After 21 days, mice were implanted subcutaneously with 2e5 B16-OVA tumor cells, and tumors were measured twice weekly. The results are shown in FIG. 12B. Tumor studies demonstrated that the OVA-specific immune response mounted in the presence of anti-*Listeria* immunity can effectively protect against B16-OVA tumor challenge.

High titer immune serum was generated by infecting C57BL/6 mice intravenously four times with 0.1 LD50 of the indicated strain Immune and non-immune serum was harvested and titer determined by *Listeria*-specific ELISA. Naïve C57BL/6 mice were injected iv with 200 ul of saline, serum (immune or non-immune), or rabbit polyclonal anti-*Listeria* antibody on Day −1 and 1. Mice were vaccinated iv with 0.1 LD50 of ΔactA-OVA *Listeria* on Day 0. Spleens were harvested and the frequency of OVA-specific CD8+ T cells was determined by intracellular cytokine staining for IFN-g. The results are shown in FIG. 12C. The results show that passive transfer of *Listeria*-specific antibody to naïve mice did not reduce priming of a primary OVA-specific cellular immune response in treated mice.

All publications, patents, patent applications, and accession numbers (including both polynucleotide and polypeptide sequences) cited herein are hereby incorporated by reference in their entirety for all purposes to the same extent as if each individual publication, patent or patent application were specifically and individually indicated to be so incorporated by reference.

What we claim is:

1. An attenuated *Listeria monocytogenes* bacterium, wherein the attenuated bacterium comprises:
   one or more genetic mutations in the actA gene and the inlB genes which attenuates the ability of the *Listeria* to spread relative to wild type *Listeria monocytogenes* and which attenuates the ability of the *Listeria* to invade at least some cells relative to wild type *Listeria monocytogenes*; and
   a functional genomic inlA gene, whereby the attenuated bacterium expresses InlA protein.

2. An attenuated *Listeria monocytogenes* bacterium according to claim 1, wherein the mutation(s) in the actA gene and the inlB genes comprise a deletion of all or a portion of the coding region of the actA gene and the inlB genes.

3. An attenuated *Listeria monocytogenes* bacterium according to claim 1, further comprising: (i) interstrand crosslinks introduced between the strands of genomic DNA double helix, said interstrand crosslinks inhibiting replication of said attenuated bacterium, and (ii) one or more genetic mutations in uvrA and uvrB genes inhibiting excision repair of said interstrand crosslinks.

4. An attenuated *Listeria monocytogenes* bacterium according to claim 1, further comprising a nucleic acid sequence encoding a polypeptide heterologous to said attenuated bacterium operably linked to a promoter sequence directing expression of the heterologous polypeptide by the attenuated bacterium.

5. An attenuated *Listeria monocytogenes* bacterium according to claim 3, wherein the interstrand crosslinks are introduced by reaction with a psoralen activated by irradiation or by reaction with an alkylating agent.

6. An attenuated *Listeria monocytogenes* bacterium according to claim 5, wherein the interstrand crosslinks are introduced by reaction with 4'-(4-amino-2-oxa)butyl-4,5',8-trimethylpsoralen activated by irradiation.

7. An attenuated *Listeria monocytogenes* bacterium according to claim 4, wherein the polypeptide heterologous to said attenuated bacterium is a tumor antigen.

8. An attenuated *Listeria monocytogenes* bacterium according to claim 7, wherein the tumor antigen is mesothelin, SPAS-1, proteinase-3, SP-17, gp100, PAGE-4, TARP, Her-2/neu, WT-1, NY-ESO-1, PSMA, K-ras, survivin, mcm-2, or CEA, or an antigen derived from mesothelin, SPAS-1, proteinase-3, SP-17, gp100, PAGE-4, TARP, Her-2/neu, WT-1, NY-ESO-1, PSMA, K-ras or CEA.

9. An attenuated *Listeria* bacterium according to claim 4, wherein the polypeptide heterologous to said attenuated bacterium is an infectious disease antigen.

10. An attenuated *Listeria* bacterium according to claim 9, wherein the antigen is derived from a Human Immunodeficiency Virus or a hepatitis virus.

* * * * *

SEQUENCE LISTING

<160> NUMBER OF SEQ ID NOS: 23

<210> SEQ ID NO 1
<211> LENGTH: 9
<212> TYPE: PRT
<213> ORGANISM: Homo Sapiens

<400> SEQUENCE: 1

Val Leu Gln Glu Leu Asn Val Thr Val
1               5

<210> SEQ ID NO 2
<211> LENGTH: 25
<212> TYPE: DNA
<213> ORGANISM: Artificial Sequence
<220> FEATURE:
<223> OTHER INFORMATION: PCR Primer

<400> SEQUENCE: 2
gttaagtttc atgtggacgg caaag                                         25

<210> SEQ ID NO 3
<211> LENGTH: 42
<212> TYPE: DNA
<213> ORGANISM: Artificial Sequence
<220> FEATURE:
<223> OTHER INFORMATION: PCR Primer

```
<400> SEQUENCE: 3
aggtcttttt cagttaacta tcctctcctt gattctagtt at                    42

<210> SEQ ID NO 4
<211> LENGTH: 43
<212> TYPE: DNA
<213> ORGANISM: Artificial Sequence
<220> FEATURE:
<223> OTHER INFORMATION: PCR Primer

<400> SEQUENCE: 4
caaggagagg atagttaact gaaaaagacc taaaaagaa ggc                    43

<210> SEQ ID NO 5
<211> LENGTH: 26
<212> TYPE: DNA
<213> ORGANISM: Artificial Sequence
<220> FEATURE:
<223> OTHER INFORMATION: PCR Primer

<400> SEQUENCE: 5
tcccctgttc ctataattgt tagctc                                      26

<210> SEQ ID NO 6
<211> LENGTH: 25
<212> TYPE: DNA
<213> ORGANISM: Artificial Sequence
<220> FEATURE:
<223> OTHER INFORMATION: PCR Primer

<400> SEQUENCE: 6
gtggacggca agaaacaac caaag                                        25

<210> SEQ ID NO 7
<211> LENGTH: 29
<212> TYPE: DNA
<213> ORGANISM: Artificial Sequence
<220> FEATURE:
<223> OTHER INFORMATION: PCR Primer

<400> SEQUENCE: 7
gttcctataa ttgttagctc attttttc                                    29

<210> SEQ ID NO 8
<211> LENGTH: 9
<212> TYPE: PRT
<213> ORGANISM: Mus Musculus

<400> SEQUENCE: 8

Ser Pro Ser Tyr Val Tyr His Gln Phe
 1               5

<210> SEQ ID NO 9
<211> LENGTH: 9
<212> TYPE: PRT
<213> ORGANISM: Artificial Sequence
<220> FEATURE:
<223> OTHER INFORMATION: Altered Peptide

<400> SEQUENCE: 9

Ser Pro Ser Tyr Ala Tyr His Gln Phe
 1               5

<210> SEQ ID NO 10
<211> LENGTH: 29
```

```
<212> TYPE: DNA
<213> ORGANISM: Artificial Sequence
<220> FEATURE:
<223> OTHER INFORMATION: PCR Primer

<400> SEQUENCE: 10
ctctggtacc tcctttgatt agtatattc                                           29

<210> SEQ ID NO 11
<211> LENGTH: 36
<212> TYPE: DNA
<213> ORGANISM: Artificial Sequence
<220> FEATURE:
<223> OTHER INFORMATION: PCR Primer

<400> SEQUENCE: 11
caatggatcc ctcgagatca taatttactt catccc                                   36

<210> SEQ ID NO 12
<211> LENGTH: 32
<212> TYPE: DNA
<213> ORGANISM: Artificial Sequence
<220> FEATURE:
<223> OTHER INFORMATION: PCR Primer

<400> SEQUENCE: 12
atttctcgag tccatggggg gttctcatca tc                                       32

<210> SEQ ID NO 13
<211> LENGTH: 25
<212> TYPE: DNA
<213> ORGANISM: Artificial Sequence
<220> FEATURE:
<223> OTHER INFORMATION: PCR Primer

<400> SEQUENCE: 13
ggtgctcgag tgcggccgca agctt                                               25

<210> SEQ ID NO 14
<211> LENGTH: 37
<212> TYPE: DNA
<213> ORGANISM: Artificial Sequence
<220> FEATURE:
<223> OTHER INFORMATION: Synthetic Construct

<400> SEQUENCE: 14
cgattcccct agttatgttt accaccaatt tgctgca                                  37

<210> SEQ ID NO 15
<211> LENGTH: 31
<212> TYPE: DNA
<213> ORGANISM: Artificial Sequence
<220> FEATURE:
<223> OTHER INFORMATION: Synthetic Construct

<400> SEQUENCE: 15
gcaaattggt ggtaaacata actaggggaa t                                        31

<210> SEQ ID NO 16
<211> LENGTH: 27
<212> TYPE: DNA
<213> ORGANISM: Artificial Sequence
<220> FEATURE:
<223> OTHER INFORMATION: Synthetic Construct

<400> SEQUENCE: 16
agtccaagtt atgcatatca tcaattt                                             27
```

-continued

```
<210> SEQ ID NO 17
<211> LENGTH: 33
<212> TYPE: DNA
<213> ORGANISM: Artificial Sequence
<220> FEATURE:
<223> OTHER INFORMATION: Synthetic Construct

<400> SEQUENCE: 17
cgatagtcca agttatgcat atcatcaatt tgc                                      33

<210> SEQ ID NO 18
<211> LENGTH: 34
<212> TYPE: DNA
<213> ORGANISM: Artificial Sequence
<220> FEATURE:
<223> OTHER INFORMATION: Synthetic Construct

<400> SEQUENCE: 18
gtcgcaaatt gatgatatgc ataacttgga ctat                                     34

<210> SEQ ID NO 19
<211> LENGTH: 9
<212> TYPE: PRT
<213> ORGANISM: Escherichia coli

<400> SEQUENCE: 19

Thr Pro His Pro Ala Arg Ile Gly Leu
 1               5

<210> SEQ ID NO 20
<211> LENGTH: 9
<212> TYPE: PRT
<213> ORGANISM: Listeria monocytogenes

<400> SEQUENCE: 20

Lys Tyr Gly Val Ser Val Gln Asp Ile
 1               5

<210> SEQ ID NO 21
<211> LENGTH: 8
<212> TYPE: PRT
<213> ORGANISM: Gallus gallus

<400> SEQUENCE: 21

Ser Ile Ile Asn Phe Glu Lys Leu
 1               5

<210> SEQ ID NO 22
<211> LENGTH: 12
<212> TYPE: PRT
<213> ORGANISM: Listeria monocytogenes

<400> SEQUENCE: 22

Asn Glu Lys Tyr Ala Gln Ala Tyr Pro Asn Val Ser
 1               5                  10

<210> SEQ ID NO 23
<211> LENGTH: 9
<212> TYPE: PRT
<213> ORGANISM: Listeria monocytogenes

<400> SEQUENCE: 23

Val Ala Tyr Gly Arg Gln Val Tyr Leu
 1               5
```